(12) United States Patent
Shadduck

(10) Patent No.: US 12,114,754 B2
(45) Date of Patent: Oct. 15, 2024

(54) SYSTEMS AND METHODS FOR TREATING SKIN AND LIPS

(71) Applicant: Hermes Innovations, LLC, San Jose, CA (US)

(72) Inventor: John H. Shadduck, Menlo Park, CA (US)

(73) Assignee: John H. Shadduck, Menlo Park, CA (US)

( * ) Notice: Subject to any disclaimer, the term of this patent is extended or adjusted under 35 U.S.C. 154(b) by 23 days.

(21) Appl. No.: 18/177,056

(22) Filed: Mar. 1, 2023

(65) Prior Publication Data

US 2024/0115030 A1 Apr. 11, 2024

Related U.S. Application Data

(60) Provisional application No. 63/378,966, filed on Oct. 10, 2022.

(51) Int. Cl.
| | | |
|---|---|---|
| *A45D 34/04* | (2006.01) | |
| *A45D 40/26* | (2006.01) | |
| *A61B 17/00* | (2006.01) | |
| *A61M 35/00* | (2006.01) | |

(52) U.S. Cl.
CPC .......... *A45D 34/041* (2013.01); *A45D 40/261* (2013.01); *A61B 2017/00747* (2013.01); *A61B 2217/005* (2013.01); *A61M 35/003* (2013.01)

(58) Field of Classification Search
CPC .... A45D 34/041; A45D 34/04; A45D 40/261; A45D 40/26; A45D 2034/005; A61B 17/3205; A61B 17/54; A61B 17/545; A61B 2217/005; A61B 2017/00761; A61B 2017/320004; A61B 2017/00747; A61M 35/003; A61M 35/006; A61M 37/00; A61M 2210/04
USPC .......................... 401/13, 208, 209, 212, 216
See application file for complete search history.

(56) References Cited

U.S. PATENT DOCUMENTS

| | | | |
|---|---|---|---|
| 8,939,669 B2 | 1/2015 | Le et al. | |
| 9,498,610 B2 * | 11/2016 | Ignon | ................. A61B 17/3205 |
| 11,020,577 B2 * | 6/2021 | Ignon | ..................... A61B 17/32 |
| 11,224,728 B2 * | 1/2022 | Ignon | .................... A61M 35/00 |
| 11,707,126 B2 * | 7/2023 | Cho | ..................... A45D 40/261 |
| | | | 401/209 |

* cited by examiner

*Primary Examiner* — David J Walczak
(74) *Attorney, Agent, or Firm* — Levine Bagade Han LLP

(57) ABSTRACT

Methods and devices including a skin or a lip and more particularly methods and devices that enhances absorption of fluid treatment media into tissue for cosmetic and therapeutic purposes.

19 Claims, 50 Drawing Sheets

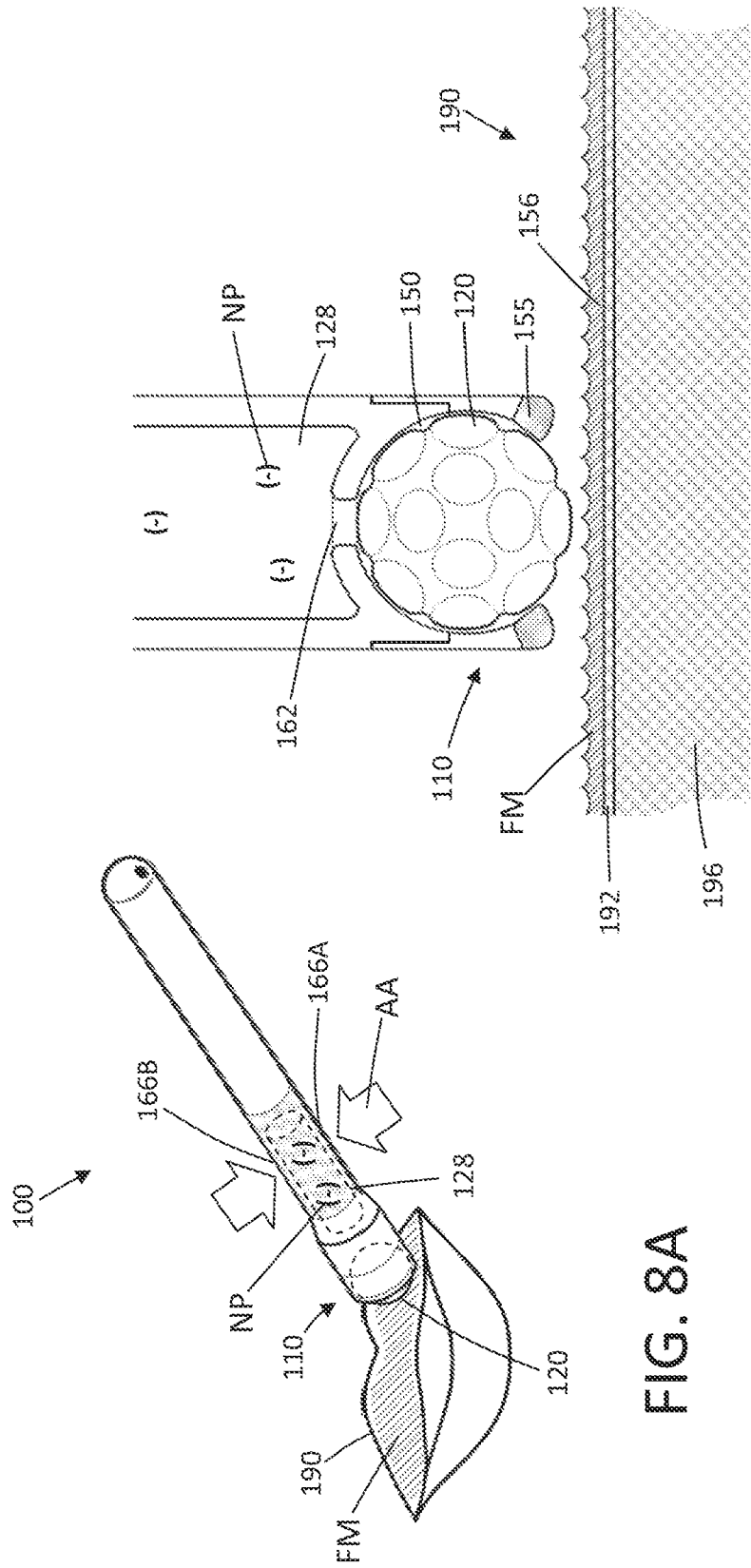

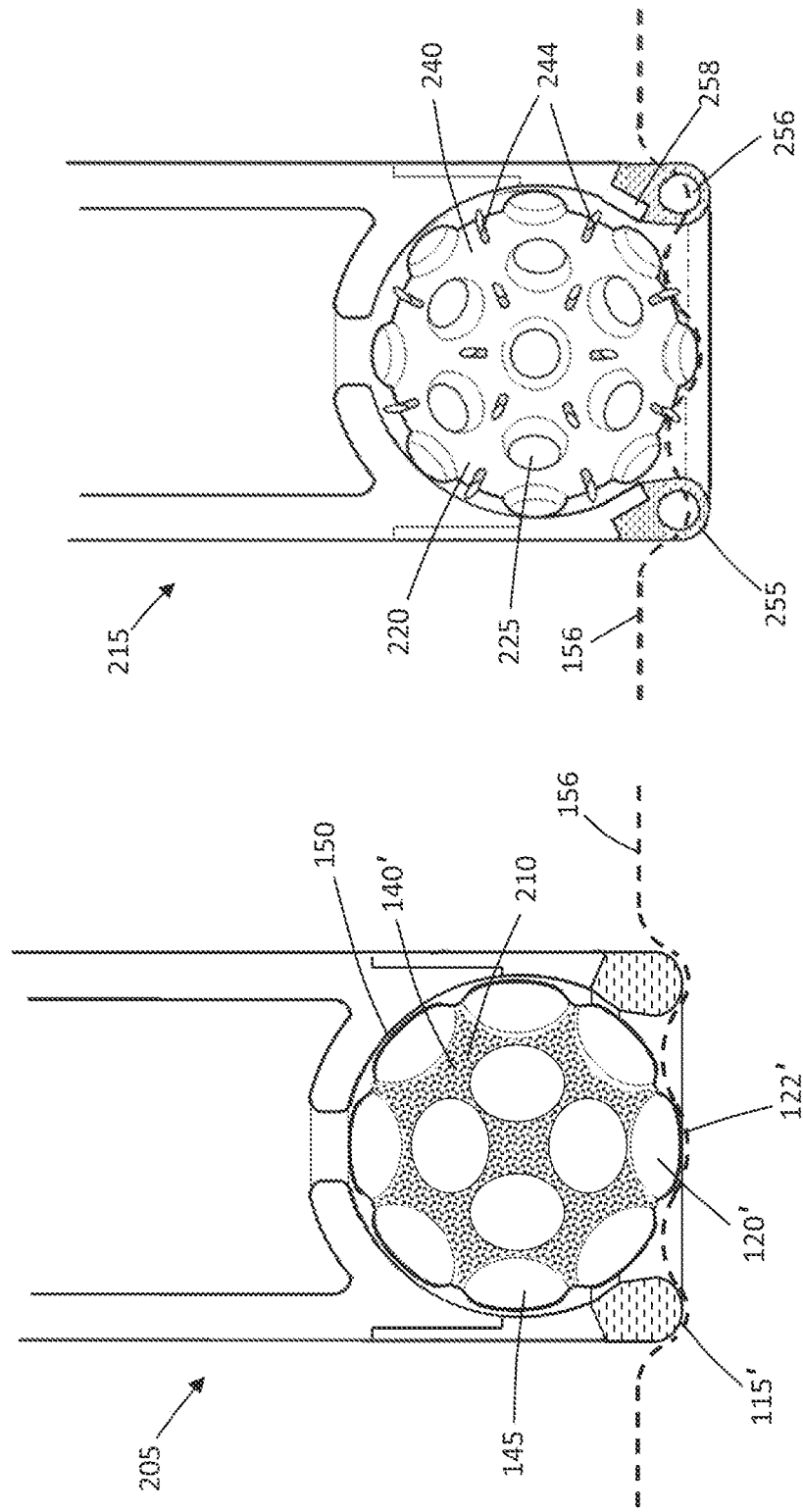

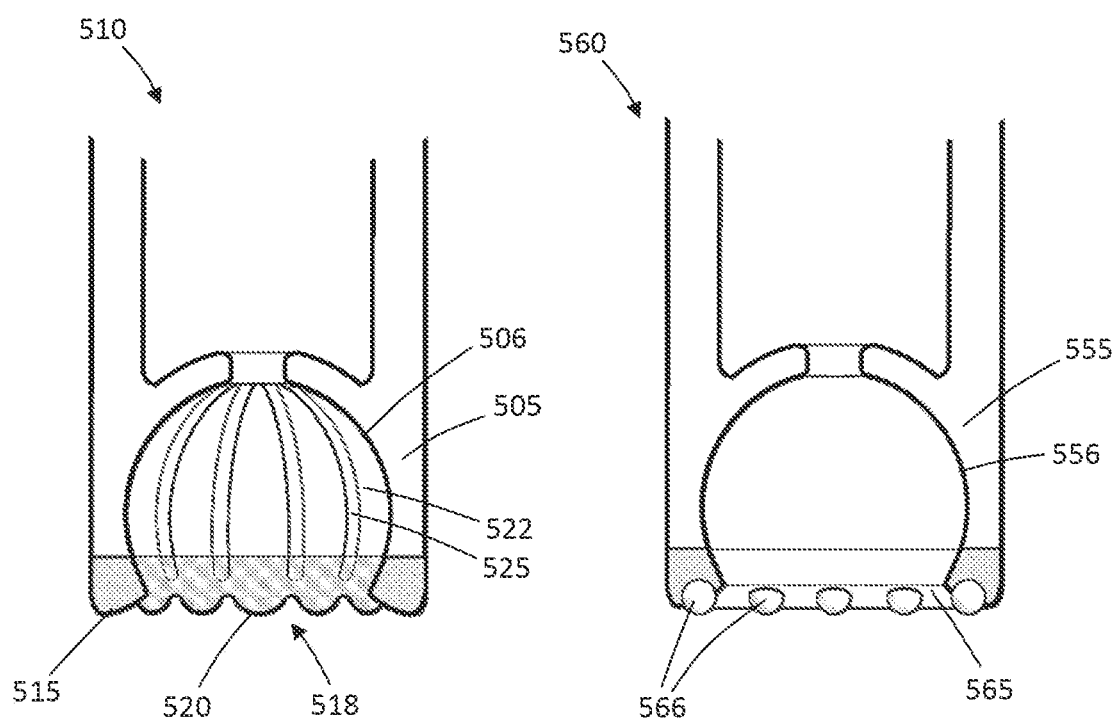

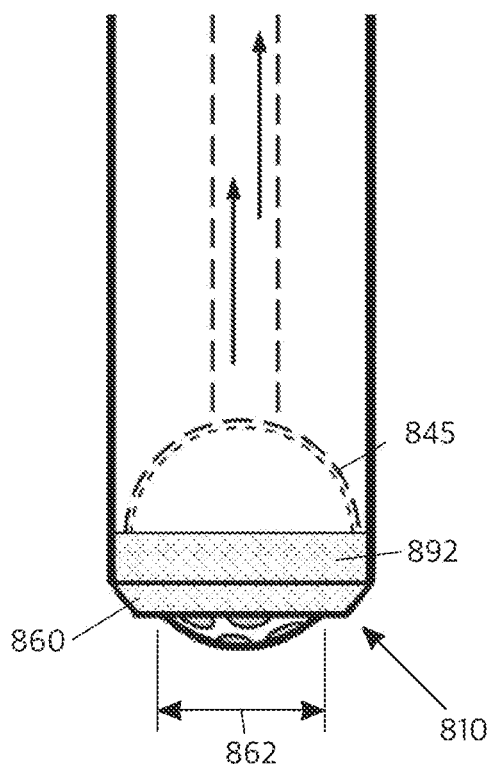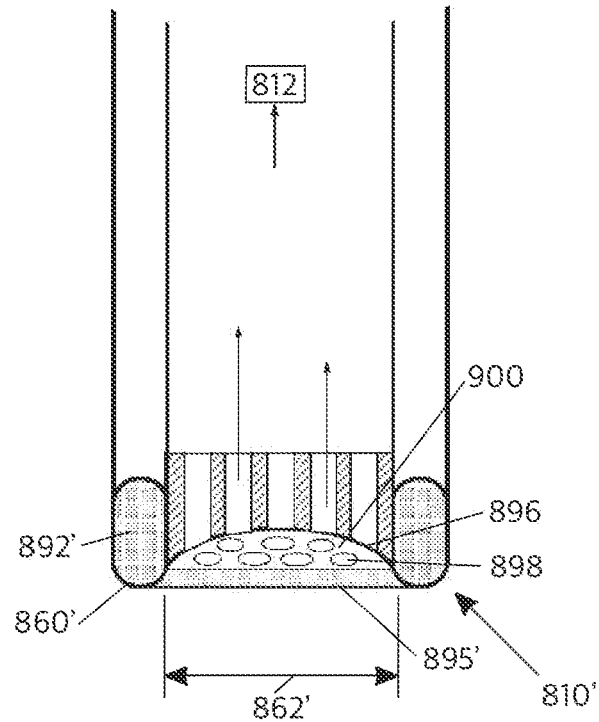
FIG. 29                    FIG. 30

```
┌─────────────────────────────────────────────────────────┐
│ APPLY A TREATMENT MEDIA INCLUDING A HYALURONIC ACID OR  │
│   DERIVATIVE THEREOF TO LIPS OR SKIN SURFACE            │
└─────────────────────────────────────────────────────────┘
                            ▼
┌─────────────────────────────────────────────────────────┐
│ APPLY A SELECTED LEVEL OF NEGATIVE PRESSURE TO THE      │
│ SURFACE OR THE LIPS OR SKIN WITH A DISTAL TIP OF AN     │
│ APPLICATOR                                              │
└─────────────────────────────────────────────────────────┘
                            ▼
┌─────────────────────────────────────────────────────────┐
│ APPLY A PULSED ELECTROPORATION CURRENT TO THE TARGETED  │
│ TISSUE FROM THE DISTAL TIP OF THE APPLICATOR            │
└─────────────────────────────────────────────────────────┘
                            ▼
┌─────────────────────────────────────────────────────────┐
│ CAUSING TRANSPORT OF THE HYALURONIC ACID OR DERIVATIVE  │
│ THEREOF THROUGH THE SURFACE OF THE LIPS OR SKIN         │
└─────────────────────────────────────────────────────────┘
```

FIG. 32B

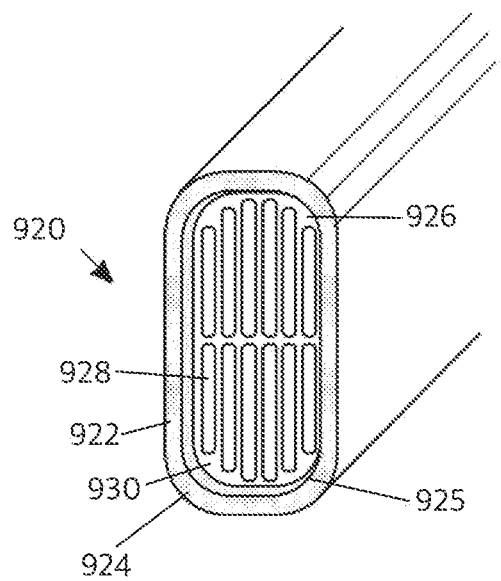
FIG. 34
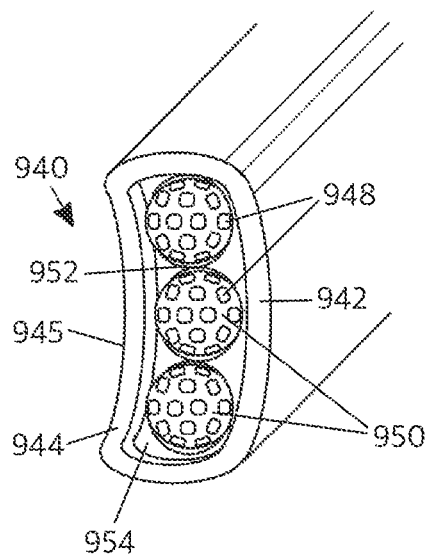 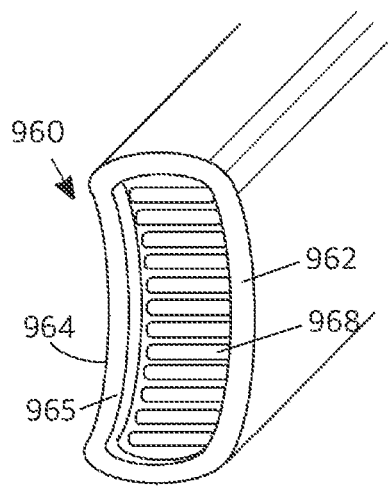
FIG. 35A   FIG. 35B

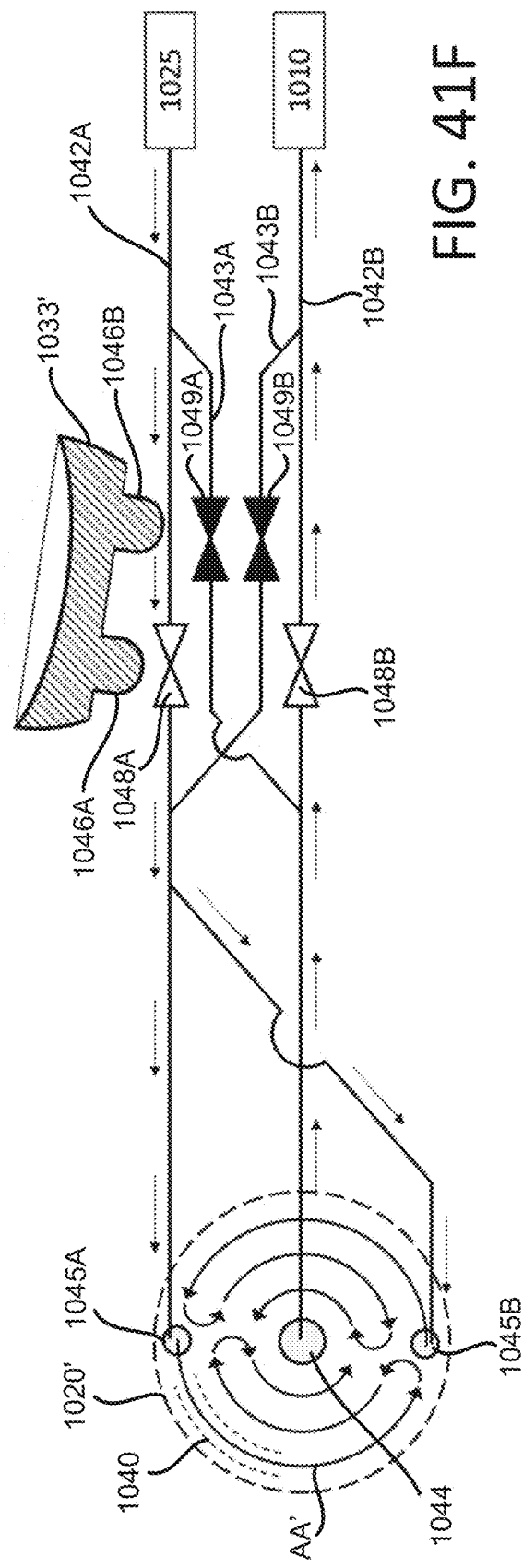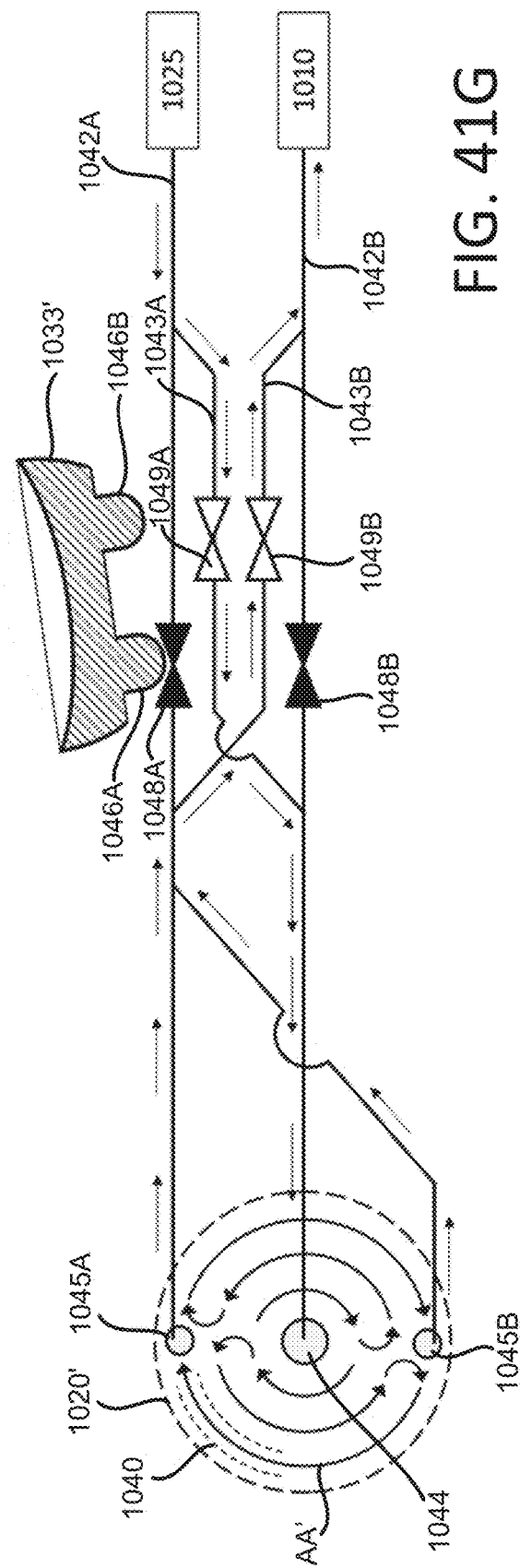

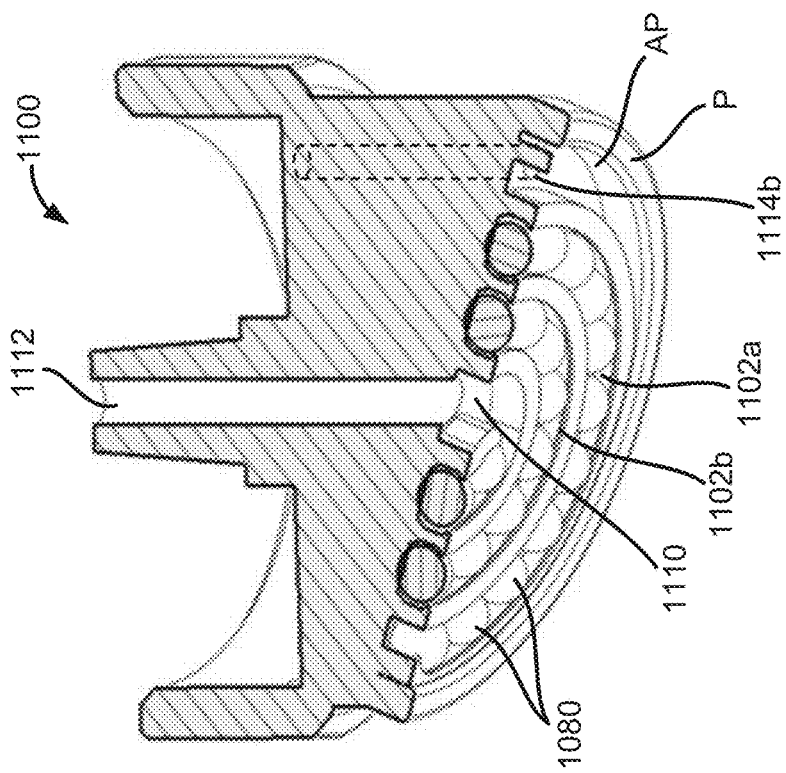
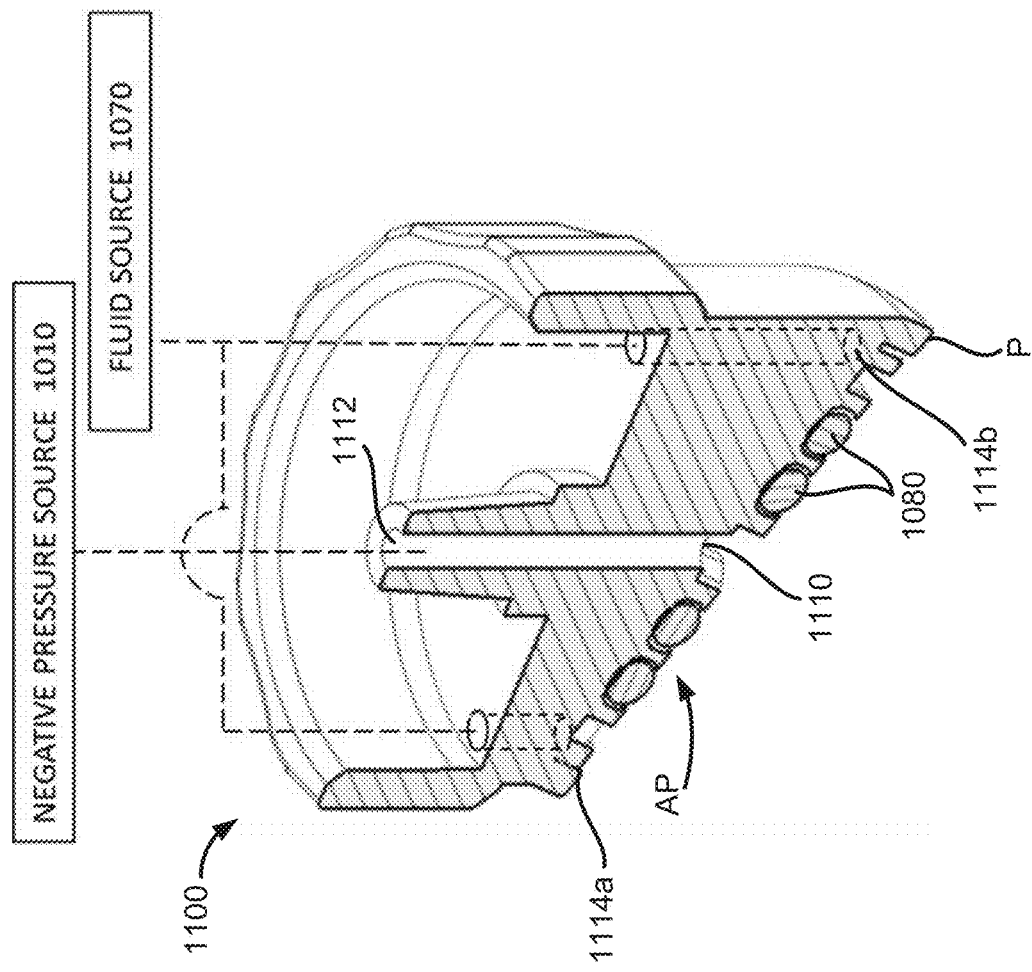
FIG. 43C
FIG. 43D

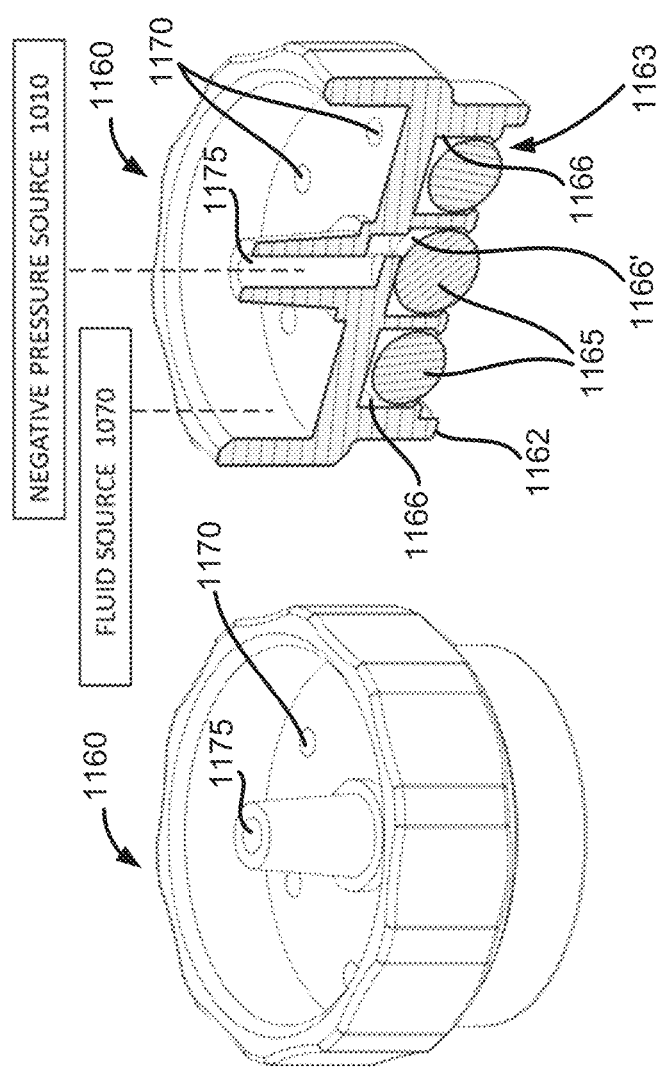
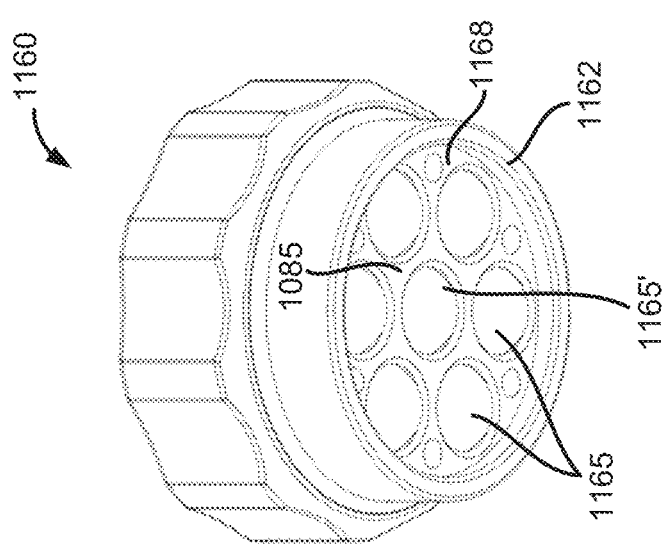
FIG. 45A    FIG. 45B    FIG. 45C

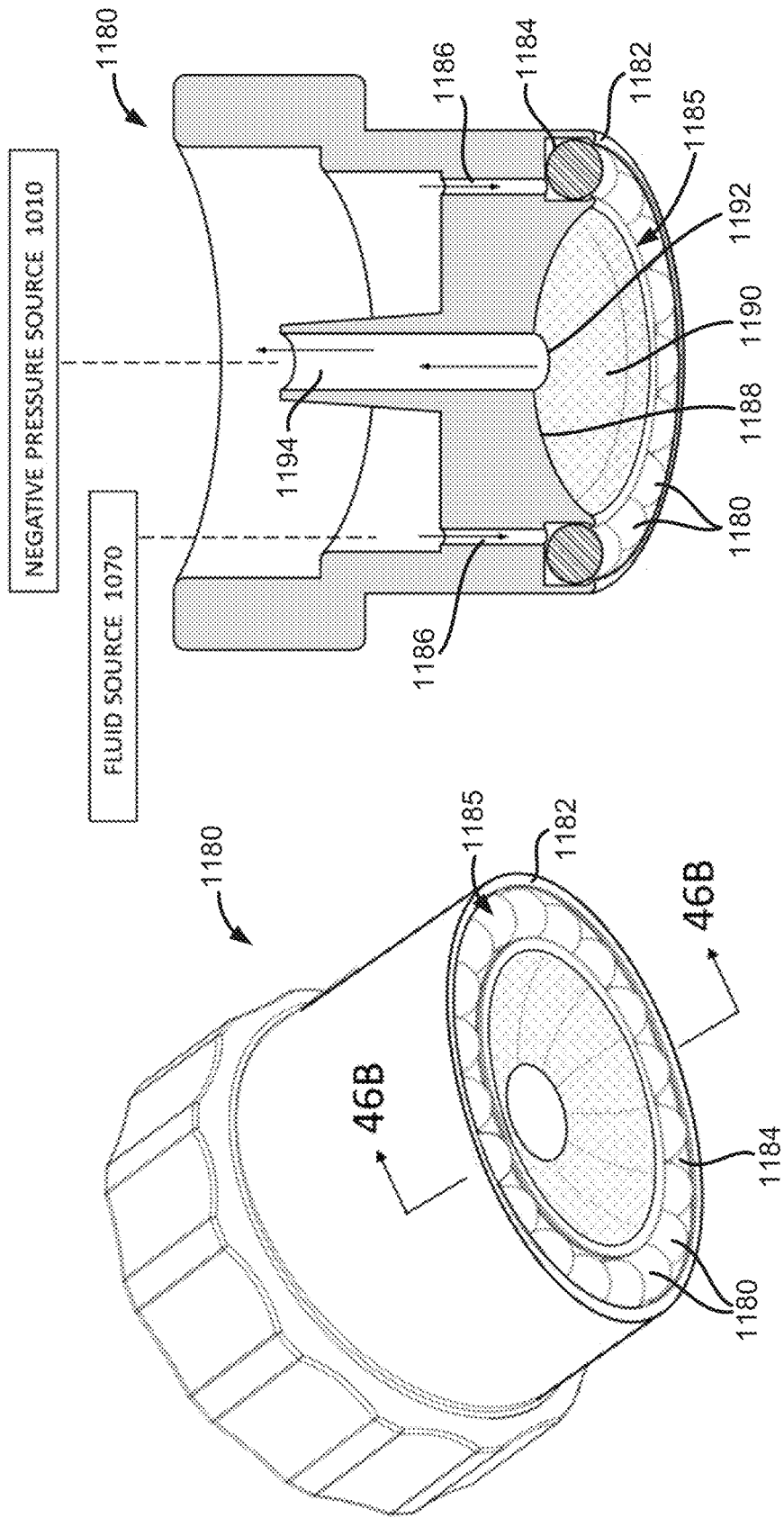

SYSTEMS AND METHODS FOR TREATING SKIN AND LIPS

RELATED APPLICATIONS

This application is a non-provisional of U.S. Provisional Application No. 63/378,966 filed Oct. 10, 2022, which is incorporated by reference.

BACKGROUND

The present disclosure relates to methods and devices for treating a subject's skin or lips and, more particularly, methods and devices that enhance absorption of treatment media into tissue for cosmetic and therapeutic purposes.

SUMMARY OF THE INVENTION

The applicator systems and methods corresponding to the invention relate in general to the fields of skin care, hair restoration, and lip care, wherein the systems may be used by an individual for infusing treatment media into his or her skin or lips for cosmetic and rejuvenation purposes, hair restoration purposes or other therapeutic purposes.

The present disclosure includes devices for enhancing fluid delivery to a subject's skin or lips. For example, one variation of such a device includes an applicator body extending about a longitudinal axis from a proximal end to a distal applicator tip; a rolling member carried in a receiving space of the applicator tip; and a negative pressure mechanism communicating with a flow pathway in the applicator tip for applying negative pressure to tissue engaged by the applicator tip.

A variation of the device can include the applicator body having a distal periphery and where the rolling member and the distal periphery are configured to contact tissue during use. The distal periphery can be configured to create a seal against the tissue during use.

In an additional variation, an exposed portion of the rolling member extends distally from the distal periphery less than 25% of the diameter of the rolling member.

Variations of the rolling member can have a non-smooth surface. Alternatively, or in combination, the surface of the rolling member can be a first surface portion defining a spherical rotational envelope and a second surface portion comprising surface discontinuities. The flow pathway can comprise the surface discontinuities in the rolling member. In some variations, the surface discontinuities comprise at least one of recesses, channels, grooves, notches, facets, bores, and porosities.

Variations of the device can include the first surface portion defining a selected surface area that allows the rolling member to roll smoothly in a cooperating surface of the receiving space. In some examples, the first surface portion has a surface area of at least 40% of the surface area of said spherical rotational envelope of the rolling member.

The variations of the device can include a second surface portion having a surface area of at least 10% of the surface area of said spherical rotational envelope of the rolling member.

In additional variations, the surface of the rolling member can include recessed portions and adjacent projecting portions. Variations of the projecting portions can have a sharp apex. Alternatively, or in combination, a projecting portion can comprise a needle. In yet additional variations, at least a portion of the rolling member has an abrasive surface.

The devices described herein can include a distal periphery that comprises at least one of a resilient material and a lubricious material. The distal periphery can also include an abrasive surface.

The negative pressure mechanisms used herein can comprise any vacuum source. For example, one variation includes a positive displacement pump. In additional variations, the negative pressure mechanism is adapted for manual actuation.

The devices described herein can further comprise a valve in the flow pathway.

In additional variations, the devices can have an applicator body that includes at least first and second detachable elements that, when detached, allow for removal of the rolling member.

Variations of the applicators can carry at least one LED and a rolling member that is at least partly transparent material.

The devices can also include a flow pathway, which comprises surface discontinuities in surface of the receiving space.

The invention described herein also includes methods for treating a subject's skin or lips. For example, one such method includes contacting a tissue surface with a rolling member carried at a distal end of an applicator body; moving the rolling member over the tissue surface; and creating negative pressure about the rolling member in contact with the tissue surface to transiently cause negative pressure in subsurface tissue to enhance permeability of the tissue surface.

The methods described herein can further include applying a treatment media to the tissue surface. In some variations, the moving step manipulates tissue to thereby enhance penetration of the treatment media therein. Alternatively, or in combination, the moving step includes the surface discontinuities of the rolling member causing at least one of compressing, stretching, tensioning, and piercing the tissue surface.

In an additional variation, the method includes a creating step, which suctions treatment media in a circuitous path over the tissue surface about the surface discontinuities to thereby enhance penetration of the treatment media therein.

The methods can also include a distal periphery of the applicator body that contacts tissue to seal the negative pressure around the rolling member as it moves over the tissue surface.

In another variation of the method, the moving step abrades the tissue surface with an abrasive surface of the applicator body to thereby enhance penetration of the treatment media therein.

The present disclosure also includes methods for treating a targeted tissue. For example, such a method can include a targeted tissue that comprises the skin or a lip of a subject. However, any tissue region can be treated by variations of the devices and methods described herein.

In one variation, a method for treating a targeted tissue includes providing an applicator capable of applying a negative pressure within the applicator, wherein a distal tip of the applicator has a perimeter portion surrounding an aspiration portion having a plurality of apertures distributed over the aspiration portion, the distal tip further comprising a low friction surface; contacting the targeted tissue of the skin or the lip with the distal tip of the applicator while maintaining the low friction surface against the targeted tissue; and applying the negative pressure and moving the distal tip over the targeted tissue to transiently cause negative pressure in a subsurface tissue where the low friction surface reduces a friction of the distal tip against the targeted tissue.

The present disclosure also includes devices for treating a targeted tissue. In one example, such a device includes an applicator body carrying a negative pressure source for providing a negative pressure within the applicator body; and a distal tip of the applicator body having a perimeter portion configured for contacting the targeted tissue, wherein the perimeter portion surrounds an aspiration portion, the aspiration portion having a plurality of apertures distributed over the aspiration portion such that a surface of the aspiration portion between the plurality of apertures comprises a non-apertured field, and wherein plurality of apertures are configured to apply with the negative pressure to the targeted tissue; and wherein the plurality of apertures are distributed over the aspiration portion to distribute the negative pressure over all regions of the aspiration portion exposed in the perimeter portion that interface with the targeted tissue.

The methods and devices described herein can include variations where the aspiration portion comprises a rolling member rotatably located within the distal tip and where the plurality of apertures extend through the rolling member such that the rolling member located between the plurality of apertures comprises the low friction surface, wherein moving the distal tip over the targeted tissue causes rotation of the rolling member against tissue and reduces friction between the distal tip and the targeted tissue. The rolling member can roll about a single axis or can rotate in a 360-degree direction.

Variations of the methods and device include a low friction surface that comprises a lubricious material located on the perimeter portion.

The aspiration portions can have a surface area of at least 25 mm2 and the plurality of apertures can each have a width of 2.00 mm or less. In those variations where the apertures are not symmetric, the width of 2.00 mm can be measured across a minor axis.

Variations of the devices and method can be equipped with one or more electrodes that are configured to apply a current into targeted tissue to cause electroporation of the tissue thereby increasing permeability and allowing passage of a substance through a surface of the targeted tissue. The devices and methods can administer any substance to produce a desired therapeutic or other effect. For example, such a substance can include a hyaluronic acid, moisturizer, numbing agent, etc. The methods and devices can also include applying a topical treatment media to the surface of the targeted tissue.

The methods and devices can apply a negative pressure at the distal tip when in contact with tissue during use that is at least negative 3.0 psi. Moreover, controlling the negative pressure can use a controller in the applicator coupled to a negative pressure source. Alternatively, the controller can be external to the applicator and coupled thereto by a wire or wireless connection. Variations of the controller can be responsive to signals from a pressure sensor carried by the applicator that senses negative pressure within the applicator during use. In additional variations, controllers can be configured to control the negative pressure source to maintain a selected negative pressure within the applicator during use.

The controllers can also be responsive to signals from an accelerometer carried by the applicator to modulate or terminate negative pressure in the applicator during use when lack of movement is detected. Additional variations include controllers configured with a time-out feature that stops the negative pressure source after a selected interval of use followed by a selected time-out interval after which the negative pressure source may be activated. The controllers can be configured to pulse the negative pressure source. The controllers can be configured to provide a limit to negative pressure within the applicator body during use and/or to maintain a selected negative pressure within the applicator body during use.

In additional variations, a controller is configured with a time-out feature that stops activation of the negative pressure source after a selected interval of use followed by a selected time-out interval after which the negative pressure source may be re-activated.

The methods and devices described herein can further include use of a mobile electronic device to communicate with the controller through a wireless connection to a bluetooth-type receiver carried by the applicator to adjust operating parameters of the applicator. Variations of the methods and devices can include using a blue-tooth type transmitter carried by the applicator to transmit operating data to a remote electronic device or a cloud storage.

The devices and methods can also include use of an applicator where the perimeter portion comprises a sponge-like material.

The negative pressure sources can be positioned within the applicator or can be external to the applicator. Any type of negative pressure source can be used. One such example includes a motor-driven pump.

Additional variations of the devices include those with a tip having a shape selected from a group of round, oval, rectangular, polygonal and hour-glass shaped. In additional variations, the device can include a surface of perimeter portion has a planar configuration. Alternatively, the surface of the perimeter portion can have a non-planar configuration.

It will be understood that other objects and purposes of the invention, and variations thereof, will be apparent upon reading the following specification and inspecting the accompanying drawings. These and other features, aspects and advantages of the present invention will become better understood with reference to the following drawings.

BRIEF DESCRIPTION OF THE DRAWINGS

FIG. 8A illustrates a first step in a method of the invention where the subject applies a treatment media topically to lips and actuates the squeeze bulb to create negative pressure in the applicator.

FIG. 8B illustrates an enlarged view of the step in the method of FIG. 8A, where the applicator tip is prepared for contact with flowable treatment media applied topically to the tissue surface.

FIG. 9 is a cut-away view of another variation of applicator tip similar to that of FIG. 1, where the rolling member includes abrasive portions for providing traction with tissue.

FIG. 10 is a cut-away view of yet another variation of applicator tip similar to that of FIG. 1, where the rolling member includes sharp micro-needles for providing traction with tissue and for causing penetrations in surface tissue.

FIG. 15 is a sectional view of another variation of roller housing that is configured with an undulating distal periphery for manipulating tissue.

FIG. 16 is a sectional view of another distal roller housing that is configured with a distal periphery carrying a plurality of rollers for reducing friction with a tissue surface during use and for manipulating tissue.

FIG. 29 is an enlarger view of the distal applicator tip of FIG. 26 with a rolling member showing a lubricious or absorbent perimeter portion of the distal tip.

FIG. 30 is an enlarged view of an alternative distal tip of an applicator that has a plurality of apertures communicating with the negative pressure source.

FIG. 32B is an illustration of the steps of the method of causing the transport of hyaluronic acid through the surface of skin or lips.

FIG. 34 is a perspective view of another applicator tip with a rectangular configuration and narrow apertures.

FIG. 35A is a perspective view of another applicator tip configured with a non-planar distal-facing periphery and a plurality of rolling members.

FIG. 35B is a view of another applicator tip with a non-planar distal-facing periphery and a plurality of narrow slit-type apertures.

FIG. 41F is a schematic view of a rocker member of the type shown in FIGS. 41D-41E, wherein the rocker member is adapted to open and close first and second flow channels and cross-over channels to reverse the directions of circuitous fluid flows in a treatment tip.

FIG. 41G is another view of the rocker member and flow channels of FIG. 41F with fluid flows in the distal tip flowing in a reverse direction compared to FIG. 41F.

FIG. 43C is a sectional view of the treatment tip of FIG. 43A.

FIG. 43D is another sectional view of the treatment tip of FIG. 43A from a different angle.

FIG. 45A is a perspective view of another variation of a treatment tip with an outer sealing edge around a recessed central portion that carries rolling members in individual sockets.

FIG. 45B is a view of the treatment tip of FIG. 45A from a different angle.

FIG. 45C is another view of the treatment tip of FIG. 45A from a different angle.

FIG. 46A is a perspective view of a variation of a treatment tip with an outer roller channel carrying rolling members and a central concave portion having an abrasive surface.

FIG. 46B is a sectional view of the treatment tip of FIG. 46A.

DETAILED DESCRIPTION OF THE INVENTION

Figure 1:
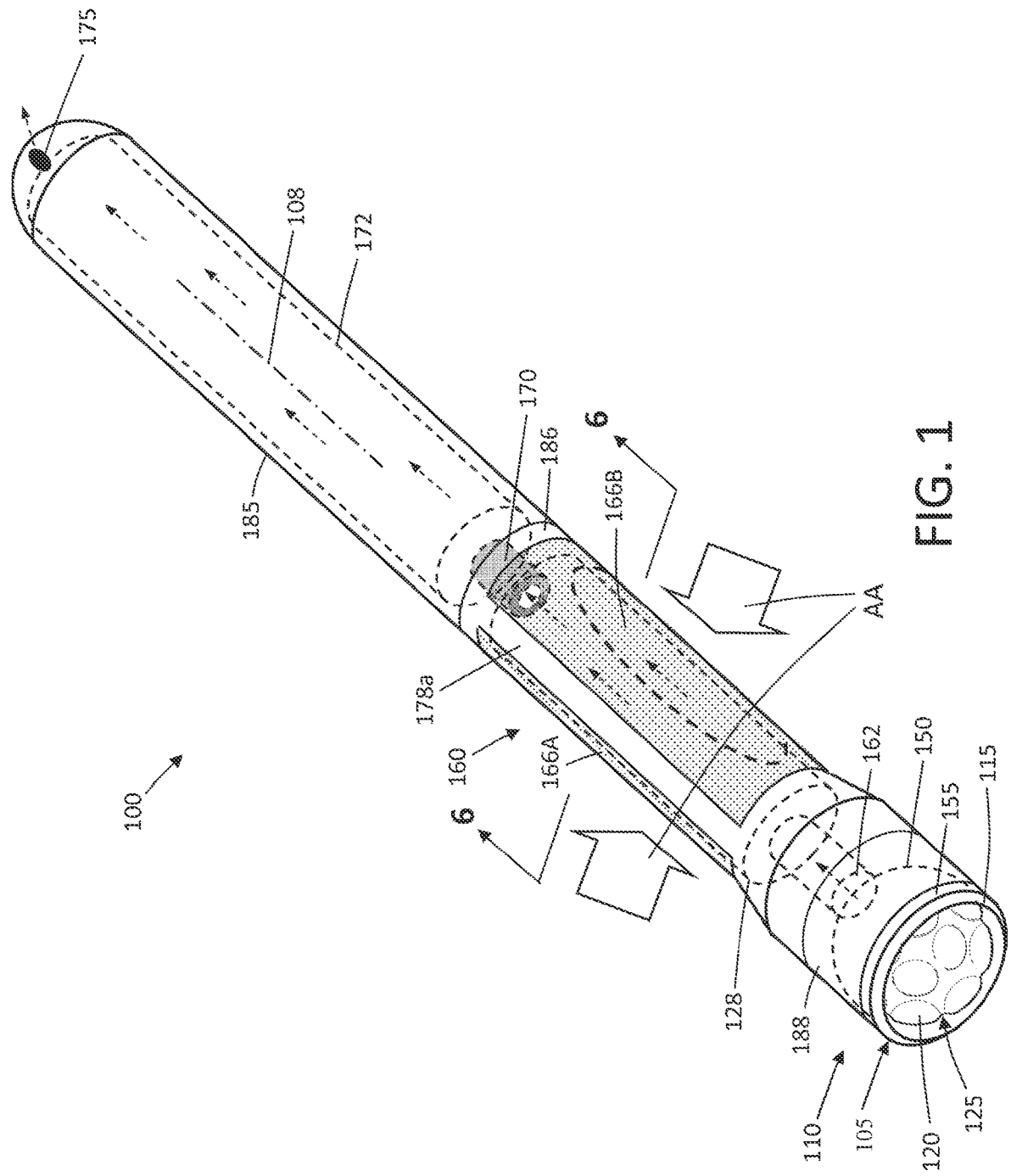
FIG. 1 is a perspective view of an embodiment of a treatment device or applicator corresponding to the invention adapted for enhancing fluid absorption by a subject's lips or skin, where a distal applicator tip includes a rolling member surrounded by a peripheral tissue-contacting element.

FIGS. 1, 3, and 5A-5B illustrate systems for treating tissue, such as skin or lips, which comprise a hand-held treatment device or applicator 100 with a distal applicator tip 105 that is adapted for applying transient negative pressure to a skin surface to enhance fluid absorption and penetration into surface layers of a treatment site in a subject's skin or lips. The device or applicator 100 has a shaft or applicator body 106 extending about longitudinal axis 108 that is gripped with a subject's fingers for movement over a treatment site. The distal applicator tip or roller tip 105 defines a skin interface where the applicator body 106 has a distal housing 110 with a distal periphery 115 that surrounds or is adjacent to an exposed portion of a rolling member 120. As will be described below, the distal periphery 115 is configured to provide a seal against a tissue surface for the purpose of containing negative pressure around the rolling member 120 when in contact with a targeted treatment site.

As background, roller ball devices are well known in the art for applying cosmetic fluids, deodorants, and the like to skin with a spherical roller ball that carries fluid from an interior chamber of an applicator to a skin surface as the roller ball contacts and rolls over a treatment site. As an example, FIG. 2 illustrates a typical prior art cosmetics roller ball as shown in U.S. Pat. No. 8,939,669 issued Jan. 27, 2015, to Son Q. Le et al., titled "Roller-Ball Applicator Assembly for Topical Oils Application" (see FIG. 1b in '669 with original reference numerals removed for convenience). As can be seen in FIG. 2, an important aspect of such prior art roller ball devices can be understood wherein the roller ball has a diameter D and the axial dimension A of the "exposed surface" (in sectional view) of the roller ball extends well beyond the distal tip of the device housing H and is a substantial fraction of the roller ball diameter D (referents D, A and H added by the author to the prior art figure). The large dimension A of the "exposed surface" of the roller ball is important for carrying fluids and applying such fluids to a subject's skin. In such cosmetic roller ball applicators, the "exposed surface" dimension A, as shown in FIG. 2, typically ranges from 25% to 40% of the roller ball diameter D. In such a prior art roller ball devices, the roller is exposed to an interior chamber of the assembly that carries a treatment liquid. Such a liquid interfaces with a surface of a rotating roller ball and can apply a film of the liquid to a subject's skin. As will be described below, the present invention differs entirely in that (i) there is no liquid contained in a chamber or channel that interfaces with the roller ball, and thus (ii) there is no liquid delivered by the roller ball to a subject's skin. In contrast, the present invention has an interior channel that interfaces with the rolling member, where such an interior channel communicates with a negative pressure source to suction or aspirate fluid around or through the rolling member into such an interior channel. This system allows the rolling member to be configured for skin manipulation rather than liquid delivery to a skin surface.

Figure 2:
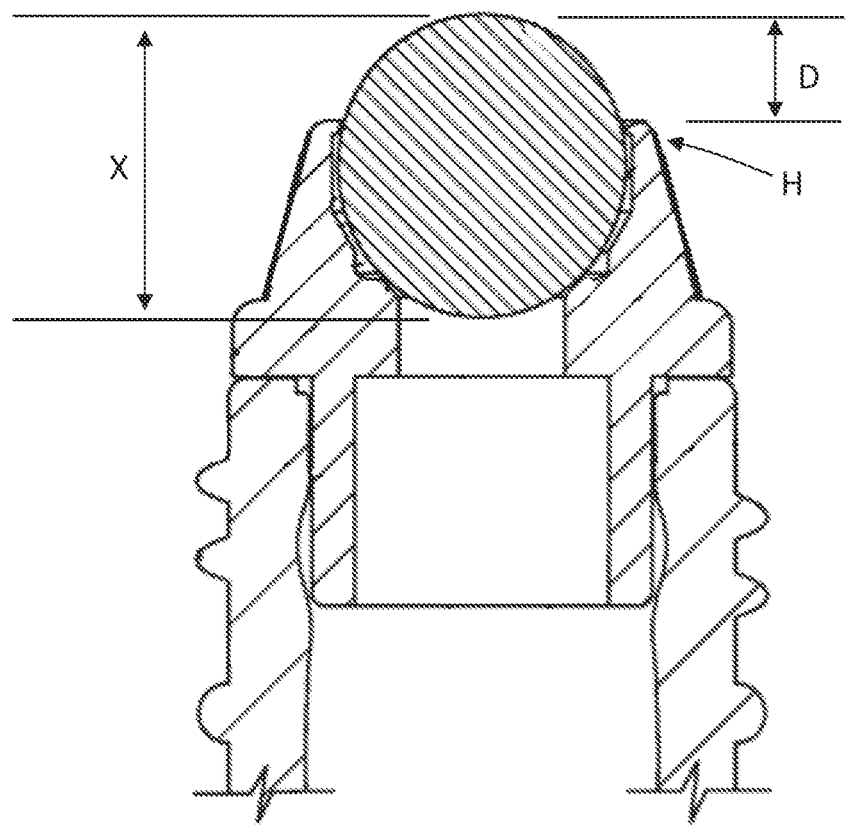
FIG. 2 is a sectional view of a prior art cosmetic roller ball device.
Figure 3:
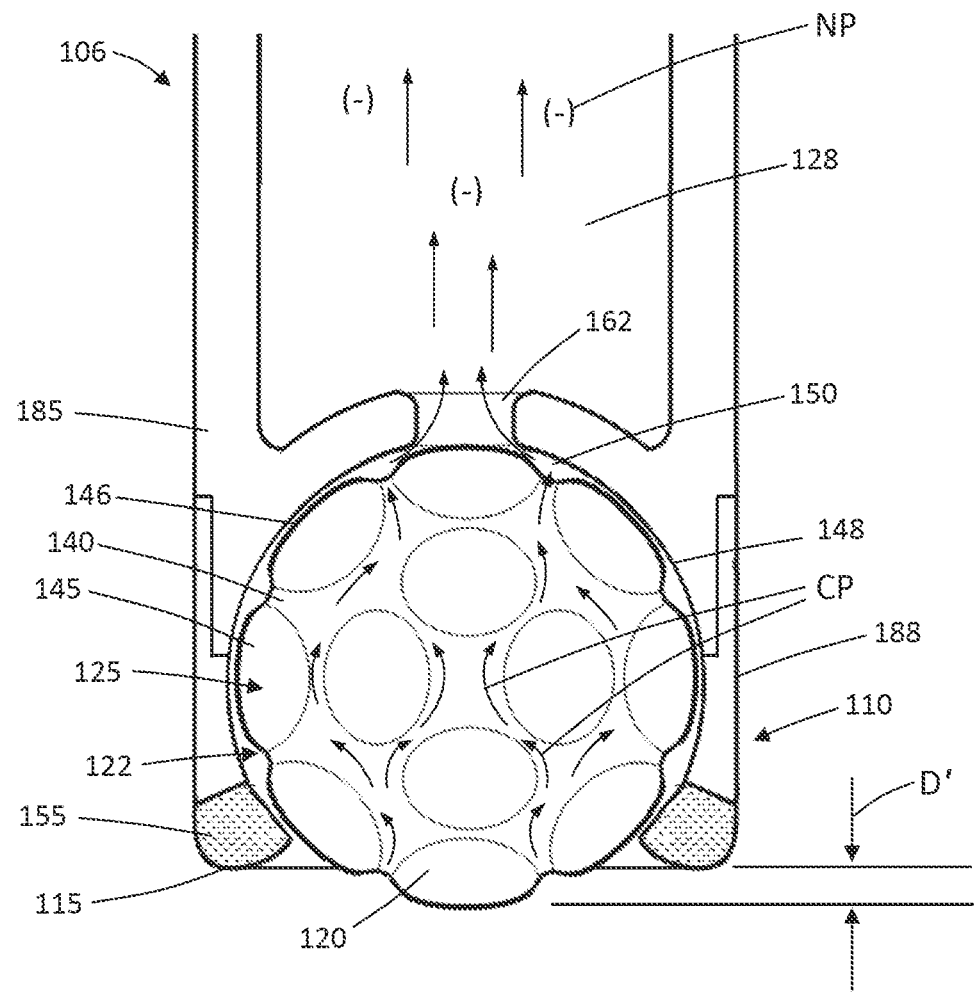
FIG. 3 is an enlarged cut-away view of the applicator tip of FIG. 1 showing the rolling member with discontinuities in the surface thereof for manipulating engaged tissue and for causing a circuitous path of fluid flows over a tissue surface when the rolling member is in contact with tissue.

Now turning to FIG. 3, a distal applicator tip 105 of the present invention is shown. As can be seen in FIG. 3, the applicator tip 105 carries a rolling member 120 in housing 110 that has a function that is entirely different from that of prior art cosmetic roller ball devices as in FIG. 2. In FIG. 3, the distal roller tip 105 is configured to apply negative pressure to a tissue surface—not a fluid. The fluid absorption aspect of the invention is a resulting effect of the negative pressure delivered to, and contained within, the distal applicator tip 105 when engaging a tissue surface. In the variation shown in FIG. 3, the rolling member 120 is not configured to contact and deliver fluid from an interior channel 128 of the device. The function of the rolling member 120 is to manipulate tissue in contact with the rolling member 120, which thereby allows fluid absorption and penetration into the tissue surface. The term tissue manipulation as used herein describes the effects of the rolling surface 122 of rolling member 120 that is configured with surface discontinuities 125 that engage tissue, where the effects can be described as, or include, stretching or tensioning tissue, compressing tissue, piercing tissue, indenting tissue or otherwise transiently modifying tissue from its natural state to a manipulated state as the surface discontinuities 125 of rolling member 120 engage the tissue surface under negative pressure to thereby transiently and locally increase the permeability of the skin surface layer. Of particular interest, the rolling member 120 thus is adapted to create the desired tissue manipulation effects in a friction-free manner as the rolling surface 122 and surface discontinuities 125 roll over a tissue surface.

Referring again to FIG. 3, the enlarged view of the rolling member 120 shows a rolling surface 122 that is not smooth but is configured with surface discontinuities 125 that comprise first and second surface portions where the second surface consists of recessed portions or channels 140 around the first surface portion consisting of projecting portions 145. The recessed portions 140 provide a flow path for negative pressure NP in interior channel 128 to flow around the surface 122 of the rolling member 120. As will be described below, the negative pressure NP when in sealed contact with the patient's lips or skin, can cause transient negative pressure within the engaged tissue to assist in rapid absorption or penetration of a fluid media into the engaged tissue. In the variation shown in FIG. 3, the rolling member 120 has a plurality of projecting portions 145 that may number from 10 to 1,000 or more, where the outermost surfaces 146 of the projecting portions 145 define a spherical rotational envelope. Such outermost surface 146 rollably contacts the surface 148 of the receiving space 150 in the distal housing 110 of the applicator tip 105 that receives the rolling member 120. The term "spherical rotational envelope," as used herein, describes the envelope in which the rolling member 120 contacts if it were rotated in all possible directions. As can be understood from FIG. 3, the number of projecting portions 145 is of a sufficient number to ensure that the rolling member 120 rolls or rotates smoothly in the receiving space 150. Typically, the first surface portion consisting of projecting portions 145 has a surface area of at least 40% of the total surface area of the spherical rotational envelope of the rolling member 120. Further, the second surface portion consisting of the recessed portions 140 has a surface area of at least 10% of the total surface area of the spherical rotational envelope of the rolling member 120.

Still referring to FIG. 3, the surface discontinuities 125 are shown as channels, but other features can provide suitable flow pathways and fall within the scope of the invention, which includes notches, facets, recesses, grooves, partial bores, through-bores, and porosities. Further, the projecting portions 145 may have outermost surfaces 146 that vary within a rolling member 120, for example, with some outermost surfaces 146 being flatter to allow smooth rotation and other outermost surfaces 146 having a sharp apex or a needle-like tip to penetrate tissue or to indent and stretch a tissue surface. As can be understood from FIG. 3, in one variation, the recessed portions or channels 140 are interconnected to thus provide circuitous pathways CP for aspirated fluid flows about the surface of the rolling member 120. Thus, when the rolling member 120 is in contact with tissue, a fluid treatment media under such negative pressure is drawn through the circuitous pathways CP to thereby cause such a fluid media to remain in contact with the tissue surface for a longer interval compared to a non-circuitous pathway. Thus, the surface discontinuities 125 are specifically configured to manipulate the tissue surface and provide a circuitous flow pathway, where the tissue manipulation can consist of stretching, indenting or tensioning tissue, compressing tissue, and piercing or penetrating tissue. At the same time, as will be described below, the negative pressure at the tissue surface can cause transient negative pressure in subsurface tissue to cause the rapid absorption and penetration of the fluid media into the engaged tissue.

Still referring to FIG. 3, in a variation, the distal housing 110 of applicator body 106 has a distal peripheral element 155 that defines the distal periphery 115, where the peripheral element 155 comprises a lubricious material such as Teflon or a resilient material such as silicone, or a combination of lubricious and resilient materials, suited for providing a seal against tissue as the distal periphery 115 and rolling member 120 are translated over a tissue surface to thereby contain negative pressure in the interface of the tissue and the distal applicator tip 105.

In FIG. 3, it also can be seen that the housing 110 of the present invention differs from a typical cosmetic roller ball device as in the prior art device of FIG. 2. In FIG. 3, the exposed portion of rolling member 120 extends distally beyond distal periphery 115 of the housing 110 a dimension D', which is much smaller than dimension D in the prior art device of FIG. 2. In FIG. 3, the exposed portion of rolling member 120 extends distally from distal periphery 115 less than 25% of the diameter of the rolling member 120 and often less than 20% of the diameter of the rolling member 120. In a variation, the exposed portion of rolling member 120 extends distally from distal periphery 115 less than 10% of the diameter of the rolling member 120. It can be understood that dimension D' is important so that the surface 122 of the rolling member 120 and discontinuities 125 therein contact and manipulate tissue while the distal periphery 115 contacts and provides a seal to capture the negative pressure about the skin surface and cause negative pressure in subsurface tissue as will be described further below. In another aspect, the exposed surface of the rolling member 120 extends distally from distal periphery 115 less than 5 mm and often is less than 3 mm.

Figure 4:
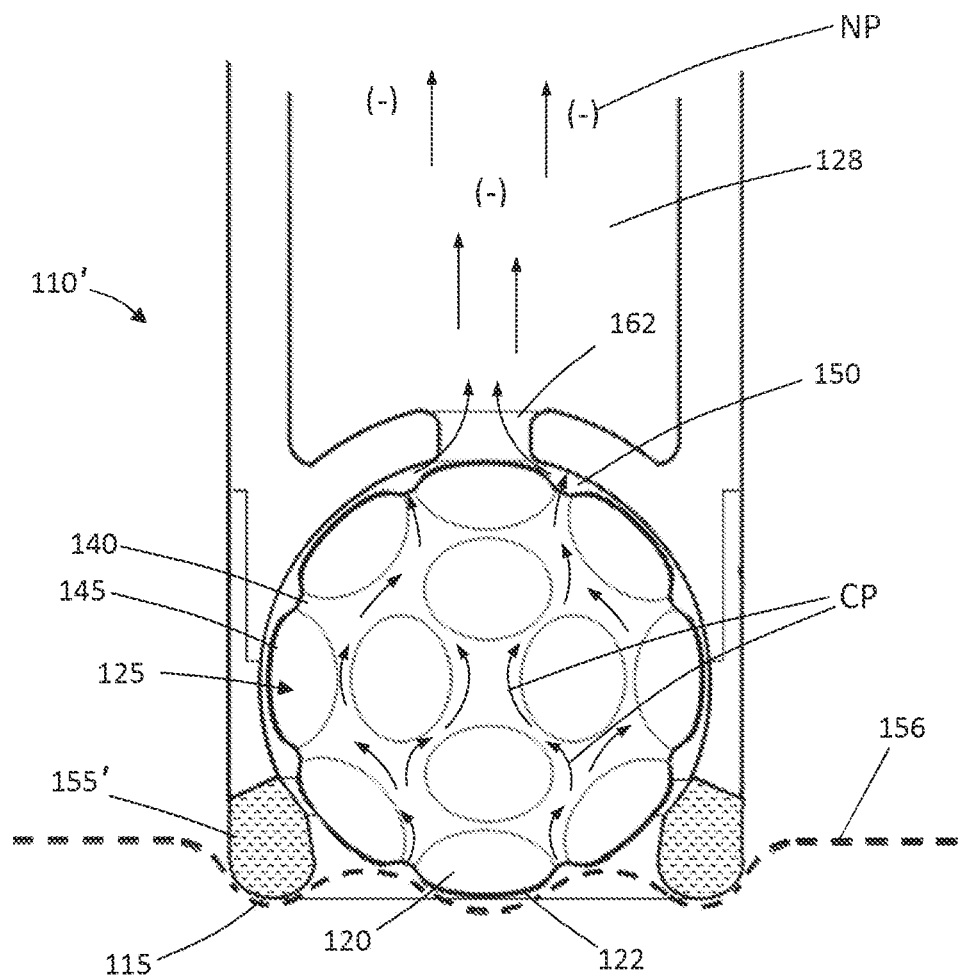
FIG. 4 is a cut-away view of a variation of an applicator tip similar to that of FIG. 3.

FIG. 4 illustrates a variation of a distal applicator tip 110' where the surface 122 of the rolling member 120 does not extend distally beyond the distal periphery 115. In this variation, the peripheral element 155' is extended distally further than the embodiment of FIG. 3. In all other aspects, the components and features of the variations of FIGS. 3 and 4 are the same. In FIG. 4, the tissue surface 156 is shown in phantom view as the distal periphery 115 is pressed into tissue, and negative pressure NP in the interior channel 128 of the distal tip 105 provides negative NP' at the tissue surface 156 captured within the distal periphery 115. The negative pressure NP' then suctions the tissue surface 156 into contact with the surface 122 of the rolling member 120.

Referring to FIGS. 1 and 3, the applicator body 106 can have any suitable dimension about axis 108 and any shape suited for gripping with a human hand or fingers. Typically, the rolling member 120 can have a diameter ranging from 3 mm to 20 mm and often has a diameter ranging from 5 mm to 10 mm. Devices with rolling members 120 having a smaller diameter are suited for treating lips, and larger rolling members are suited for treating facial skin or other skin surfaces. The components of the applicator 100 can be understood from FIGS. 1 and 3, and the body 106 is fabricated of molded plastic, metal, a combination of plastic and metal, or other suitable materials. The body 106 can be a combination of single-use or limited-use components together with non-disposable components. In a variation, the applicator body 106 can be a transparent or translucent plastic material which allows for viewing of the interior thereof during use.

Figure 5A:
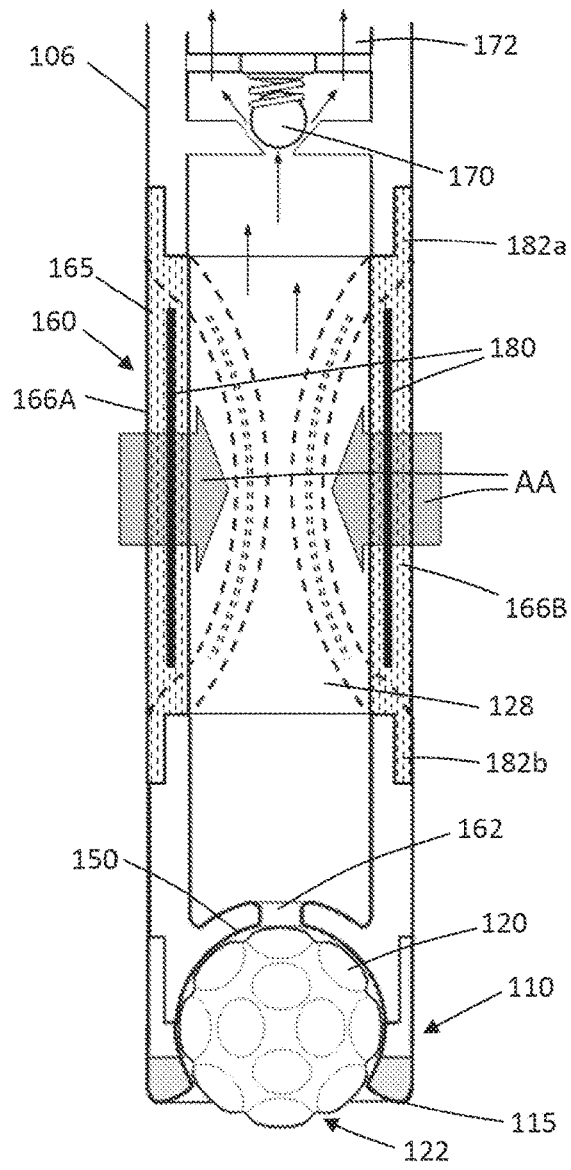
FIG. 5A is a sectional view of portion of the applicator body of the device of FIG. 1 showing a squeeze bulb component of the device in a first repose position, where the squeeze bulb is adapted to provide negative pressure in an interior channel of the device.
Figure 5B:
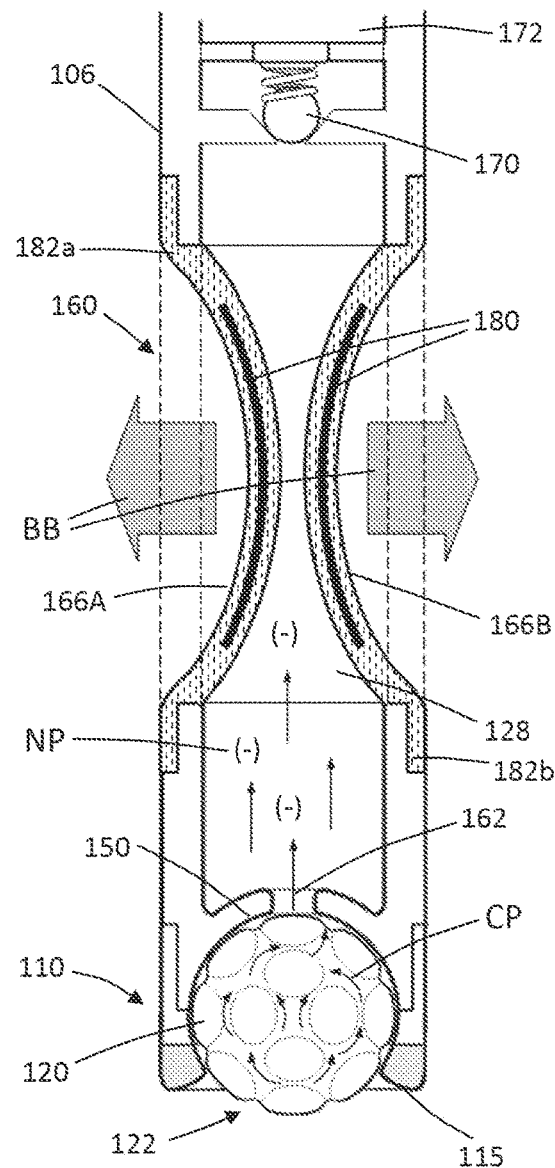
FIG. 5B is a sectional view of the applicator of FIG. 5A showing the squeeze bulb component in a second compressed and tensioned position, where the squeeze bulb, when released from compression, provides negative pressure in the interior channel of the device.
Figures 6, 7:
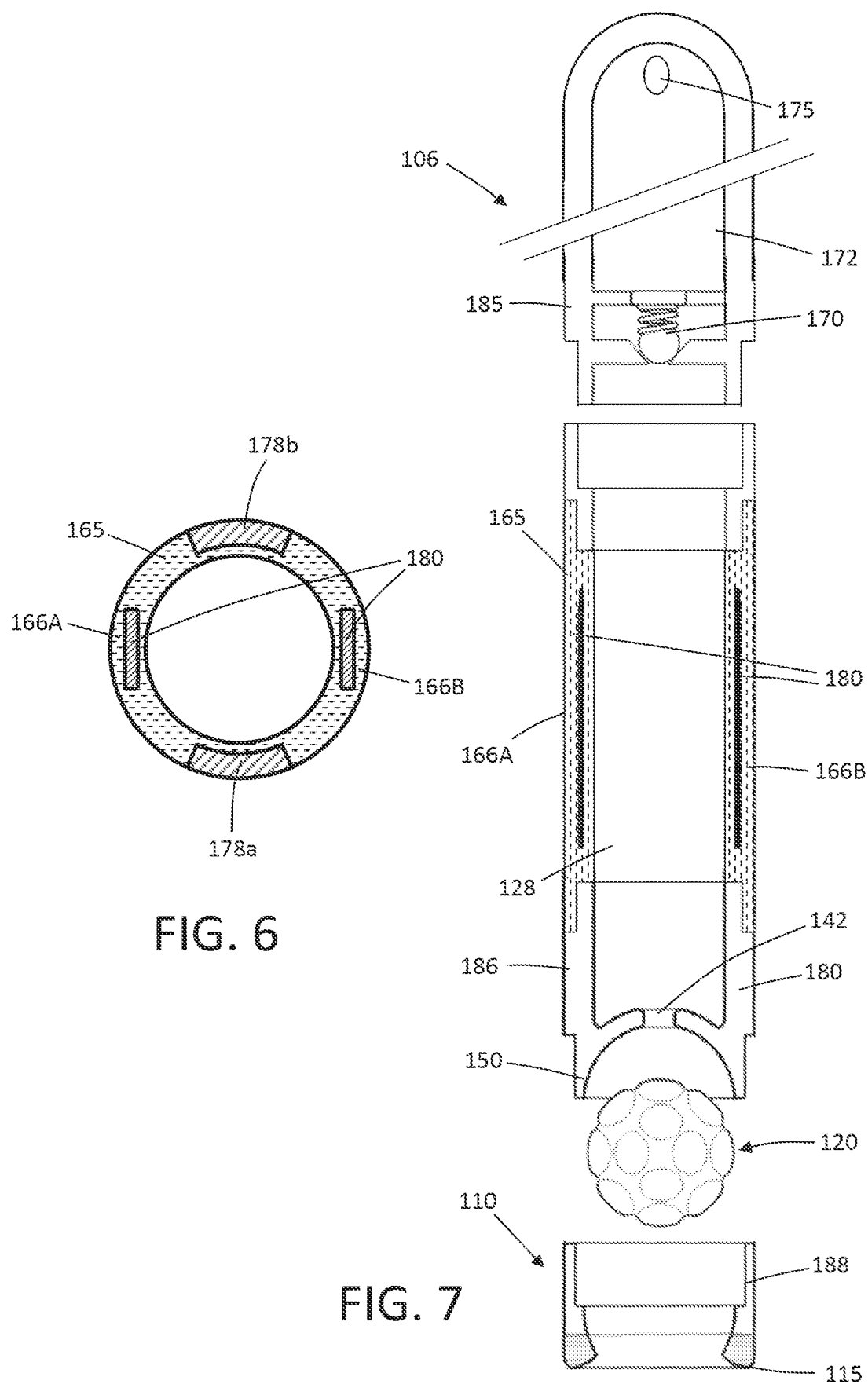
FIG. 6 is a sectional view of the applicator body taken along section 6-6 of FIG. 1.
FIG. 7 is an exploded view of the components of the device of FIG. 1, showing the various components de-mated from one another to allow for cleaning or replacement.

Referring now to FIGS. 1, 3, and 5A-5B, it can be seen that the applicator 100 includes a manually actuated negative pressure mechanism 160 in an interior aspiration chamber or channel 128 of the applicator 100 where the channel 128 has a distal end 162 that interfaces with the receiving space 150 around the rolling member 120 to apply negative pressure or suction around the rolling member 120 and to the targeted treatment site. In the applicator 100, as shown in FIGS. 1, 5A, and 5B, the negative pressure mechanism 160 comprises an elastomeric squeeze bulb 165 where first and second sides 166A and 166B of the squeeze-bulb 165 are adapted to be pressed inwardly toward axis 108, which then causes air in the interior channel 128 to exit the channel 128 in the proximal direction through one-way valve 170 and thereafter through exit channel 172 in the proximal portion of the body to exit port 175 in the applicator body 106 (see FIGS. 1 and 7). As can be seen in FIGS. 1 and 6, the device body 106 has axial beam portions 178a and 178b that extend longitudinally as a support for the body 106 about the elastomeric squeeze bulb 165. In a variation, the squeeze bulb 165 has longitudinal leaf springs 180 molded into its elastomeric walls to urge the squeeze bulb 165 to the non-collapsed, linear shape as shown in FIGS. 1 and 5A. The proximal and distal ends (182a, 182b) of the elastomeric squeeze bulb 165 are bonded to the adjacent sections of the tubular body 106 to provide a sealed interior channel 128 (FIG. 5A).

In the variation shown in FIGS. 5A and 5B, a single leaf spring 180 is shown on each side of the squeeze bulb 165, but it should be appreciated that a plurality of spring elements can be used on each side 166A and 166B of the squeeze bulb. Alternatively, the spring elements may be disposed in the interior channel 128 and not fully embedded in the wall of the elastomeric squeeze bulb 165. In such an alternative, such leaf springs would then have a proximal and distal end that are fixed to the device body 106. It should be appreciated that other forms of spring elements may be used in a squeeze bulb structure, such as collapsible-expandable braided structures, helical springs, zig-zag springs, and the like. In a variation, the elastomer of the squeeze bulb 165 can be a transparent or translucent material to allow viewing of the interior thereof during use.

FIGS. 5A and 5B illustrate a method of operating the negative pressure mechanism 160. In FIG. 5A, the first and second sides 166A and 166B of squeeze-bulb 165 are pressed inwardly (see arrows AA), which tensions the elastomeric walls and springs 180 therein (phantom view in FIG. 5A) to displace the air in the interior channel 128. FIG. 5B then shows the squeeze bulb 165 in a tensioned, compressed shape which is being urged outwardly in the direction of arrows BB that, thereby creates negative pressure NP in the interior channel 128. The negative pressure NP in the interior channel 128 then communicates with the interface with receiving space 150 of rolling member 120. The negative pressure NP thus provides suction forces around the rolling member 120 to communicate with a surface of a treatment site engaged by applicator tip 105 and the exposed portion of the rolling member 120. In this variation, the negative pressure in interior channel 128 is created as air is pumped outwardly through channel 172 and exit port 175 faster than air flows inwardly around the rolling member, and negative pressure is maintained in interior channel 128 after the distal tip 105 is pressed against tissue and the negative pressure mechanism 160 is further actuated during use. In another variation described below, a normally closed finger-actuated valve is provided in the distal end 162 to prevent air flow around the rolling member 120 to maintain negative pressure in the interior channel 128 after actuation of the negative pressure mechanism 160.

Now turning to FIG. 7, an exploded view of the applicator 100 of FIG. 1 illustrates that the components of applicator body 106 can be mated and de-mated to allow for cleaning or replacement of the component parts. In a variation, the body 106 has a first proximal body portion 185 that is separable from the central body portion 186 that carries the squeeze-bulb 165 to allow cleaning of the interior thereof. The proximal portion 185 of body 106 has the function of carrying the check valve or one-way valve 170 and an exit channel 172 to exit port 175 and can comprise one or more elements that may be separable to allow for cleaning the interior thereof. In other variations, the one-way valve 170 can consist of a flap valve, a duck-bill valve, or any form of simple elastomeric check valve. Such a one-way valve can be disposed either in the interior of the body, as in FIG. 7 or the valve can be disposed at the proximal end of the device and comprise a feature of the exit port 175. As can be seen in FIG. 7. the first central body portion 186 can be decoupled from the distal body portion 188 to allow cleaning thereof and cleaning or replacement of the roller member 120. The various components are shown in FIG. 7 with cylindrical mating features having a suitable slip fit that may be adequate to maintain negative pressure in interior channel 128 and other components of the device. In another variation, the mating connections may be provided with o-rings to enhance sealing between the components. In FIG. 7, the body portions 186 and 188 separate axially, but any other form of structure can be used in a side-to-side or other arrangement to allow assembly of the members to provide the spherical receiving space 150 for receiving and capturing the rolling member 120.

Figure 8D:
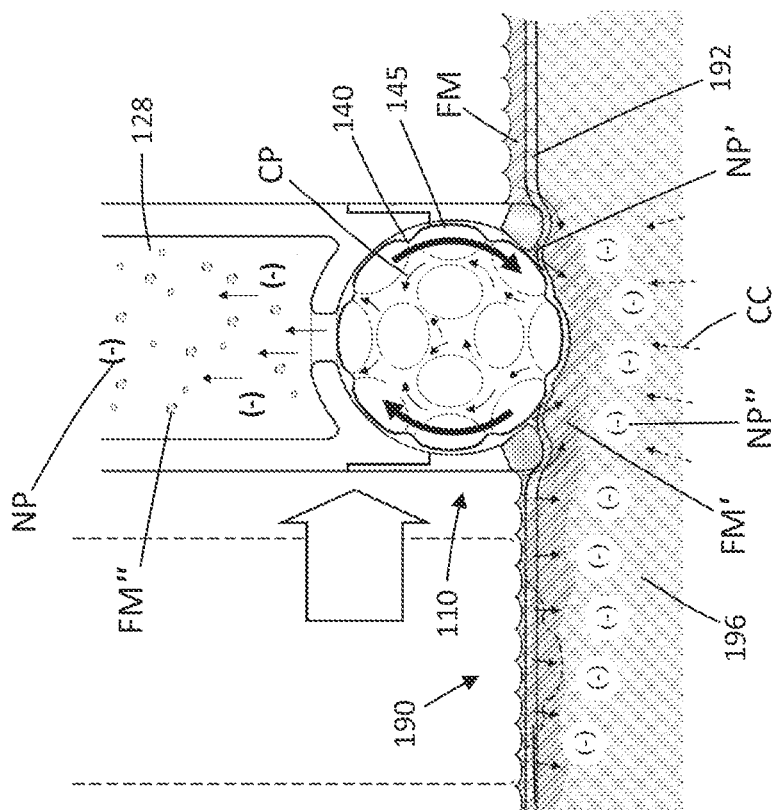
FIG. 8D illustrates a subsequent step where the applicator tip is translated across the tissue surface, which continues to apply negative pressure about the rolling member that causes negative pressure in subsurface tissues, which in turn causes absorption and penetration of the treatment media into the tissue.

FIG. 8A through 8D illustrate a method of using the applicator 100 of FIGS. 1, 3, and 5A-5B to treat a subject's lips 190. In FIG. 8A, the subject has topically applied flowable treatment media FM to the treatment site. It should be appreciated that the flowable or fluid media FM can consist of a liquid, gel, or flowable media that can contain medications, serums, nourishing agents, botanicals, plumping agents, vitamins, colorings, cosmetics, peeling agents, de-sensitizers, hormones and any other flowable media known in the art for topical use. The operator of the applicator 100 then actuates the sides 166A and 166B of the squeeze bulb 165 (indicated by arrows AA) to thereby create negative pressure NP in the interior channel 128 of the device. FIG. 8B is an enlarged schematic view of the applicator tip 105 and rolling member 120, as in FIG. 8A just prior to being pressed into contact with the subject's lips 190, where the fluid media FM is shown on the tissue surface 156. In FIG. 8B, it can be seen that a negative pressure NP is provided in the interior channel 128 that communicates with the receiving space 150 around the spherical rolling member 120.

Figure 8C:
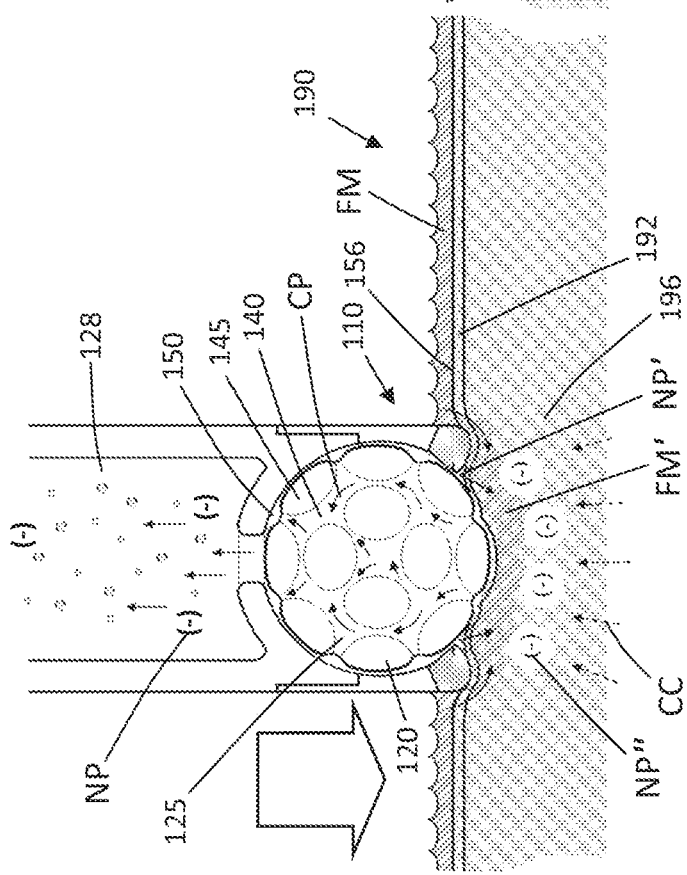
FIG. 8C illustrates a subsequent step of the method where applicator tip is pressed into contact with the tissue surface, which applies negative pressure about the rolling member and to the tissue surface as well as causing negative pressure within subsurface tissue to further cause absorption of the treatment media.

FIG. 8C illustrates a subsequent step of the method wherein the distal periphery 115 of the applicator body 106 and rolling member 120 are pressed into the tissue surface 156 and where negative pressure NP in the interior channel 128 communicates with the receiving space 150 and discontinuities 125 in the surface of the rolling member 120 to cause negative pressure NP' at the tissue surface 156. The irregularities of recessed portions 140 and projecting portions 145 in the roller surface 122 (see FIG. 3) causes the surface layer of the tissue to be stretched, indented, and tensioned (i.e., manipulated) as well as being exposed to negative pressure NP'. This negative pressure NP' at the tissue surface 156 can cause a transient negative pressure NP''' to migrate through the surface tissue layer 192 to a subsurface tissue 196, which will cause upward migration of intracellular fluids towards the tissue surface 156 as indicated by arrows CC (and potentially a bruise as capillaries may be damaged). The negative pressure NP''' in subsurface tissue 196, more importantly further causes fluid media FM at the tissue surface 156 about the spherical rolling member 120 to penetrate inwardly toward the negative pressure NP''' in the subsurface tissue 196. Thus, the subsurface negative pressure NP''' causes absorbed fluid media indicated at FM' in FIG. 8C. Further, the circuitous path CP of the fluid media FM within the discontinuities 125 (see FIG. 3) of the spherical rolling member 120 causes the fluid media FM to migrate over the tissue surface 156 to maintain fluid contact with the manipulated or affected (i.e., stretched, penetrated) tissue. All of these effects cause the fluid media FM to the absorbed by and penetrate into subsurface tissue 196 indicated at FM'.

FIG. 8D shows the applicator tip 105, distal periphery 115, and rolling member 120 being translated across the tissue surface 156, which rolls the rolling member 120 and transiently creates negative pressure NP''' over a larger expanse of subsurface tissue 196 to cause absorption of fluid media FM' over the treated region. At the same time, small amounts of the fluid media FM'' are aspirated into the interior channel 128 in response to negative pressure NP therein.

In general, a method of the invention for treating a subject's skin or lips comprises contacting a tissue surface with a rolling member carried at a distal end of an applicator body, moving the rolling member over the tissue surface, and creating negative pressure about the rolling member in contact with the tissue surface to transiently cause negative pressure in subsurface tissue to enhance permeability of the tissue surface. Typically, the treatment media is applied topically to the subject's skin or lips before the use of the negative pressure applicator. During use, the translation of the applicator tip over a tissue surface causes the surface discontinuities of the rolling member to compress, stretch, tension, and/or pierce the tissue surface to enhance penetration or absorption of the treatment media.

As a negative pressure in the interior channel 128 of the device is reduced during use, the operator can intermittently or continuously actuate the squeeze bulb 165 to increase or maintain negative pressure NP in the interior channel 128 while translating the applicator tip 105 and rolling member 120 across the tissue surface 156. All of these effects combine to enhance fluid absorption and penetration. Following use, the operator can disassemble the applicator 100 as shown in the exploded view of FIG. 7 and clean the interior channel 128 and other components, for example, with running water. The device components may then be reassembled for future use.

The variation of FIGS. 1, 3, 5A, and 5B illustrate the squeeze bulb 165 as a form of pump that is suitable for creating negative pressure in interior channel 128 of the applicator 100, but it should be appreciated that any type of manually actuated pump may be used and fall within the scope of the invention. Typically, a positive displacement pump is suitable, which can be a piston pump, a syringe pump, bellows pumps, a peristaltic pump, a gear pump, an impeller pump, a vane pump, or a diaphragm pump.

FIG. 9 illustrates a distal applicator tip 205 of another variation of an applicator that is otherwise similar to that of FIGS. 1 and 3. In FIG. 9, the rolling member 120' is similar to that of FIG. 3 with similar projecting portions 145. In this variation, the recessed portions 140' have an abrasive surface 210 which, for example, can be diamond dust adhered thereto or sharp abrasive edges molded into a plastic rolling member. The abrasive surface 210 provides for traction between the rolling member 120' and the skin surface 156 as well as causing micro-penetrations into the skin surface 156 as a form of tissue manipulation to thereby enhance penetration of fluid treatment media into the skin as described previously. In this variation, the distal periphery 115' is shown to extend distally compared to that of FIG. 3 such that the surface 122' of the rolling member 120' does not extend beyond the distal periphery 115'. In such an embodiment, where the rolling member surface 122' is somewhat recessed in the tip 205, it is useful to provide increased traction between the rolling member 120' and a skin surface. As can be understood in FIG. 9, the abrasive surface 210 is recessed relative to the outermost surfaces of the projecting portions 145 so that the rolling member 120' rolls smoothly in the receiving space 150.

FIG. 10 illustrates another variation of distal applicator tip 215 that is similar to previous embodiments, except the rolling member 220 has projecting portions 225 surrounded by a recessed region 240 that carries a plurality of sharp elements that can be micro-needles 244 or molded sharp points that provide for traction between the rolling member 220 and the tissue surface 156 as well for penetrating the skin surface 156 as a form of tissue manipulation to thereby enhance penetration of fluid media into the skin. In FIG. 10, a limited number of micro-needles, 244 are shown, but the number may range from dozens to many hundreds of such micro-needles. In the variation of FIG. 10, the distal peripheral element 255 that surrounds the exposed portion of the rolling member 220 is shown of a resilient elastomeric material with an annular void 256 therein to allow the element to be flexed and compressed when in contact with tissue to create an effective seal. The distal end 258 of the housing is configured to prevent the peripheral element 255 from being flexed into contact with the rolling member 220.

Figure 11:
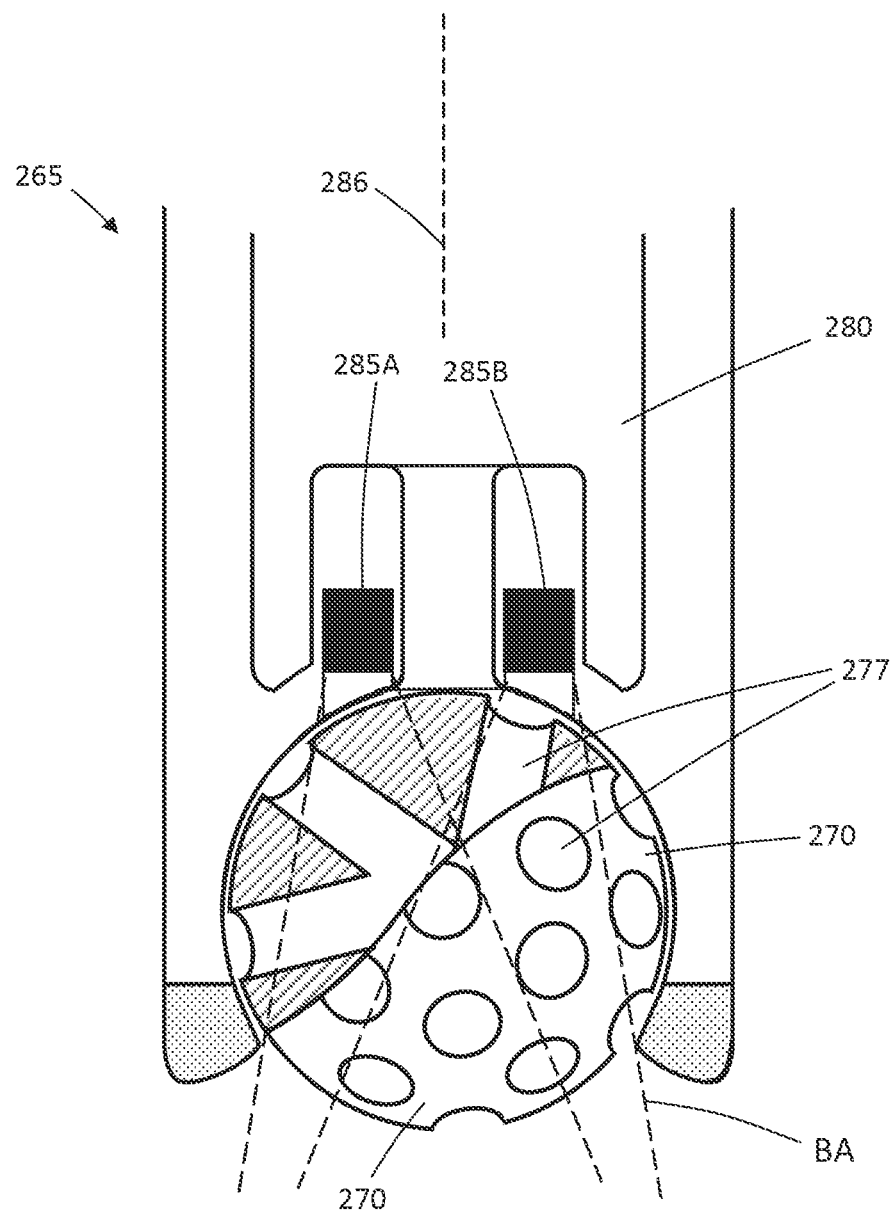
FIG. 11 is a cut-away view of another variation of applicator tip similar to that of FIG. 1, where the distal housing carries LEDs for applying light energy to tissue.

FIG. 11 illustrates another variation of distal applicator tip 265 that has a rolling member 270 with outer surface portion 275 and through-channels or bores 277 that function as means for communicating a negative pressure NP in interior channel 280 with tissue in contact with the rolling member 270. The number of bores 277 can range in number from 10 to 100 or more and can be any suitable dimension ranging from 1% of the diameter of the rolling member to 20% of the diameter or rolling member 270. FIG. 11 also illustrates another feature in this variation of applicator tip 265 that comprises at least one LED, and in this variation is shown as two LEDs, 285A and 285B, that emit at least one wavelength of light for treating tissue. In this variation, the rolling member is formed of a transparent material such as a plastic or glass to permit light transmission therethrough. The LED beam angle BA is shown in FIG. 11 and can range from 15° to 60°. In a variation (not shown), the rolling member 270 can carry embedded or surface light shaping diffusers that comprise micro-structures randomly or controllably positioned on or within the rolling member 270 to modify the LED light beam by changing the direction of its energy. Such light-shaping diffusers can shape the light beam(s) to propagate laterally relative to the axis 286 of the applicator tip 265 to broadly treat tissue in contact with the rolling member 270. In the variation of FIG. 11, the LEDs 285A and 285B can emit a red-light wavelength which research indicates can penetrate deep into skin and stimulate the mitochondria, which has an anti-inflammatory and rejuvenating effect. Such red-light therapy has been found to accelerate skin repair, regulate oil production and improve circulation, and is known as a medically approved treatment for rosacea. The LEDs also can emit blue light, which has antibacterial properties for the treatment of acne, eczema, and psoriasis. Other wavelengths also can be used and fall within the scope of the invention. The LEDs 285A and 285B can be coupled to a re-chargeable battery (not shown) carried by the applicator.

Figure 12:
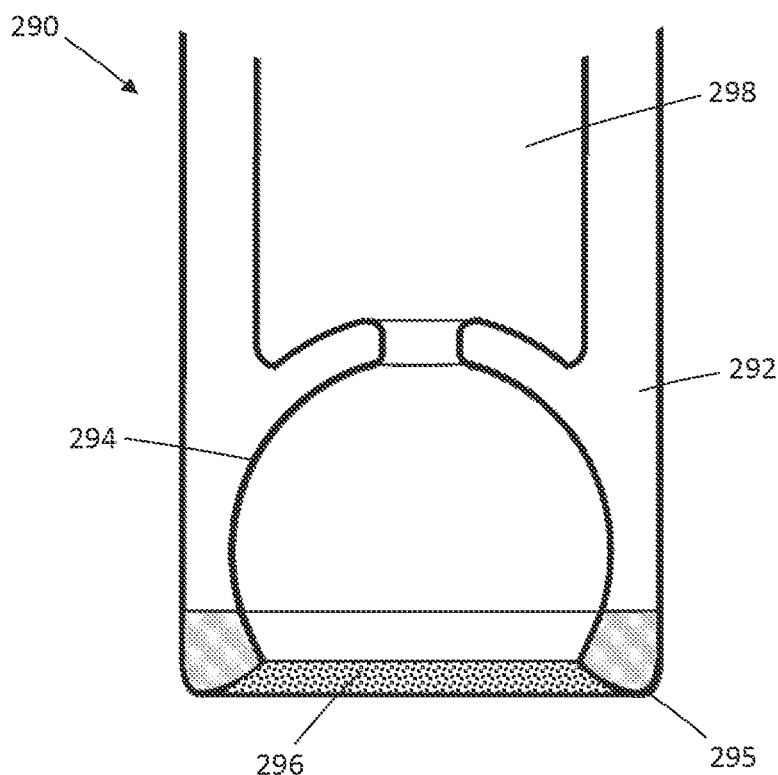
FIG. 12 is a sectional view of another variation of roller housing that is configured with an abrasive surface around a distal periphery of the applicator body for providing a dermabrasion effect to enhance fluid penetration into a skin surface.

FIG. 12 illustrates a variation of an applicator body 290 with a distal housing portion 292 with a receiving space 294 for receiving a rolling member (not shown), where the rolling member can be similar to any previously described embodiments. In this variation, the distal periphery 295 is configured with a portion having an abrasive surface 296 that can consist of abrasive particles such as diamond dust adhered to the distal periphery 295. Alternatively, the abrasive surface 296 can consist of sharp edges and features formed in a molded, machined, printed, or etched material that comprises the distal periphery 295. The abrasive surface 296 functions to abrade and remove a skin surface layer as the distal housing portion 292 and periphery 295 are translated over a tissue surface. Such an abrasive effect enhances fluid penetration into and through the surface tissue layer. In all other aspects, the rolling member and negative pressure in the interior channel function 298 as described previously to perform methods of the invention.

Figure 13:
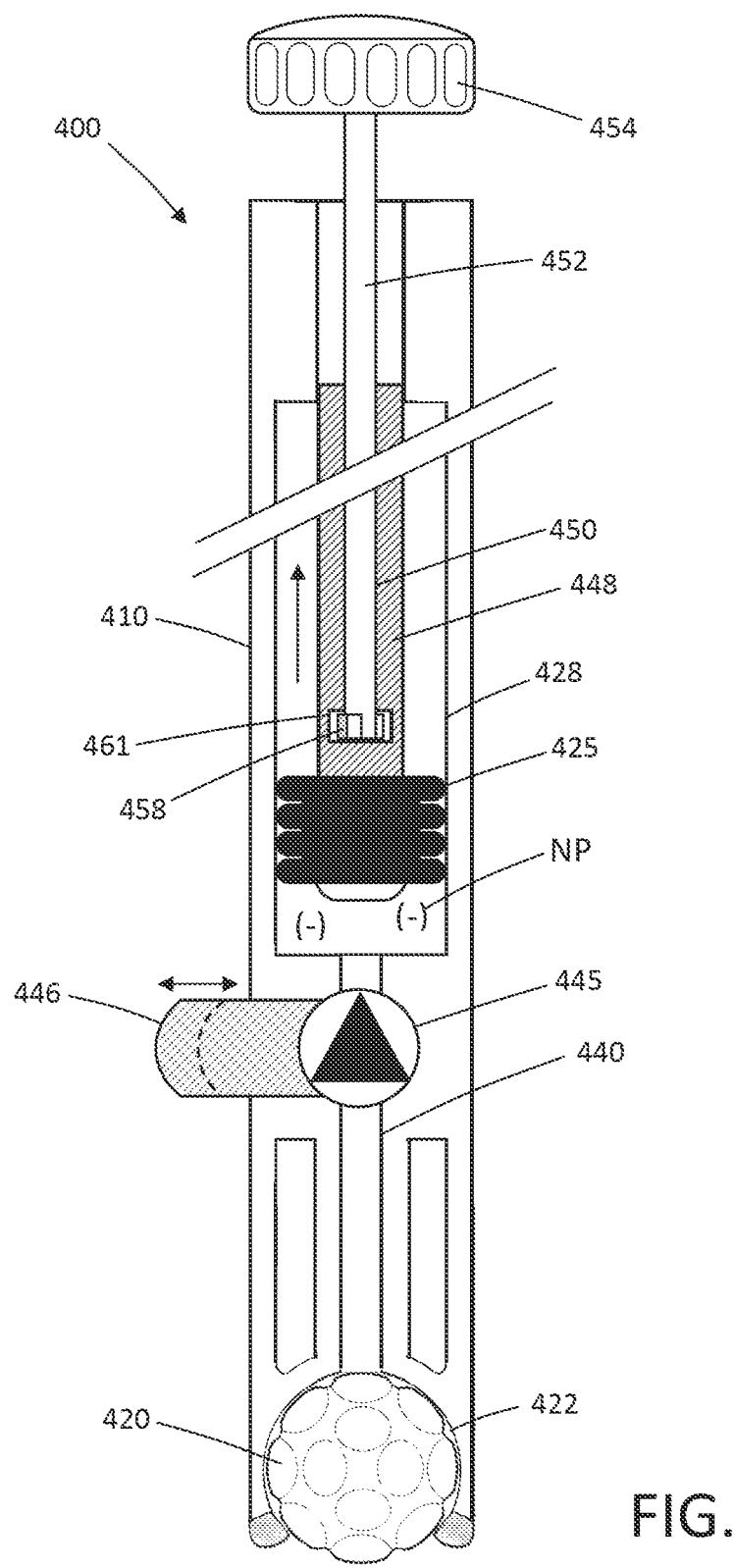
FIG. 13 is a sectional view of another variation of a negative pressure treatment device where negative pressure is created by a syringe-type piston mechanism and where the applicator further includes a finger-actuated valve for releasing aspiration forces to treat tissue.

FIG. 13 illustrates another variation of a treatment device 400 that is similar to that of FIGS. 1, 3, and 4, except that a different negative pressure mechanism 405 is provided in the applicator body 410. In the variation of FIG. 13, the rolling member 420 and the receiving space 422 are the same as described previously. The variation of FIG. 13 is adapted to create negative pressure NP with a syringe-type piston 425 that is movable in an interior syringe chamber 428 to provide negative pressure NP therein. The manually actuated piston 425 and chamber 428 communicate with a flow channel 440 that interfaces with rolling member 420 as described previously. In this variation, a finger-actuated valve 445 with actuator button 446 that has a normally closed position is provided in the flow channel 440 intermediate, the syringe chamber 428, and the rolling member 420. In use, the negative pressure NP can be maintained in the syringe chamber 428 until the operator actuates the valve 445 to apply negative pressure or suction forces to an engaged tissue surface. In one variation, the piston 425 is coupled to an actuator shaft 448 that is moved axially in the proximal direction to create negative pressure NP in the syringe chamber 428. The actuator shaft 448 is shown in FIG. 13 as a tubular member with a bore 450 therein that receives a telescoping member 452 with grip 454. The telescoping member 452 has distal tabs 458 that can be rotated in an offset 461 in bore 450 to engage and disengage the shaft 448 to thus provide an axially collapsible shaft assembly.

Figure 14:
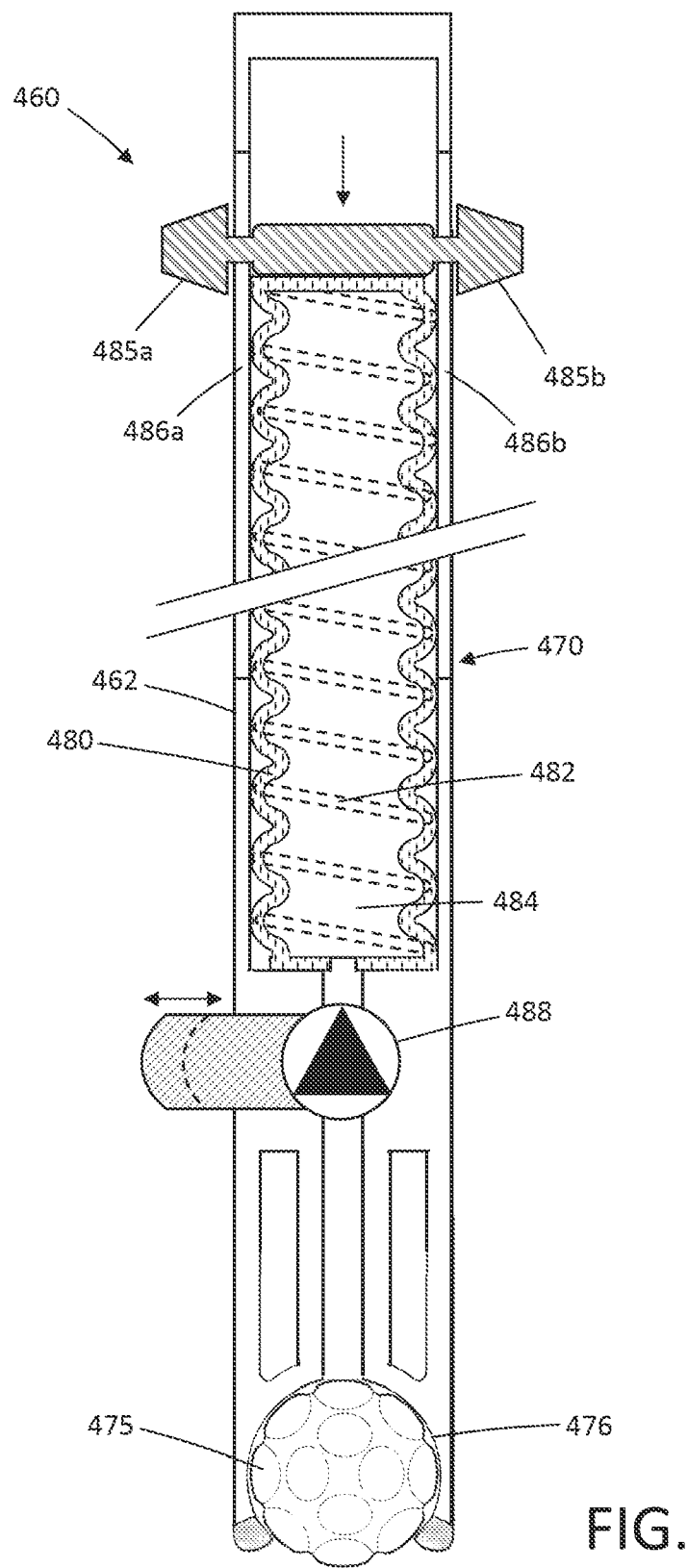
FIG. 14 is a sectional view of yet another variation of a negative pressure treatment device where negative pressure is created by a manually-actuated bladder or bellow mechanism.

FIG. 14 illustrates another variation of a treatment device 460 with an applicator body 462 that is similar to the previous embodiment of FIG. 13, except that it provides a different negative pressure mechanism 470. In the variation of FIG. 14, the rolling member 475 and receiving space 476 are the same as described above. In the variation of FIG. 14, negative pressure is provided by a bladder or bellows 480 that is urged toward an expanded shape by a strong helical spring 482 to create negative pressure in an interior chamber 484 thereof. The bladder 480 is collapsible by finger-actuated tabs 485a and 485b that extend through slots 486a and 486b in the applicator body 462. A finger-actuated valve 488 is provided as in the previous embodiment, where the valve is held in an open position as the bladder 480 is actuated to the collapsed position. In all other aspects, the method of using the device 400 of FIG. 13 is the same as described above.

FIG. 15 illustrates another variation of a distal housing 505 and receiving space 506 of an applicator body 510 shown without a rolling member, where the rolling member can be similar to the previous embodiment of FIGS. 1 and 3 or other embodiments. In this variation, the distal periphery 515 is formed with a series of undulations 518 that is adapted to manipulate a tissue surface similar to the irregular surface of a rolling member. Thus, as the distal housing 505 is translated over a tissue surface, the projecting portions 520 of the undulations will indent, tension, and stretch surface tissue, which can enhance fluid penetration into and through the surface tissue layer. FIG. 15 also shows that the spherical inner surface 522 of the roller receiving space 506 has surface discontinuities or grooves 525 therein that provide a flow path for negative pressure NP in a channel around the rolling member. Thus, there can be features in either or both the surface of the rolling member and the surface 522 of the receiving space that provide flow pathways for negative pressure NP to perform the method of the invention. In this variation, it should be appreciated that a rolling member (not shown) could have an entirely spherical abrasive surface and rotate smoothly in the receiving space 506 since the number of apices of abrasive elements would number in the thousands and the flow pathway for negative pressure to the tissue surface would be provided largely or entirely by the surface discontinuities or grooves 525 and partly by the interstices between the projecting portions of the abrasive elements.

FIG. 16 illustrates another variation of a distal housing 555 and receiving space 556 of an applicator body 560, where the distal periphery 565 of the housing 555 carries a plurality of roller balls 566 which project slightly from the distal periphery 565. Such roller balls 566 can serve the function of manipulating tissue as described above while at the same time reducing friction of the distal housing 555 with the tissue surface as it is translated over a tissue surface.

Figure 17:
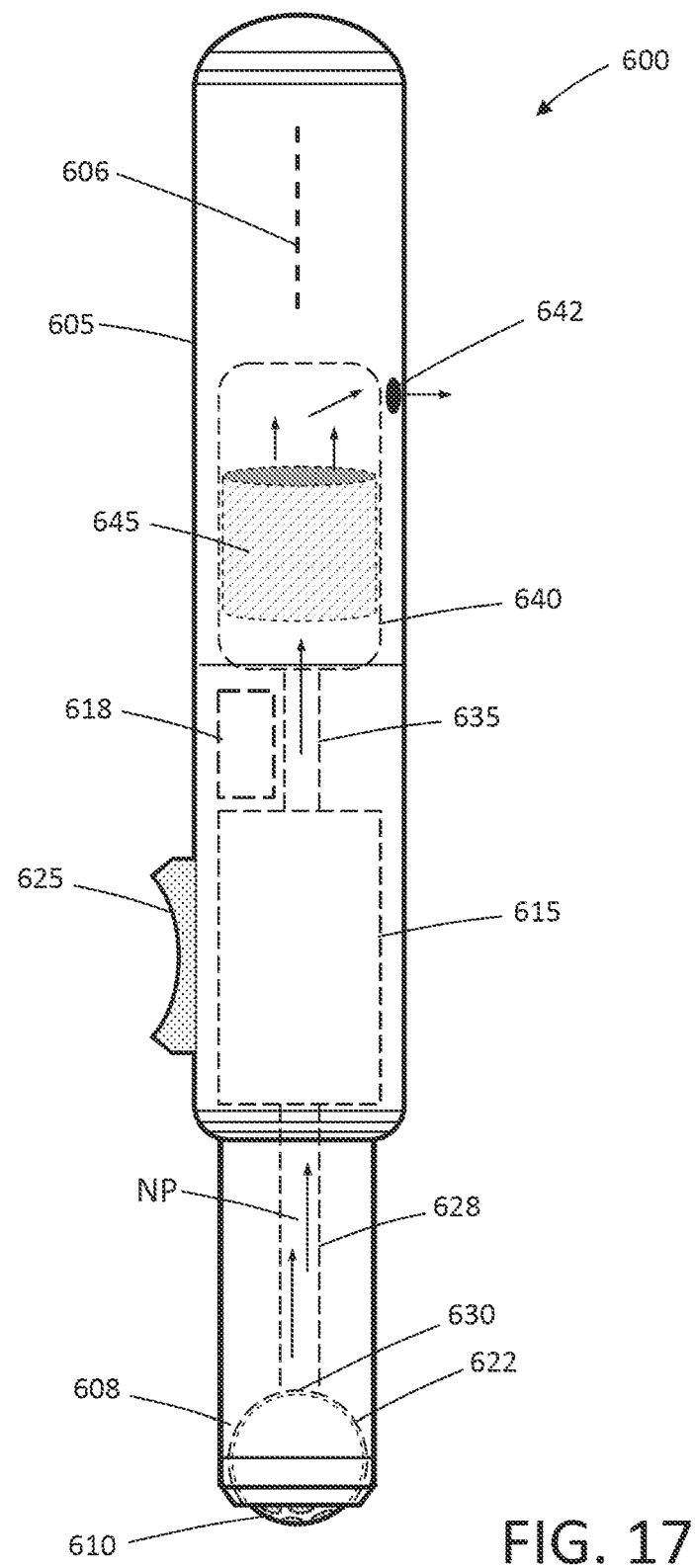
FIG. 17 is an elevational view of another variation of skin treatment device or applicator with a distal rolling member and a DC motor-driven pump assembly with a filter carried in the applicator body.

FIG. 17 illustrates another variation of a treatment device 600 that is similar to that of FIGS. 1, 3, and 4 with an elongate body 605 extending about longitudinal axis 606 and is configured with a distal housing 608 that carries a rolling member 610. In this variation, the negative pressure mechanism comprises a pump assembly 615 that comprises a pump and DC motor powered by a battery 618, both of which are carried in the applicator body 605. This variation is again adapted for use with a topically applied treatment media as described previously. In the variation of FIG. 17, the rolling member 610 is rotatable in any direction in the receiving space 622 of the distal housing 608 and is similar to previous variations. The pump assembly 615 can comprise any suitable form of pump, and in a variation is a diaphragm pump coupled to a 3.7 W DC motor that is operated by rocker switch 625 in the applicator body 605. In one variation, the rocker switch 625 is adapted to select between one or more settings of negative pressure, for example, up to 63 kPa (9.14 psi). The variation of FIG. 17 is adapted to create negative pressure NP in the distal aspiration or extraction channel 628 that interfaces with rolling member 610 about an open termination 630 of the said aspiration channel 628. Thus, the pump assembly 615 aspirates air and fluid droplets through or around the rolling member 610 and through the pump assembly 615 into the proximal aspiration or extraction channel 635, which can include an interior chamber 640 in the applicator body 605. At least one vent or aperture 642 is provided for exhausting flow media air from extraction channel 635 and chamber 640. As can be seen in FIG. 17, the interior chamber 640 carries a filter 645 for capturing liquid droplets of the aspirated treatment media. In all other aspects, the variation of FIG. 17 functions as previous variations to enhance fluid penetration into a subject's skin, and the rolling member 610 can consist of any of the various types described above. While this variation shows that pump assembly 615 is powered by a battery 618, it should be appreciated that a power cord and a remote power source also fall within the scope of the invention. Further, in the variation shown in FIG. 17 that uses a battery 618, the applicator body 605 can be configured with electrical contacts in a surface of the body 605 to cooperate with a charging stand, as is commonly known in the field of battery-operated handheld devices. As in previous variations, the applicator body 605 can consist of several mating components that can be disassembled to allow cleaning of the interior components of the device, including the rolling member 610, the receiving space 622, the pump assembly 615, the distal aspiration channel 628, the proximal aspiration channel 635, chamber 640 and the filter 645.

Figure 18:
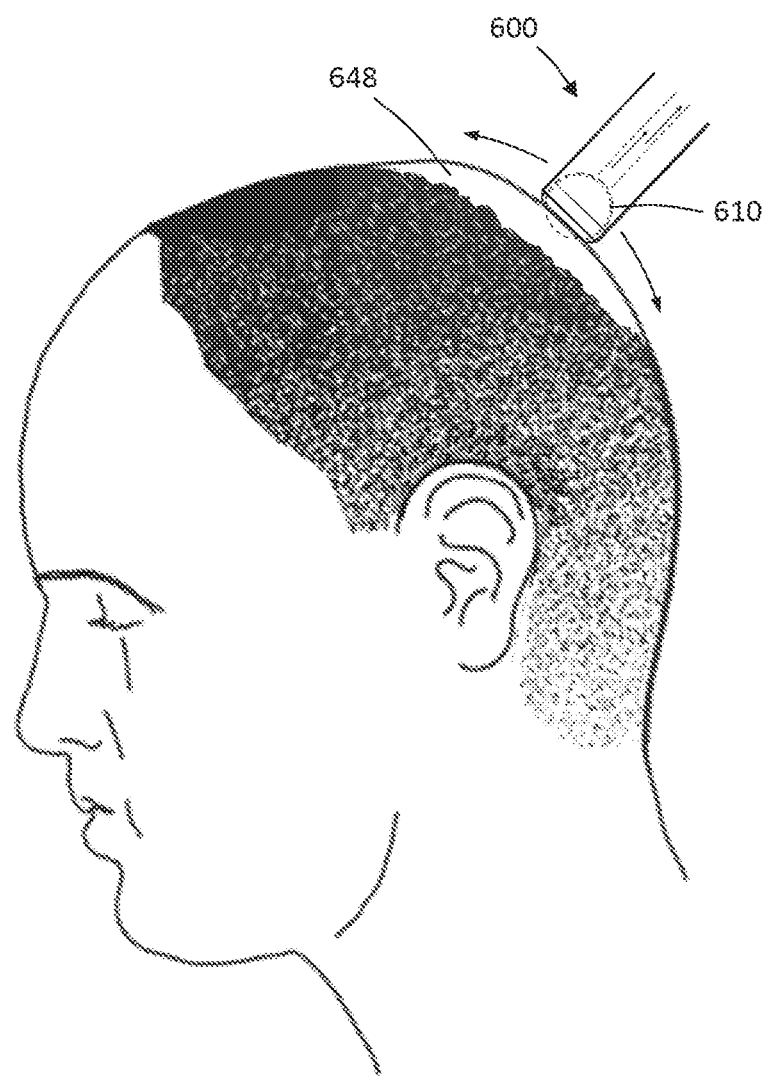
FIG. 18 is an illustration of a method of treating hair loss using the applicator of FIG. 17 to apply and deliver pharmacologic agents to a treatment site on a patient's scalp.
Figures 19, 20:
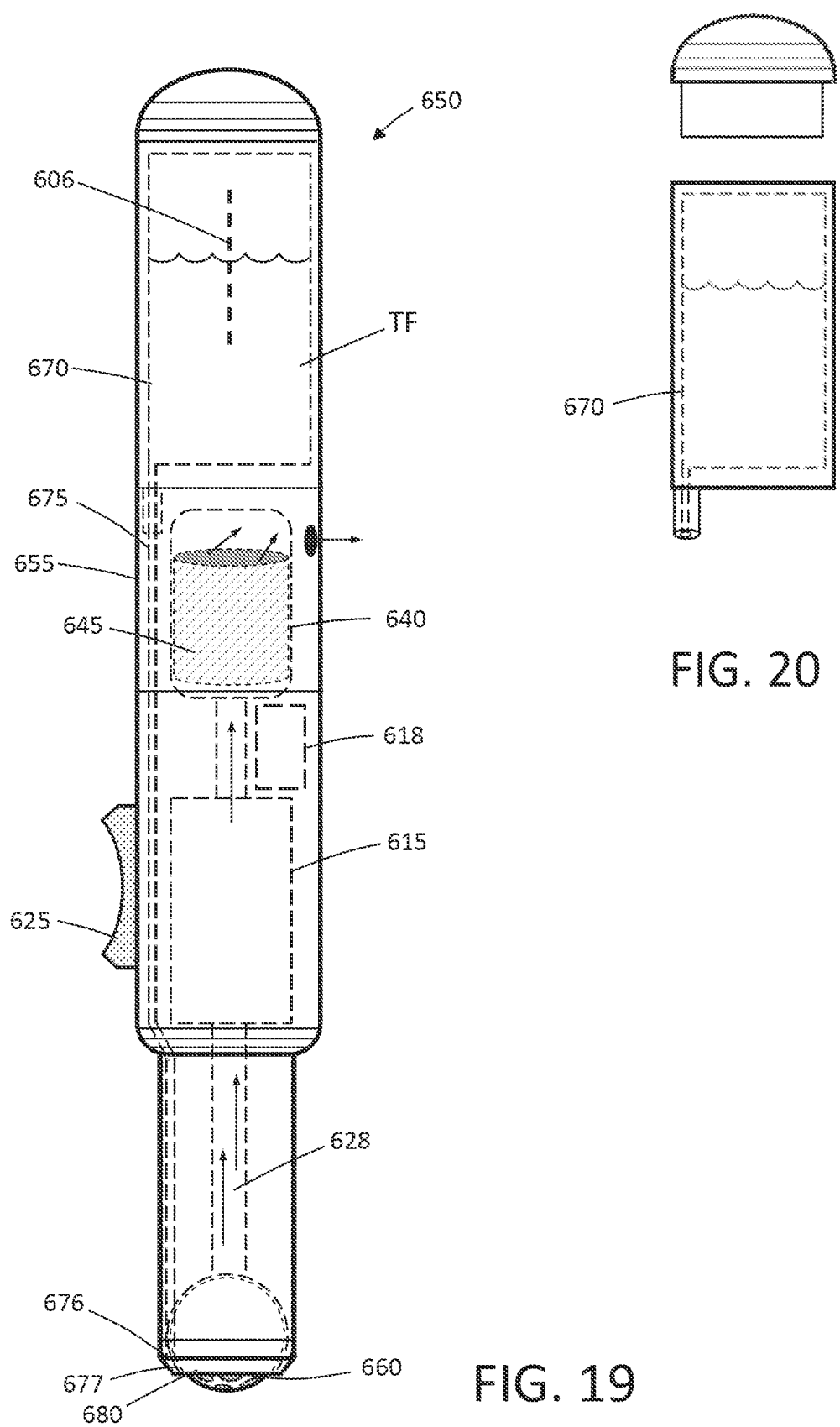
FIG. 19 is an elevational view of another variation of an applicator with a distal rolling member wherein the applicator body carries a DC motor-driven pump assembly, a filter, and a detachable fluid reservoir for carrying a treatment fluid.
FIG. 20 is an elevational view of the detachable fluid reservoir of FIG. 19.
Figure 21:
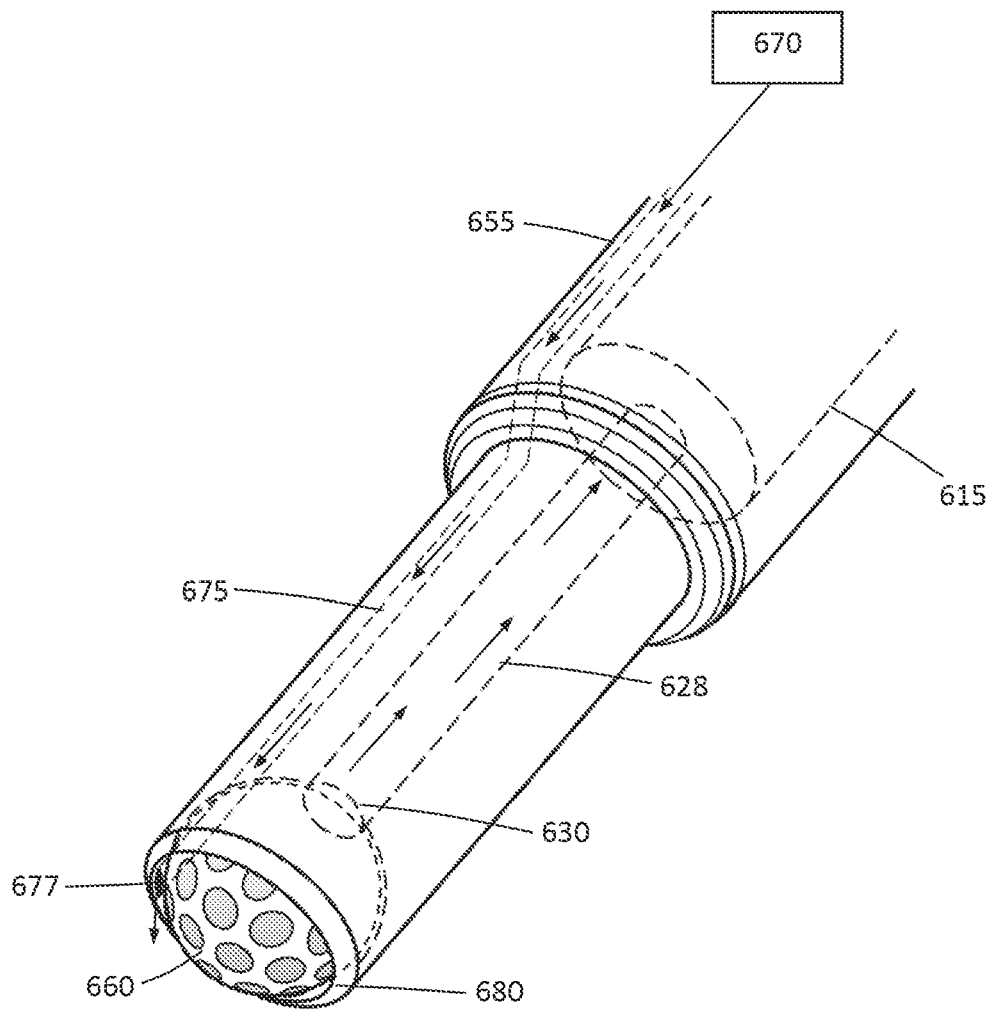
FIG. 21 is an enlarged perspective view of the distal portion of the applicator of FIG. 19.

The device of FIG. 17 is adapted for use in the methods of delivering or applying fluid to tissue as described previously. In another method, the applicator 600 of FIG. 17 can be used to treat hair loss, as shown in FIG. 18. It can be appreciated that the applicators described above, including the applicator of FIG. 17, include an internal pump assembly 615 and are designed to enhance penetration of fluid treatment media into subsurface tissue under a targeted site of the subject's skin. In FIG. 18, the applicator or treatment device 600 is shown being used to apply and enhance the penetration of treatment media into the skin of a subject's scalp 648. In this method, the treatment media can include at least one of finasteride, minoxidil, dutasteride, and a corticosteroid. Currently, such pharmacologic agents have been applied topically and have been shown to have an effect on the restoration of hair growth. The applicator 600 of FIG. 17 and the applicator 650 shown in FIGS. 19-21 are thus adapted to enhance the penetration of such agents into subsurface tissue below the skin surface to enhance hair growth. In other variations, the treatment media can include a psoralen, and the applicator body can include LEDs with the appropriate wavelength to interact with the psoralen to stimulate hair growth. Currently, psoralens have been investigated for enhancing hair growth when irradiated with selected light wavelengths, for example, UV wavelengths.

In general, a method for treating a subject's hair loss comprises topically applying a hair growth treatment media to the targeted tissue of a subject, contacting the tissue and treatment media with an applicator, and causing negative pressure about the applicator in contact with the tissue to transiently cause negative pressure in subsurface tissue to enhance penetration of the treatment media into the subsurface tissue. Further, the method can move the applicator over the tissue to treat broad areas of the subject's scalp. In such a treatment, the treatment media includes at least one finasteride, minoxidil, dutasteride, a corticosteroid, and a psoralen. The step of causing negative pressure includes actuating a vacuum pump mechanism in the applicator body, or alternatively, the negative pressure source is remote form the applicator and coupled to the applicator with a flexible tubing. In one variation, the negative pressure is pulsed to allow manipulation and relaxation of the tissue surface to enhance fluid penetration. In another variation similar to previous applicators, the negative pressure is provided at the interface of the subject's skin by a rolling member 610 in the applicator tip, which provides a flow path through and/or around the rolling member 610 (see FIG. 17). As described in previous variations, moving the rolling member 610 manipulates tissue to thereby enhance penetration of the treatment media into subsurface tissue. Such tissue manipulation can consist of compressing, stretching, tensioning, and/or piercing the tissue surface using the surface features of the rolling member 610. In a variation, the rolling member 610 further removes or exfoliates the epidermis with surface features of the rolling member to thereby enhance penetration of the treatment media in the targeted tissue. The applicator body of FIG. 17 can further be provided with the source of treatment media in a cartridge or reservoir carried by the applicator body, as will be described next in the variation of FIGS. 19-21. The method of treating hair loss described above also can be performed with any of the treatment devices of FIGS. 22-29 that provide negative pressure and tissue manipulation as well as the treatment device of FIGS. 29-30 that provides negative pressure and manipulates tissue without a rolling member.

Figure 23:
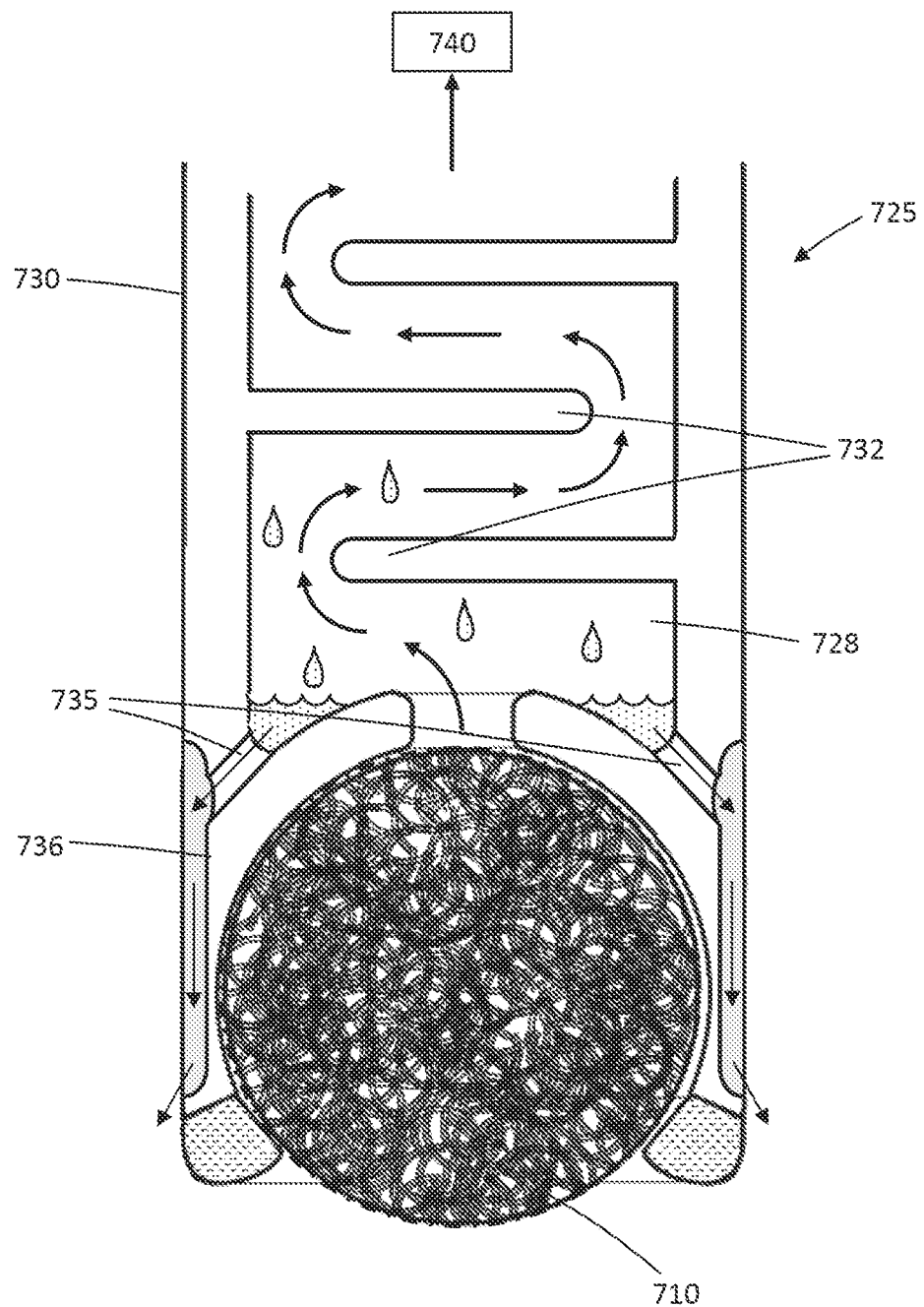
FIG. 23 is a section view of a distal portion of another variation of an applicator that includes baffles in an outflow channel to capture liquid droplets from outflows.
Figure 24:
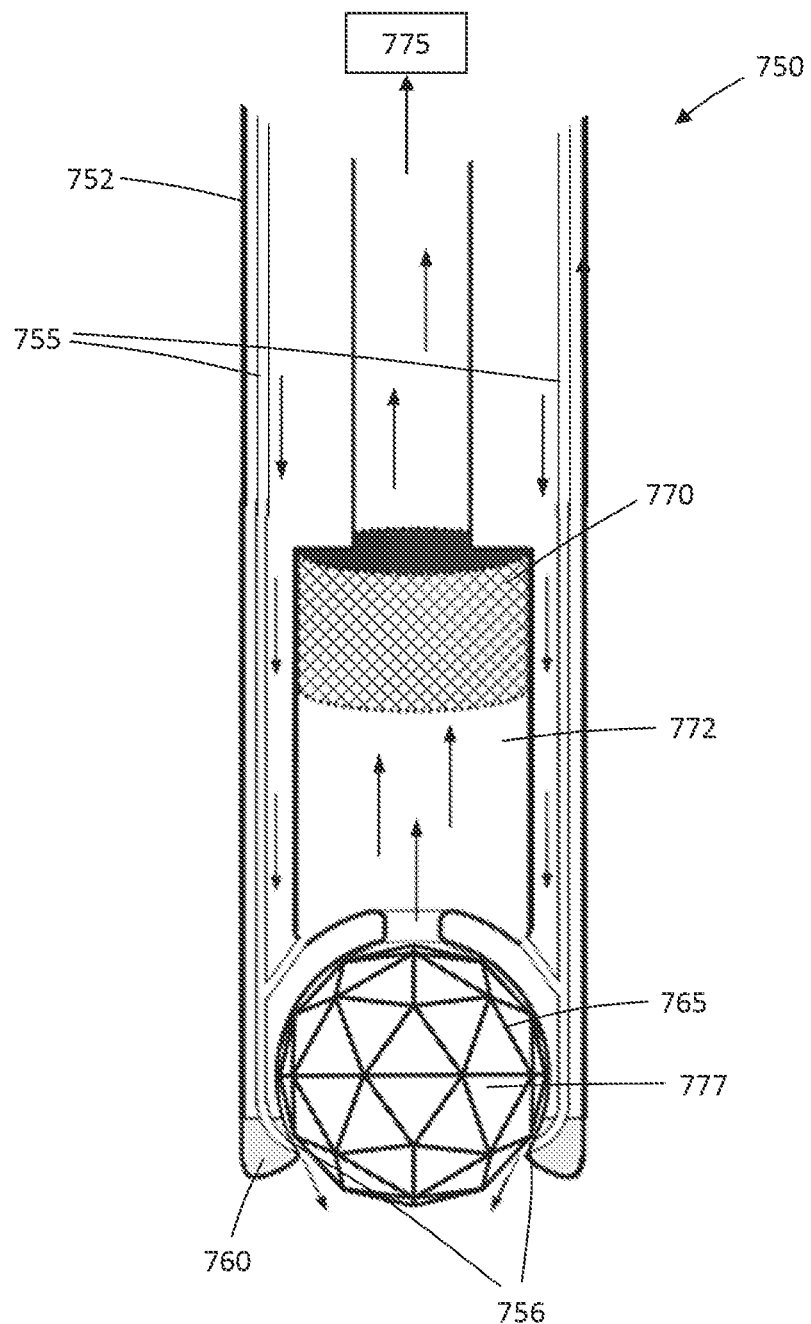
FIG. 24 is a sectional view of the distal portion of another variation of an applicator that carries a faceted rolling member, where the applicator body has fluid inflow channels.
Figure 25:
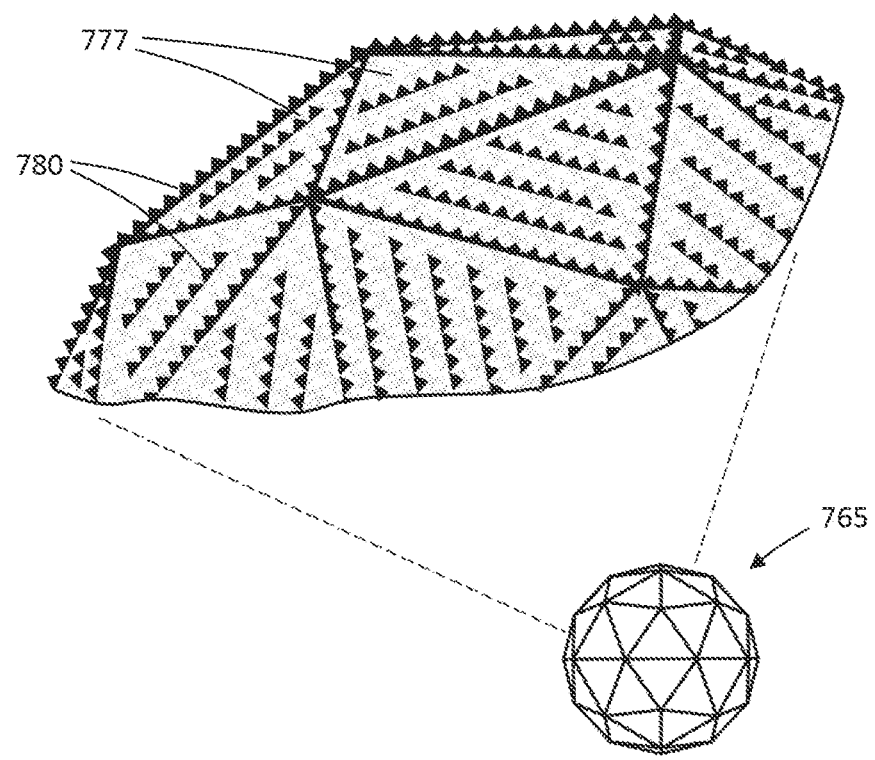
FIG. 25 is an enlarged view of a fragment of the faceted rolling member of FIG. 24, showing diamond particles adhered to the rolling member.

Now turning to FIG. 19-21, another variation of applicator 650 is shown that includes an elongated applicator body 655 with a distal rolling member 660, as described previously. In this variation, the applicator body 655 again carries a pump assembly 615 and battery 618 operated by a switch 625 with fluid and water droplets being extracted through the distal channel 628 and pump assembly 615 to a proximal chamber 640 carrying a filter 645 as described previously. In the embodiment of FIG. 19, the applicator body 655 carries a fluid reservoir 670 that may be detachable or non-detachable and is adapted to carry the treatment fluid TF. FIG. 19 shows the applicator body 655 with the various components in phantom view, and FIG. 20 shows the treatment fluid reservoir 670 in a cartridge 672 removed from the applicator body 655. In this variation, at least one fluid inflow channel 675 is provided from the fluid reservoir 670 to the distal end 676 of the applicator body 655. In a typical variation, the open termination 677 of the fluid inflow channel 675 is proximate to the surface of the rolling member 660 but should be appreciated that the distal edges of the applicator body 655 may form a seal on the subject's skin as described previously. In another variation, the open termination 677 of the at least one fluid inflow channel 675 can be in an exterior surface of the applicator to allow fluid to be applied to the skin outwardly of the rolling member 660, which is similar to that as shown in FIG. 23, which is further described below. In FIGS. 19 and 21, a single fluid inflow channel 675 is shown, but it can be appreciated that a plurality of such channels can be provided with open terminations in the distal end of the applicator.

A key feature of the device of FIGS. 19-21 is the configuration of the components that allows for actuation of the negative pressure source to draw fluid from the cartridge or reservoir 670 through the at least one inflow channel 675 only when the distal tip of the applicator and the rolling member 660 are engaged with the subject's skin. It can be understood that when the distal tip 680 of the applicator body 655 is not in contact with tissue and with the pump assembly 615 being actuated, the only effect will be to pull air around or through the rolling member 660 and into the extraction channel 628 and the interior chamber 640 of the applicator. However, when the distal tip 680 of the applicator is sealed against the subject's tissue surface, then actuation of the pump assembly 615 will apply suction to the open termination 677 of the fluid inflow channel 675 to draw fluid from the fluid reservoir 670 into the distal tip 680 of the applicator.

Figure 22:
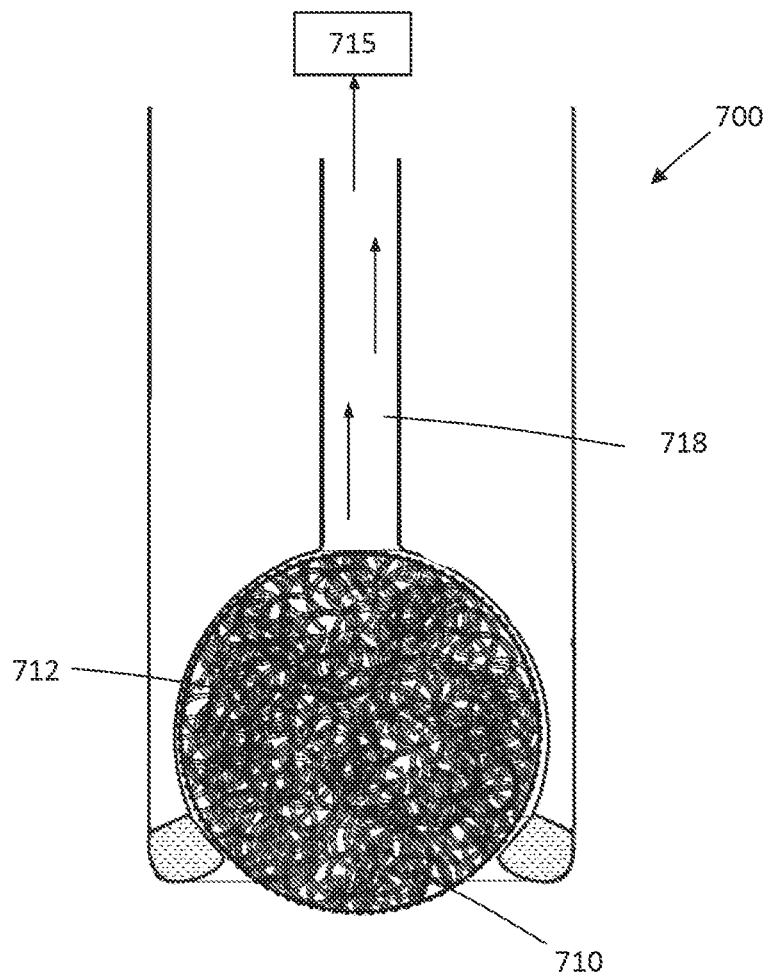
FIG. 22 is an enlarged sectional view of a distal portion of another applicator where a spherical rolling member comprises a mesh structure that functions to manipulate tissue as well as functioning as a filter.
Figure 26:
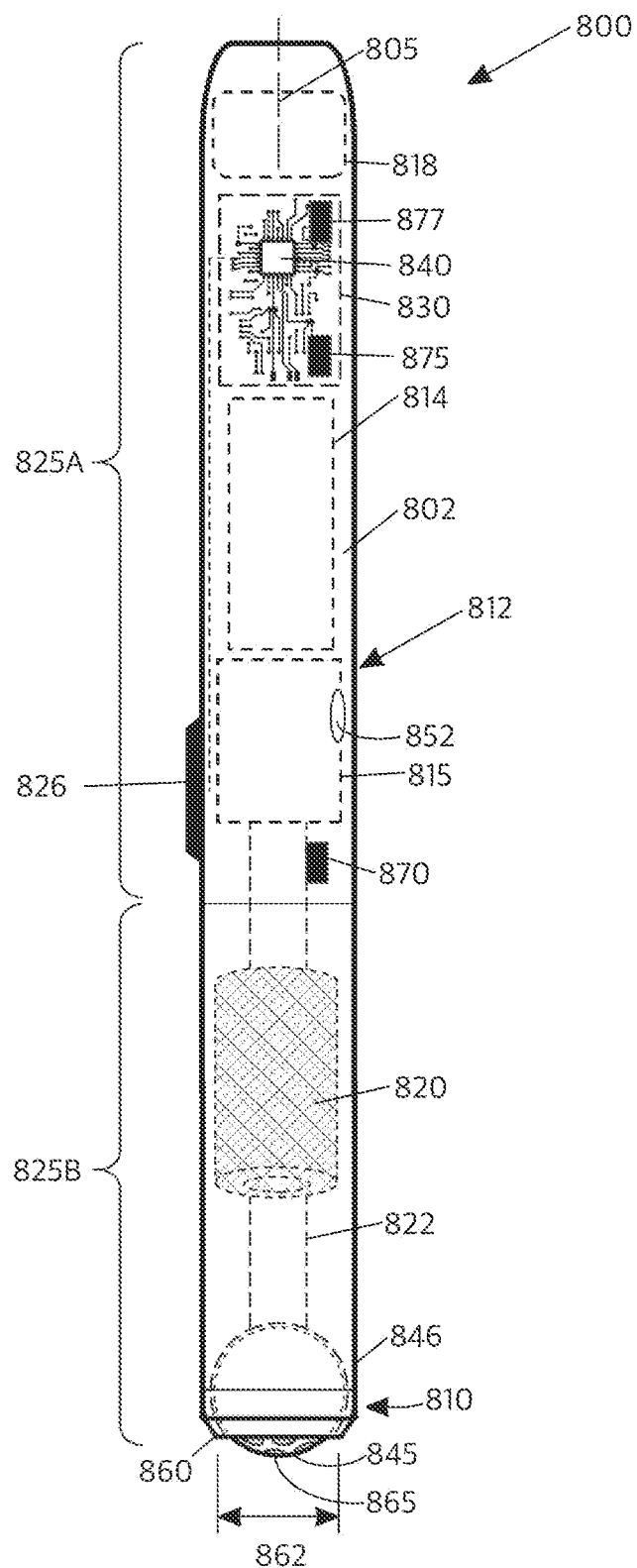
FIG. 26 is a transparent elevational view of another variation of an applicator that carries a distal rolling member, a DC motor-driven pump assembly, a filter, and a battery.

FIG. 22 illustrates another variation of a working end 700 of an applicator 705 that is similar to previous embodiments except for the rolling member 710 comprises a ball or sphere of a mesh fabricated of fine metal wires, polymer filaments, or a combination thereof indicated at 712 that are formed into a spherical shape. The spherical shape can optionally be maintained by adhesives or other suitable means to create a porous spherical member 710. Such a porous spherical member 710 can provide for multiple functions, including comprising a structure with an abrasive surface that can exfoliate skin, providing irregularities in the surface of the rolling member 710 for manipulating tissue and acting as a filter as the negative pressure source 715 suctions treatment fluid through the working end 700 to through outflow channel 718 as shown in FIG. 22. When the mesh rolling member 710 interfaces with a smaller diameter outflow channel 781, it can be appreciated that fluid droplets will be aspirated more readily in a direct path through the rolling member 710 and some liquid will be trapped in interstices of the mesh and fall back onto the skin surface. In other words, such a rolling member 710 can function as a filter and limit the volume of liquid droplets aspirated through the applicator 705. This, in turn, can result in a greater volume of treatment media on the skin surface for penetrating the skin by the action of the rolling member 710. In a variation, the surfaces of the filaments that make up the rolling member 710 can have a hydrophobic or ultrahydrophobic coating for causing fluid to migrate outwardly or distally under the effect of gravity back onto the tissue surface. In other variations, a combination of hydrophilic and hydrophobic surfaces of the materials of the mesh rolling member 710 can be used to trap and filter liquid droplets from the aspirated media.

FIG. 23 is another variation of applicator working end 725 that is similar to that of FIG. 22 with a mesh rolling member 710. In this variation, the extraction channel 728 in the interior of the applicator body 730 includes fluid trapping features 732 for capturing liquid droplets that are aspirated through or around the rolling member 710. The trapping features comprise baffles that extend from opposing sides of the extraction channel 728 or can comprise annular elements with non-aligned apertures therein. Such features can have angled surfaces to cause captured fluid droplets to migrate distally under gravity. In the variation of FIG. 23, the captured liquid can enter drain channels 735 that extends to the exterior surface 736 of the applicator body 730, where the liquid can exit the applicator and fall back onto the patient's skin. In a variation, the drain channels 735 can include one-way valves (not shown), such as a sensitive silicone flap valve to allow the weight of the captured fluid to be released through the channels 735, such that the negative pressure source 740 does not affect the one-way valves.

FIG. 24 illustrates another working end 750 of an applicator body 752 that is similar to that of FIGS. 19-21, where the system carries a fluid cartridge and fluid flows are drawn from a fluid cartridge to the inflow channels 755 to open terminations 756 in the distalmost tip 760 of the applicator around the rolling member 765. This variation of working end 750 includes a filter 770 in the extraction channel 772 distal to the pump assembly 775. FIG. 24 further shows a rolling member 765 with facets 777, which is again adapted for rolling over tissue and manipulating tissue. In the enlarged view of a fragment of the rolling member 765 of FIG. 25, it can be seen that the surface of the rolling member 765 is configured with facets 777 that have micro-penetrating elements that can comprise rough or course diamond particles 780. In this variation, the rolling member 765 rolls over tissue and causes micro-penetrations in the tissue surface caused by the manually applied pressure of the rolling member 765 against tissue in combination with aspiration forces about the facets 777 of the rolling member 765 to enhance penetration of fluid media into subsurface tissues.

Now turning to FIG. 26, another variation of a lip or skin treatment device is shown, which again comprises a self-contained elongated hand-held applicator 800 with an applicator body 802 that extends about a central axis 805 to a distal tip 810 adapted for contacting and treating targeted tissue. The applicator 800 carries a pump assembly or negative pressure source 812 consisting of a DC motor drive 814, a pump 815 such as a diaphragm pump, and a battery 818 for powering the pump assembly. A filter 820 is disposed in an aspiration channel 822 of the applicator body 802 as described in previous variations. The applicator 800 illustrated in FIG. 26 includes a proximal non-disposable component 825A and a distal replaceable component 825B that may be used a number of times (e.g., 1 to 50 times) before replacement. The proximal component 825A carries the motor drive 814, the pump 815, the battery 818, an activation switch 826, and electronic circuitry on a circuit board 830, including a processor or controller 840 for controlling the operating parameters of the device. The distal replaceable component 825B of FIG. 26 is configured with a spherical rolling member 845 as described previously carried in a housing 846 in the distal tip 810, which communicates with the aspiration channel 822 and filter 820 therein that in turn communicates with the negative pressure source 812. The distal component 825B also can be disassembled as described above to allow for cleaning and re-use of the rolling member 845 and cleaning or replacement of the filter 820.

In the variation of FIG. 26, the applicator 800 has an activation switch 826 positioned in the proximal component 825A for activating the negative pressure source 812, although such a switch 826 could be carried in the distal component 825B as will be described in the variation of FIG. 28. In one variation, the negative pressure source comprising a motor drive 814 and diaphragm pump 815 can be an AIMELIAE DC 3V Micro Vacuum Air Pump coupled to a Lipo #301120 3.7V 40 mAh rechargeable lithium-ion battery pack. FIG. 26 also shows that the applicator 800 has at least one exhaust port 852 for outflows from the negative pressure source 812.

Figure 27:
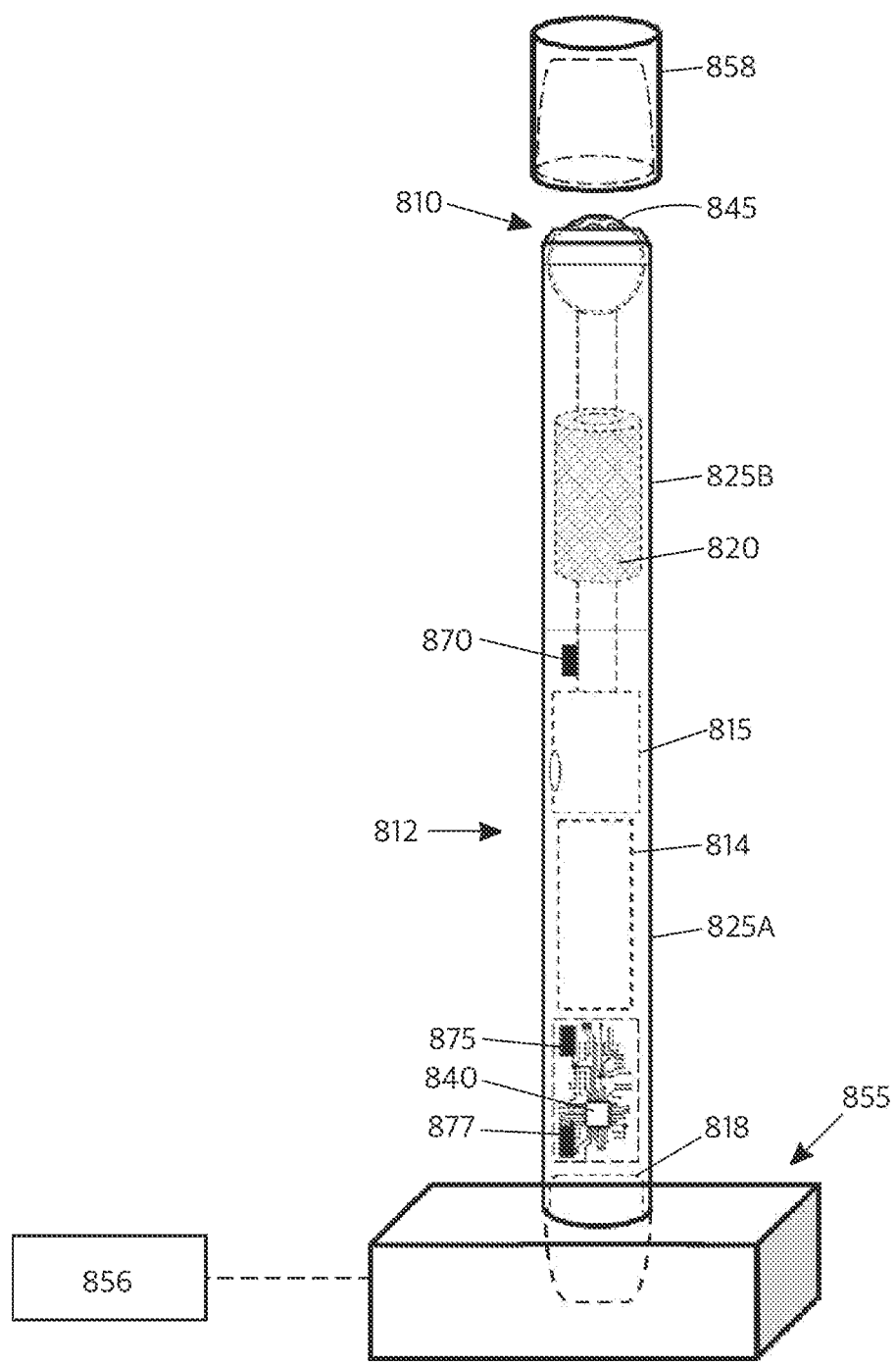
FIG. 27 is a view of the applicator of FIG. 26 inverted and shown inserted in the base unit configured for recharging the battery.

FIG. 27 shows the applicator 800 of FIG. 26 in an inverted position and inserted into a base 855 connected to electrical source 856 that is adapted for inductively recharging the battery 818 as is known in the art. A removable cap 858 is shown for covering the distal tip 810 when not in use.

In one variation, the applicator 800 is adapted for lip treatments, as illustrated in FIG. 26, and has an elongated applicator body 802 that has a cylindrical shape or an oval cross-section, with or without proximal and/or distal tapered regions, wherein the outer surface of applicator body 802 has a maximum diameter of 30 mm or less, 25 mm or less, or 20 mm or less. In this variation, the applicator body 802 has an axial length of 15 cm or less. These dimensions allow the applicator 800 to be carried conveniently by the subject in a pocket or purse.

The applicator 800 of FIG. 26 is adapted to be used in a method as described previously where the perimeter portion 860 of the distal tip 810 contacts targeted tissue and forms a seal against the targeted tissue. Negative pressure provided by the negative pressure source 812 then suctions a surface of the targeted tissue against the rolling member 845. The user then moves the distal end 810 over the targeted tissue, where the rolling number 845 reduces friction while contemporaneously manipulating the targeted tissue to enhance tissue permeability. At the same time, the negative pressure is distributed over an aspiration portion 862 of the distal tip 810 that is surrounded by perimeter portion 860, which forms the seal against the tissue. In this variation, as in previous variations, the negative pressure is provided through a plurality of discreet apertures 865 in the aspiration portion 862. In this variation, the apertures 865 extend through and around the rolling member 845, which are adapted to (i) reduce friction when moving the distal tip 810 over tissue and (ii) prevent excess negative pressure from interfacing with any overly larger surface portion of the targeted tissue which could grip the tissue surface and resist movement of the tip over such a tissue surface. The distribution of negative pressure over the plurality of apertures 865 can further prevent unwanted localized damage to microvasculature in subsurface tissue.

Referring to FIG. 26, the applicator 800 carries a processor or controller 840 for controlling operating parameters of negative pressure source 812, as well as other optional components described further below. In FIG. 26, it can be seen that the applicator 800 also carries a pressure sensor 870 exposed to the aspiration channel 822 in the applicator body for sensing negative pressure therein. In a variation, the pressure sensor 870 is adapted to sense negative pressure during use and send signals to the controller 840. The controller 840 is then configured to modulate the negative pressure source 812 to maintain a selected negative pressure within the applicator 800 or to deactivate the negative pressure source 812 if excessive negative pressure is sensed over a selected time interval.

Still referring to FIG. 26, the applicator 800 also carries at least one accelerometer 875, which allows for sensing the user's movement of the applicator 800. In one mode of operation, the accelerometer 875 can be adapted to sense non-movement of distal tip 810 over the targeted tissue and then send signals to the controller 840, wherein the controller 840 then modulates or de-activates the negative pressure source 812. This mode of operation can prevent the distal tip 810 from being suctioned against tissue when the direction of movement of the distal tip 810 is reversed.

In another variation (not shown), the perimeter portion 860 of the distal tip 810 can carry spaced-apart electrical contacts coupled to the controller 840 and battery 818 to sense capacitance, impedance, or phase angle of an electrical current to allow for sensing tissue engagement by such electrical contacts. In this variation, the controller 840 can then activate the negative pressure source 812 upon sensed contact with tissue and deactivate the negative pressure source 812 upon loss of tissue contact. In another variation, the perimeter portion 860 of the distal tip 810 can carry one or more pairs of electrodes (see FIG. 32A) for delivering electrical current to a subject's skin or lips for electroporation or stimulus purposes.

In another variation, referring to FIG. 26, the controller 840 is configured to enable a mode of operation, including a time-out feature that is adapted to deactivate the negative pressure source 812 after a selected interval of continuous use followed by a selected time-out interval. This mode of operation prevents the over-application of negative pressure to the targeted tissue. In another mode of operation, the controller 840 is configured to pulse the negative pressure source 812.

Figure 28:
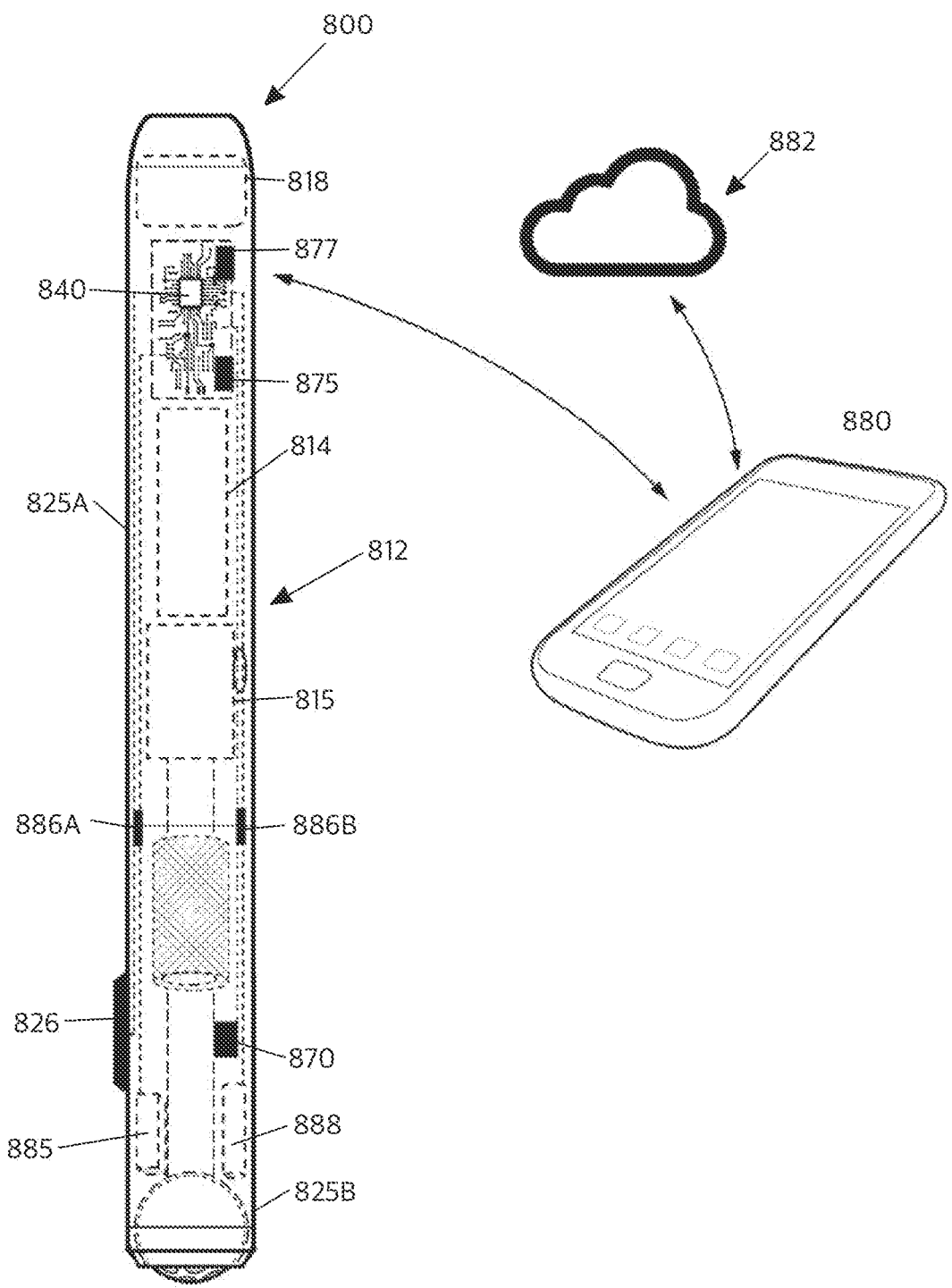
FIG. 28 is a transparent elevational view of another variation of applicator similar to that of FIG. 26 with an optional LED and an optional vibration mechanism, further illustrating a blue-tooth component for wireless communication with a mobile device and the cloud.

Now referring to FIGS. 26 and 28, the applicator 800 also carries a Bluetooth transmitter-receiver 877 for communicating wirelessly with a remote mobile device 880, such as a cell phone or tablet where an app on the mobile device 880 is adapted to communicate with the controller 840 to adjust operating parameters of the applicator. Also, as can be seen in FIG. 28, the applicator 800 and mobile device 880 can communicate with the cloud 882 for storing data for analytic purposes. The operating parameters that can be adjusted within a first or default mode of operation include but are not limited to (i) a maximum allowable negative pressure during use, (ii) a targeted set pressure, (iii) a time interval of allowable excess negative pressure, (iv) a maximum interval of continuous use, (v) the length of a time-out interval, (vi) ON-OFF off the pulse rate of negative pressure, (vii) variability of pulse rate of negative pressure; (viii) time interval following accelerometer signals relating to lack of movement for modulating negative pressure, and (ix) manual activation of the negative pressure source or contact-based activation of the negative pressure source.

Further, the app on the mobile device 880 can be used to switch between other operating modes of the applicator 800. In one variation, a second mode of operation includes activating at least one LED 885 (FIG. 28) carried by the applicator 800, including a selection of operating parameters thereof, including LED light intensity, LED wavelength, and continuous or pulsed activation of the LED 885.

Further, the app on the mobile device 880 can be used to switch to a third mode of operation which includes activating the at least one vibration mechanism 888 or ultrasound transducer carried by the applicator 800, including a selection of operating parameters thereof. Further, the app on the mobile device 880 can be used to switch to a fourth mode of operation which includes activating an electrical current delivery component of the applicator (see FIG. 32A), including a selection of operating parameters thereof.

Still referring to FIG. 28, it can be seen that electrical connectors 886a and 886b are provided between the proximal component 825A and the distal component 825B (see FIG. 26) to couple the activation switch 826, the LED 885, and the vibration mechanism 888 to the controller 840 and battery 818. Similar connectors (not shown) can be provided for and contact-sensing component and any electrical current delivery component as described above.

Now turning to FIG. 29, an enlarged view of the distal tip 810 of the applicator 800 of FIG. 26 is shown wherein the perimeter portion 860 of the distal tip 810 comprises a lubricious material or a flexible sponge-like material 892 that is adapted to absorb liquid treatment media and carry such treatment media over the targeted tissue during use. The perimeter portion 860 again surrounds the aspiration portion 862, that comprises the exposed surface of the rolling member 845.

In some variations, the treatment media TM (see FIG. 32A) includes at least one of a hyaluronic acid HA or derivative thereof, Vitamin E, Vitamin B3, retinol, *Mentha piperita* leaf, a peptide complex to support collagen production, and an irritant such as cinnamon, ginger, wintergreen, or bee venom. In one variation, a hyaluronic acid HA or derivative thereof is a key component of the treatment media, as shown schematically in FIG. 32A. Hyaluronic acid is abundant in skin and lips of a human subject and is unique in that HA retains large amounts of moisture in the skin, which in turn provides a plump and youthful appearance to a subject's skin or lips.

FIG. 30 shows another variation of an applicator distal tip 810' without a rolling member that is configured with a lubricious perimeter portion 860' similar to that of FIG. 29. Alternatively, the perimeter portion 860' can be sponge-like material 892 as in the variation of FIG. 29. In the variation of FIG. 30, the perimeter portion 860' of the distal tip 810' has a planar distal-facing surface 895, wherein the aspiration portion 862' of the distal tip comprises a concavity 896 where negative pressure interfaces with the targeted tissue. The aspiration portion 862' is configured with a plurality of apertures 898 having a diameter of less than 2.0 mm that communicate with the negative pressure source 812. Each of the apertures 898 is within a non-apertured field 900 of the aspiration portion 862'. By configuring the aspiration portion 862' with such apertures 898 and such a non-apertured field 900, the negative pressure is distributed evenly over all portions of the targeted tissue that interfaces with the distal tip 810' and prevents the aspiration portion 862' from being suctioned tightly against tissue, which would prevent effortless movement over targeted tissue. Typically, the distal tip of an applicator has a surface area of at least 25 mm$^2$. In one variation, the surface area of the distal tip is between 25 mm$^2$ and 125 mm$^2$ for an applicator configured for treating lips, whether it carries one or more rolling members or is of the type shown in FIG. 30.

Figure 31A:
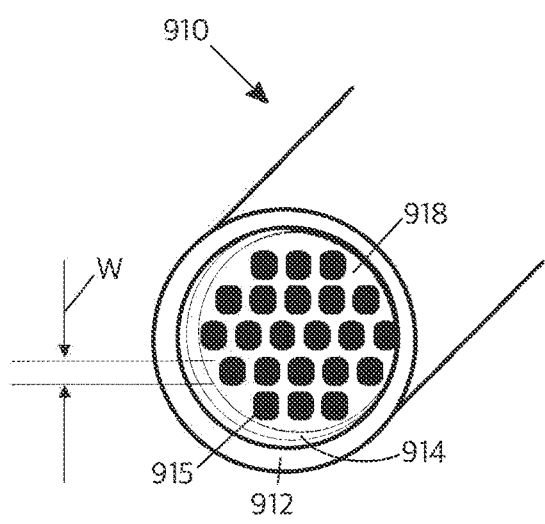
FIG. 31A is a perspective view of an applicator tip similar to that of FIG. 29 showing small diameter apertures in an aspiration portion of the tip.
Figure 31B:
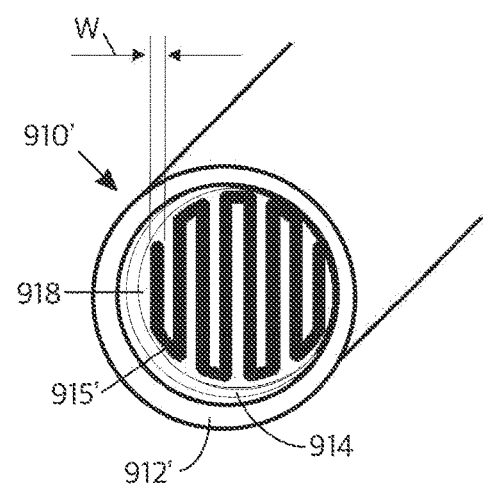
FIG. 31B is a perspective view of another applicator tip configured with a narrow serpentine aperture.

FIG. 31A is a perspective view of a distal tip 910 similar to that of FIG. 30, where a perimeter portion 912 surrounds a concave aspiration portion 914 that is configured with a plurality of substantially round apertures 915 and a non-apertured field 918. In this variation, each aperture 915 has a width W or dimension of a minor axis of 2.0 mm or less. FIG. 31B is a perspective view of a distal tip 910' similar to that of FIG. 31A, where a perimeter portion 912' surrounds a concave aspiration portion 914' with an aperture 915' comprising a serpentine slit within a non-apertured field 918. In this variation, the aperture 915' has a width W or dimension of a minor axis of 2.0 mm or less. As can be seen in FIGS. 31A and 31B, the apertures 915 and 915' are provided in all regions of each tip's aspiration portion 914 and 914', respectively to distribute exposure to negative pressure over corresponding discrete portions of the surface of targeted tissue, which prevents the tip from being suctioned firmly against the tissue surface.

Figure 32A:
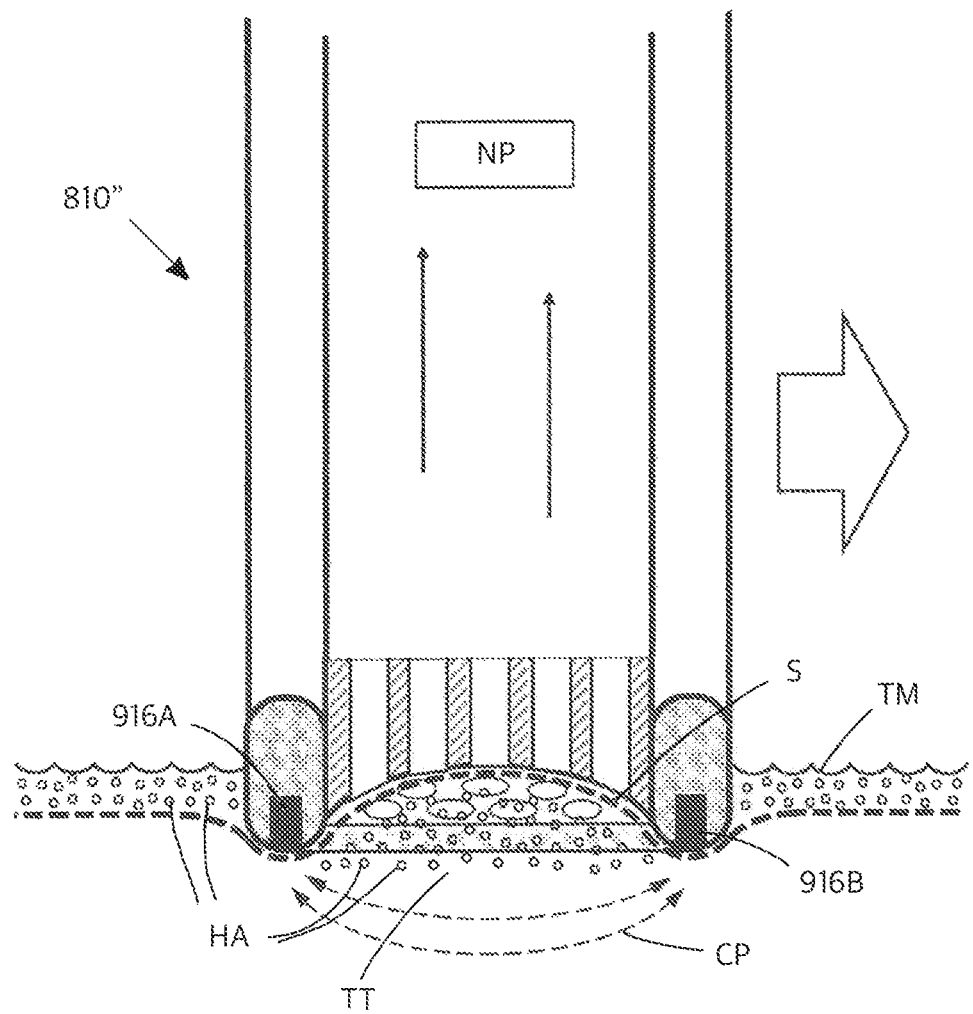
FIG. 32A is a schematic illustration of another variation of the applicator tip that contemporaneously applies negative pressure and an electroporation current to a subject's lip or skin to cause transport of hyaluronic acid through the surface to subsurface tissue.

Now turning to FIG. 32A, a distal applicator tip 810" is shown with an electrode arrangement therein comprising electrodes 916a and 916b that are adapted to deliver a pulsatile electrical current in current paths CP to the targeted tissue TT to enhance transportation of hyaluronic acid HA into subsurface targeted TT tissue through the skin surface S by means of electroporation in combination the negative pressure as described above and below. The method of electroporation has been shown to create transient aqueous pores in cell membranes upon application of electrical pulses, typically comprising short-duration high-voltage pulses. During such electrical pulsing, molecules which would not normally penetrate skin can be transported through the skin surface S during the interval of induced, reversible permeability of skin surface membranes. The transdermal transport of molecules of different sizes, including high molecular weight proteins, peptides, oligonucleotides, etc., is possible. In some variations, the method for delivering the pulsed current in current paths CP in FIG. 32A to the subject's lips or skin comprises applying a pulsed current having an average current density ranging from 0.01 mA/cm$^2$ to 20 mA/cm$^2$, a pulse width ranging from 5 microseconds to 1 millisecond, a plurality of pulsatile wave packets from 1 to 100 pulses, and frequency of such wave packets ranging from 5 Hertz to 1,000 Hertz.

Referring to FIG. 32B, a method of treating a subject's lips or skin comprises topically applying a treatment media including a hyaluronic acid (HA) or derivative thereof to a targeted tissue of the subject's lips or skin, applying a selected level of negative pressure to the targeted tissue with a distal tip of an applicator, and applying a pulsed electroporation current to the targeted tissue wherein the selected level of negative pressure and the selected pulse parameters allow for to transport of the hyaluronic acid or derivative thereof through the surface of the targeted tissue to subsurface tissue. In this method, the negative pressure is applied to the tissue at the distal tip of an applicator at a selected level of negative pressure of at least negative 3.0 psi. In some variations of the method, the negative pressure at the surface S of the tissue is at least negative 4.0 psi. In another method variation, the negative pressure is at least negative 5.0 psi. In this method, the electrical current is pulsed with pulse widths ranging from 5 microseconds to 1 millisecond, where pulses are provided in wave packets of 1 to 100 pulses with a frequency of wave packets application ranging from 5 Hertz to 1,000 Hertz.

Figure 33A:
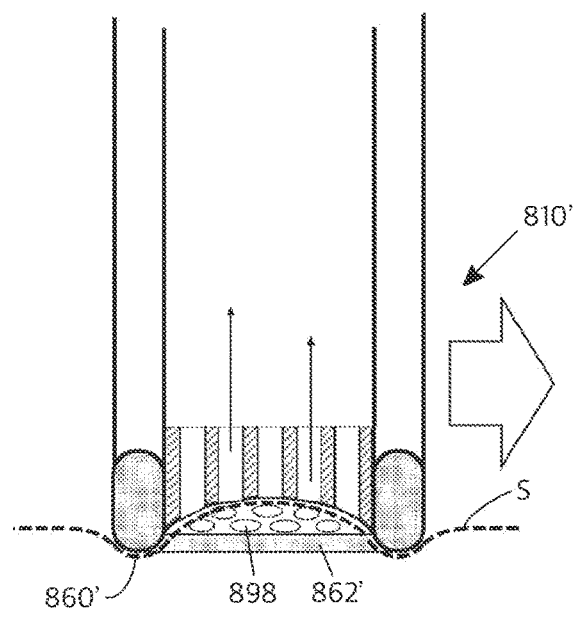
FIG. 33A is a schematic sectional view of the applicator of FIG. 29 with a plurality of small apertures in use being moved over tissue with the tissue surface suctioned into an interface with the tip and apertures.
Figure 33B:
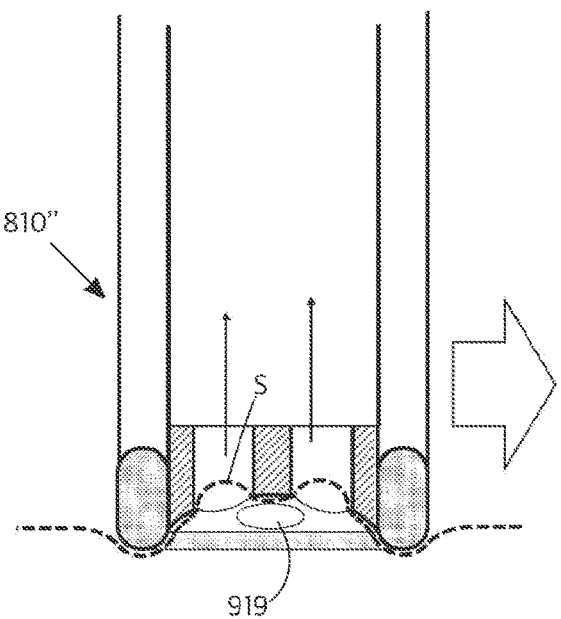
FIG. 33B is a schematic sectional view of a hypothetical applicator tip with over-sized apertures that suction tissue into such apertures, grips the tissue, and thus prevents smooth movement of the tip over tissue.

FIGS. 33A and 33B schematically illustrate the importance of providing an applicator distal tip and aspiration portion that distributes negative pressure over the surface of tissue that interfaces with a distal tip adapted for sliding movement over tissue. FIG. 33A depicts a sectional view of the distal tip 810' of FIG. 30 being moved over a surface S of targeted tissue under a selected level of negative pressure where the perimeter portion 860' and the aspiration portion 862' comprise a lubricous material. The distal tip 810' can be moved smoothly over the surface S of the tissue as the apertures 898 are small, as described above, and the negative pressure cannot suction the tissue surface S into the apertures, which would grip the tissue. Still, the negative pressure is exposed to the tissue surface to create negative pressure in subsurface tissue, as described above. In contrast, FIG. 33B illustrates a sectional view of a hypothetical distal tip 810" that contains only four larger apertures 919. In FIG. 33B, it can be seen that same level of negative pressure as in FIG. 33A could suction the surface S of the tissue into the apertures 919, which would grip the tissue and inhibit or prevent movement of the distal tip over the surface S of the tissue, which would be disadvantageous.

In general, a method for treating a subject's skin or lips with an applicator of the invention comprises (i) providing an applicator carrying a negative pressure source for causing negative pressure within the applicator, wherein a distal tip of the applicator has a perimeter portion surrounding an aspiration portion with at least one aperture therein, wherein the at least one aperture has a width or minor axis of 2.0 mm or less, wherein the at least one aperture is disposed in substantially all regions of the aspiration portion, and wherein the aspiration portion has a surface area of at least 25 mm$^2$, and (ii) contacting targeted tissue of a subject's skin or lips with the distal tip of the applicator, activating the negative pressure source and moving the distal tip over the targeted tissue to transiently cause negative pressure in subsurface tissue. A topical treatment media may be applied to the tissue surface before and during use. The negative pressure source 812 is configured to provide a negative pressure of at least negative 3.0 psi at the distal tip when in contact with tissue. In some variations of an applicator, the negative pressure at the distal tip when in contact with tissue during use is at least negative 4.0 psi, and in some embodiments is at least negative 5.0 psi.

FIG. 34 illustrates a distal tip 920 of another variation of applicator where the perimeter portion 922 is rectangular and again has a planar distal-facing surface 924. The aspiration portion 925 of the distal tip 920 comprises a recessed region 926 where negative pressure can interface with targeted tissue. The aspiration portion 925 is configured with a plurality of elongate slit-type apertures 928 that communicate with the negative pressure source. Each of the slit-type apertures 928 is surrounded by a non-apertured field 930 of the aspiration portion 925, and each aperture 928 has a width W of 2.0 mm or less. In all variations herein, the width of any aperture is less than 2.0 mm and often 1.0 mm or less to distribute the negative pressure evenly over the targeted tissue and prevent tissue from being suctioned tightly against the distal tip.

FIG. 35A depicts another variation of an applicator distal tip 940 with a perimeter portion 942 having a rectangular shape with a distal-facing surface 944 that is non-planar and exhibits an inward curvature 945 that is adapted for improved contact with a subject's lips. In this variation, the plurality of apertures 948 comprise channels through multiple spherical rolling members 950 as well as spaces 952 adjacent to and around the rolling members 950. Each of the spherical rolling members 950 can disposed in a housing 954, allowing for rolling of each rolling member 950 in any direction. In another variation, the rolling member 950 can be configured with an axle and can rotate in either rotational direction about such an axle (not shown).

Figure 36:
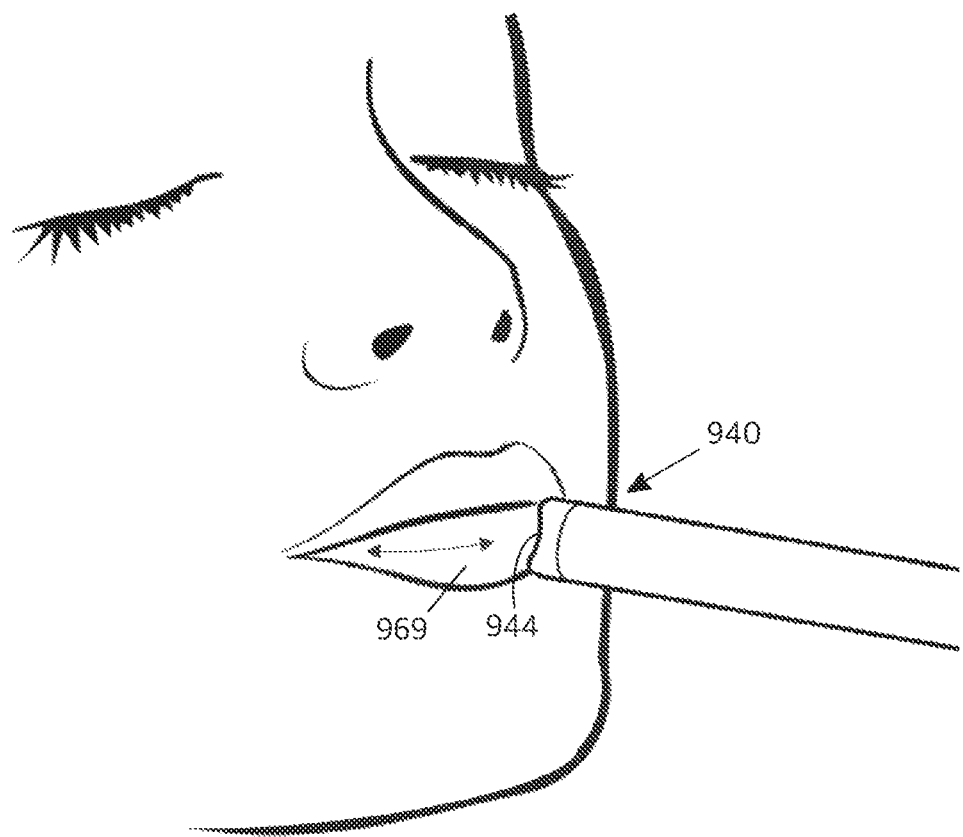
FIG. 36 is a view of an applicator tip configured with a non-planar distal-facing periphery in use on a subject's lips.

FIG. 35B shows another variation of an applicator distal tip 960 that has a rectangular perimeter portion 962 with a non-planar distal-facing surface 964 and an inward curvature 965 adapted for treating lips. In this variation, the plurality of apertures comprises narrow slits 968, similar to the distal tip of FIG. 34. FIG. 36 illustrates a method of use of an applicator of the types in FIGS. 35A and 35B, such as tip 940 with a non-planar distal surface 944 having a curvature 945 that fits the curved shape of a subject's lips 969.

Figure 37:
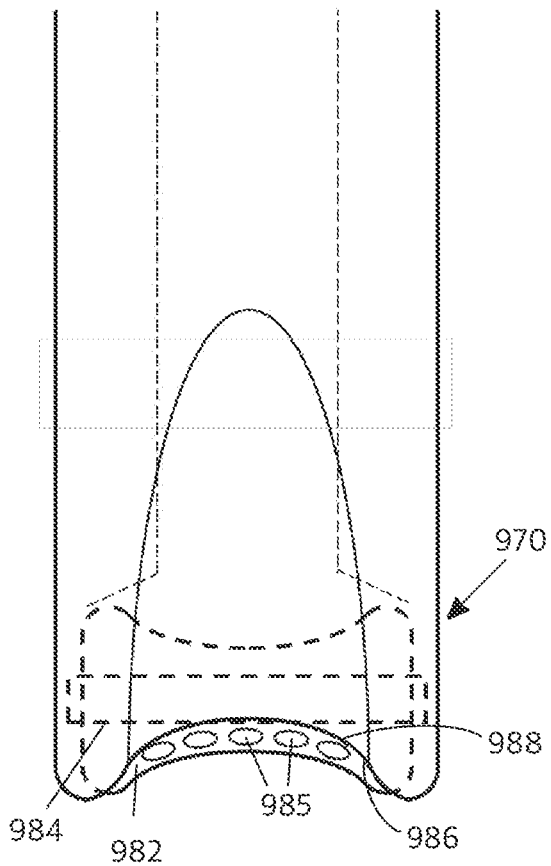
FIG. 37 is an elevational view of another applicator tip configured with an hour-glass shaped rolling member and a cooperating non-planar distal-facing periphery.
Figure 38:
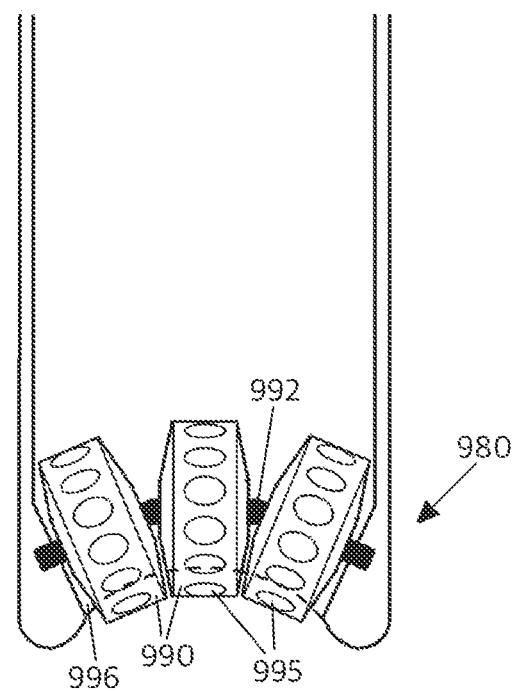
FIG. 38 is a sectional view of another applicator tip with a non-planar distal-facing periphery and a plurality of rolling members that rotate about an axle.

FIGS. 37 and 38 show other variations of applicator distal tips 970 and 980 with respective distal-facing surfaces that are non-planar and exhibit an inward curvature again adapted for contact with a subject's lips. In the variation of FIG. 37, an hour-glass shaped rolling member 982 is provided that rotates around a central axle 984. A plurality of apertures 985 comprising channels are provided in the rolling member 982 as well as spaces 986 adjacent to and around the rolling member 982. The perimeter portion 988 has an hourglass shape around the rolling member 982. FIG. 38 illustrates a distal tip 980 with a plurality of rolling members 990 that rotate around portions of an axle 992. Again, a plurality of apertures 995 is provided in the rolling members 990 as well as in spaces 996 adjacent to and around the rolling members 990.

In other variations, an ultrasound wave generator such as a piezoelectric crystal can be provided in the distal tip of the applicator to deliver pressure waves at ultrasonic speeds to the skin, for example, in the range of 1 Mhz to 6 Mhz to enhance fluid absorption. In another variation, the working end can include components and electrodes for delivering electrical current through the rolling member or the distal periphery of the roller housing to the skin of a patient to enhance fluid penetration. In a further variation, the LEDs, as in FIG. 11, can transmit UV light to kill bacteria.

Figure 39B:
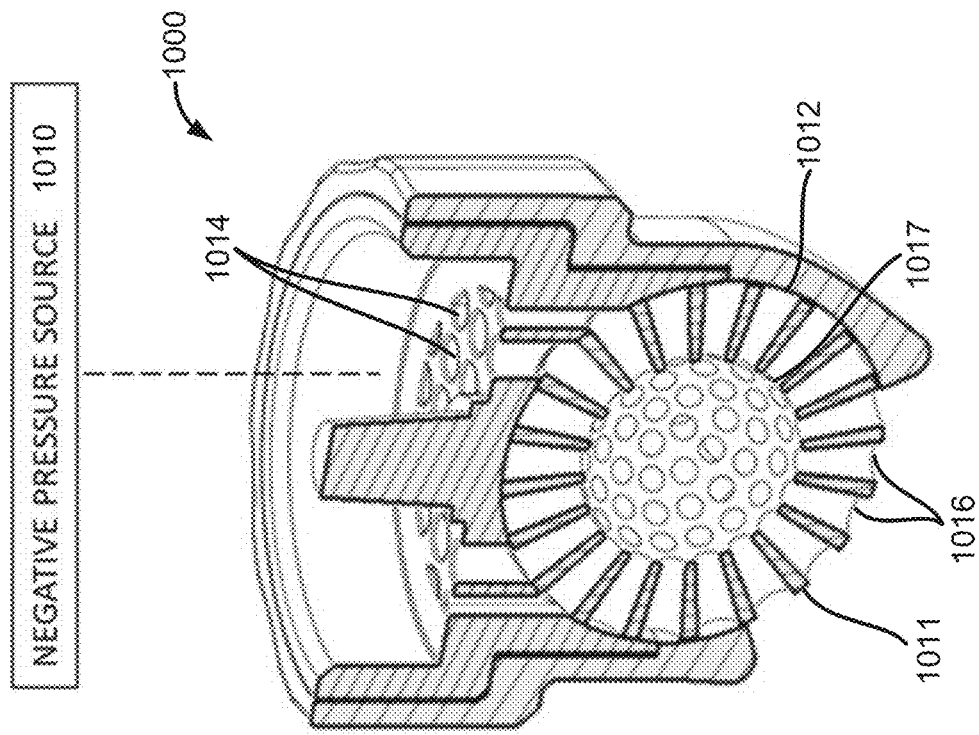
FIG. 39B is a sectional view of the treatment tip of FIG. 39A.
Figure 39A:
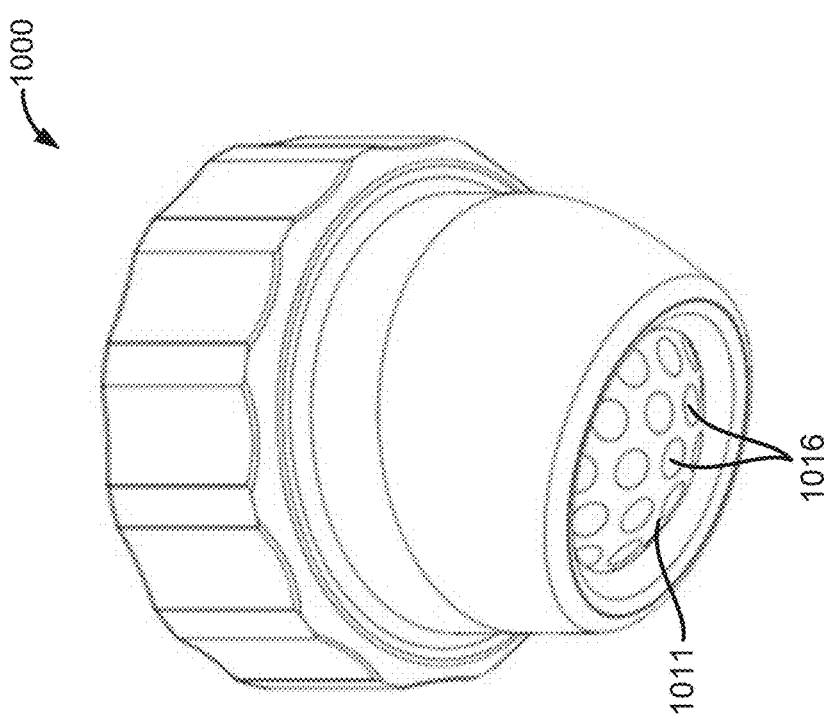
FIG. 39A is a perspective view of a treatment tip with a rolling member having a plurality of bores therein.
Figure 40:
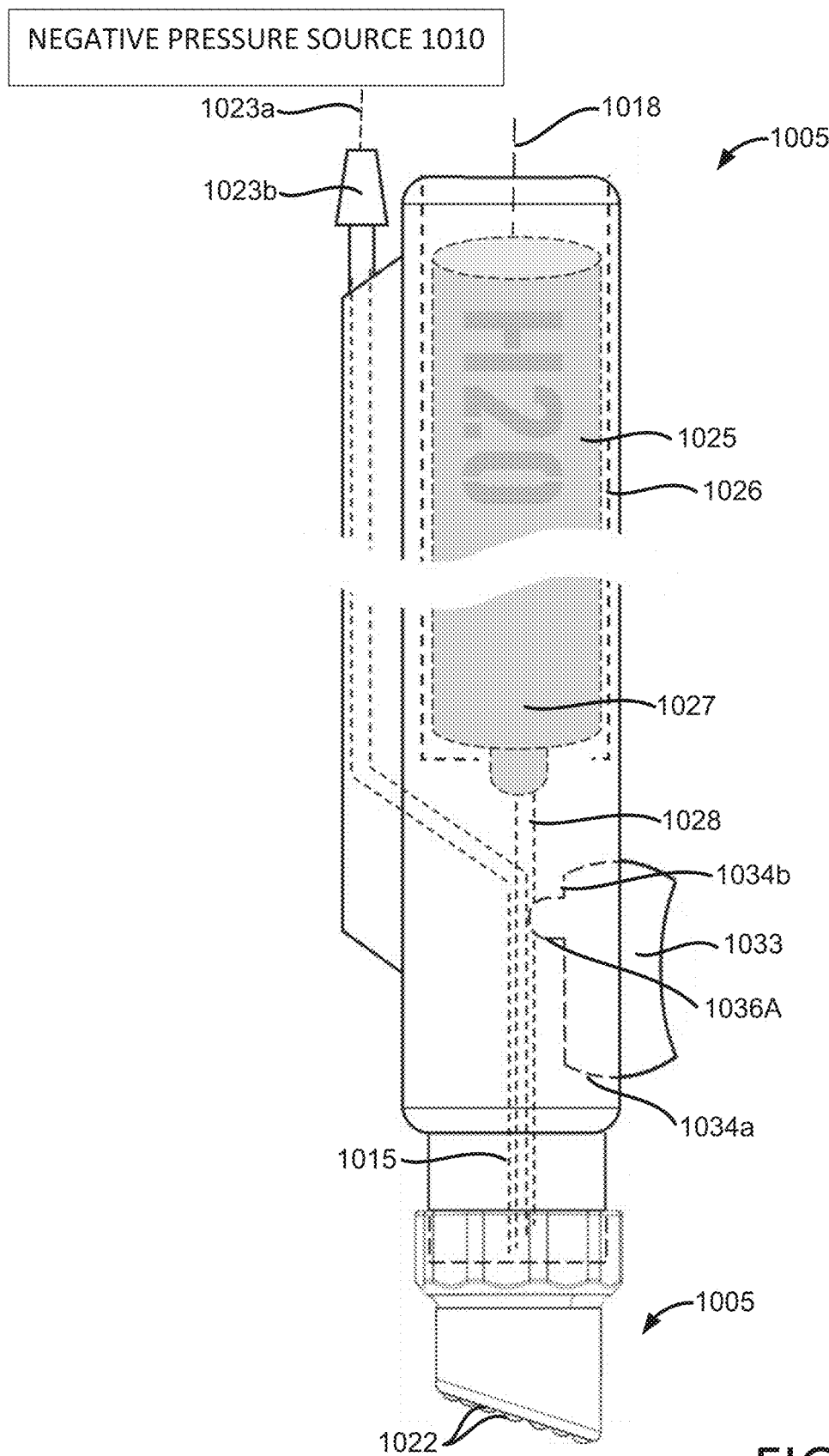
FIG. 40 is an elevational view of a hand-held applicator body with an outflow channel communicating with a negative pressure source, an inflow channel communicating with a fluid source comprising a cartridge, a detachable distal treatment tip having a low-traction surface comprising a plurality of rolling members, and a rocker actuator member in the applicator body for controlling fluid flows to and from the distal tip.

FIGS. 39A and 39B illustrate another variation of a distal treatment tip 1000 that can be coupled to a hand-held skin treatment applicator of the type shown in FIG. 7 or the applicator 1005 of FIG. 40. Such an applicator has a negative pressure source carried in the applicator body or is coupled to a remote negative pressure source 1010, as shown in the applicator of FIG. 40. In the variation of FIGS. 39A-39B, the rolling member 1011 is carried in a receiving space 1012 in the tip 1000 wherein a plurality of openings 1114 in the interior of the tip communicate with the receiving space 1012 and the negative pressure source 1010 through an outflow channel 1015 in the applicator body (see FIG. 40). In this variation, the rolling member 1011 is spherical with a plurality of bores 1016 extending through the rolling member 1011. In a variation, the rolling member 1011 also has a central interior chamber 1017, wherein such a rolling member 1011 can be fabricated by 3D printing or injection molding in two pieces. The variation of FIGS. 39A-39B is adapted for use when a serum or fluid is applied topically to targeted skin, but the tip 1000 could also have fluid inflow channels of the type shown in FIG. 24. In all other aspects, the tip 1000 of FIGS. 39A-39B performs as other applicator tips with a rolling member, as described above in other variations.

FIG. 40 illustrates a variation of a skin treatment applicator 1005 with an elongate body extending about axis 1018 and is shown with a detachable distal treatment tip 1020 with a plurality of rolling members 1022 as shown in the distal tips of FIGS. 41H, 41I, 42A, and 42B to provide a low-friction surface, as described further below. The distal tip 1020 is configured for fluid-assisted exfoliation or microdermabrasion together with application of a fluid or serum to a subject's skin for hydration and absorption of agents, vitamins, etc. The applicator 1005 is designed to be fitted with various distal tips that have different tissue-contacting surfaces or skin interfaces that are specially designed for (i) exfoliation, (ii) serum delivery and absorption, or (iii) a combination of exfoliation and hydration. Several of the variations shown below have a combination of features that provide for exfoliation as well as for enhancing fluid penetration into the subject's skin.

Referring to FIG. 40, the applicator body 1005 is coupled to a negative pressure source 1010 for providing negative pressure within the outflow channel 1015 the applicator body 1005. The negative pressure source 1010 is shown as a remote source with tubing 1023*a* that is coupled to fitting 1023*b* and the outflow channel 1015. The negative pressure source alternatively can be a pump carried within the applicator 1005, as described in previous variations. The distal tip 1020 in the variations of FIGS. 40, 41H, 42A, and 42B is coupled to the applicator 1005 by a press fit, a Luer type lock, or a screw fit where an O-ring may be provided as a seal. The outflow channel 1015 in the applicator body 1005 communicates with cooperating channel 1015' and port 1024 in tip 1020, as can be seen in the sectional view of FIG. 42A.

In the variation of FIG. 40, the applicator 1005 carries a cartridge that comprises a fluid source 1025 and is placed in a receiving space 1026 in the applicator body. The cartridge or fluid source 1025 carries a serum or fluid 1027 that communicates with a flow channel 1028 in the applicator body 1005 that, in turn, communicates with at least one inflow channel 1030 in the distal tip 1020 and at least one inflow port 1032 to deliver the fluid 1027 to the targeted tissue of the subject (see FIGS. 41H and 42A). In another variation, it can be understood that the fluid source 1025 can be remote from the applicator 1005 and communicate with the applicator through flexible tubing (not shown). In a typical variation, the applicator 1005 has connection features that allow for selection of a remote fluid source or the insertion of a cartridge fluid source 1025 into the applicator body 1005 with a threaded or puncture fitting to release the fluid 1027 from the cartridge into the inflow channel 1028.

Figure 41A:
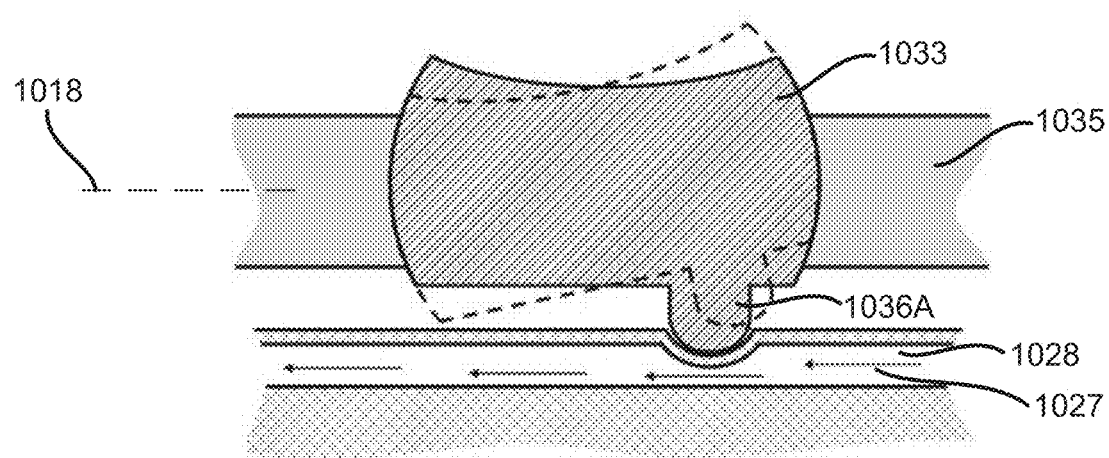
FIG. 41A is a sectional schematic view of the rocker actuator member of FIG. 40 showing a projecting feature of the rocker impinging on a flow channel in an elastomer body that functions as a valve feature.
Figure 41B:
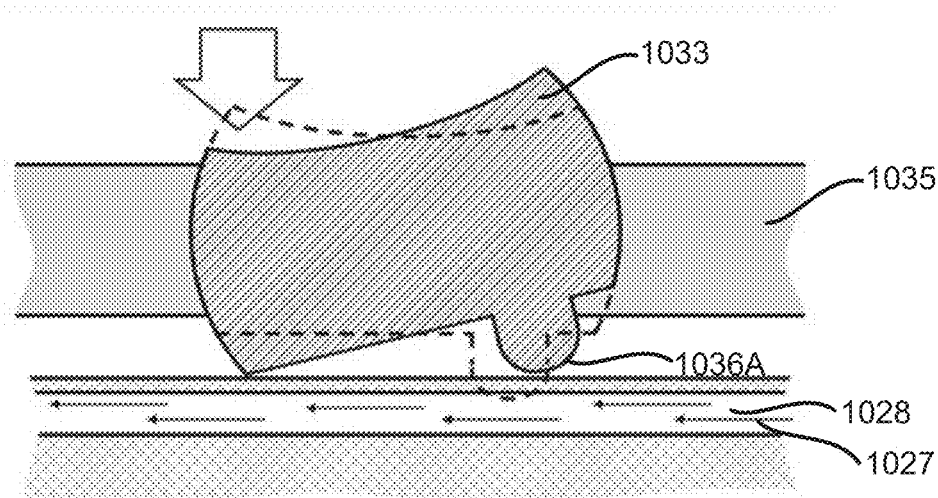
FIG. 41B is a view of the rocker member of FIG. 41A is another position opening the flow channel in the elastomer body.
Figure 41C:
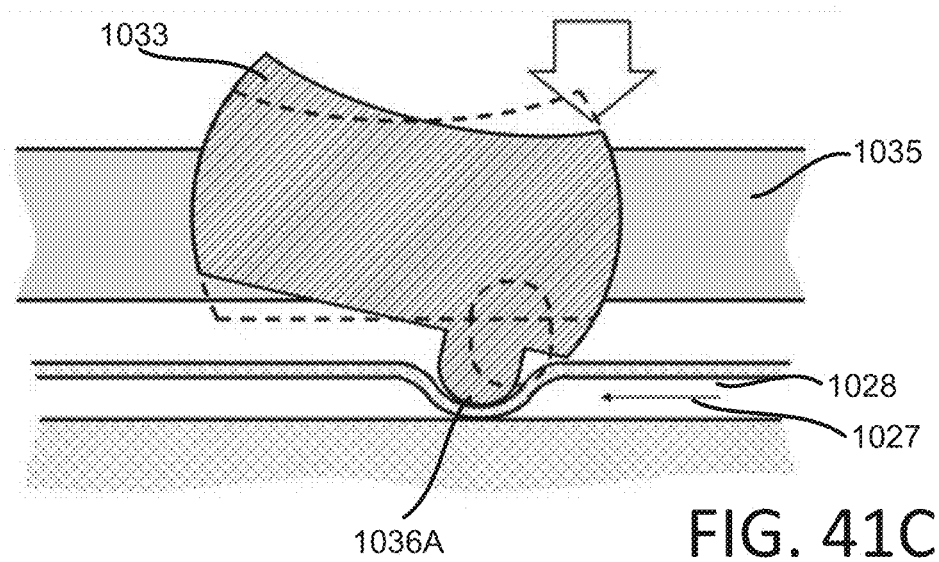
FIG. 41C is another view of the rocker member of FIGS. 41A-41B is a position that closes the flow channel in the elastomer body.

In FIG. 40, it can be seen that the applicator 1005 carries a rocker member or actuator 1033, which functions as a valve actuator for controlling flows from at least one of the inflow of fluid 1027 from the fluid source 1025 and fluid outflow provided by the negative pressure source 1010. In a variation, the rocker member 1033 has a spherical outer surface 1034*a* which allows for 360° rocking or movement within a spherical receiving space 1034*b* in the applicator. In other words, the rocker member 1033 can rotate relative to axis 1018 of the applicator 1005 or can rotate transverse to the axis 1018 of the applicator or any position therebetween. The movement of the rocker member 1033 is adapted to impinge or not impinge on flow passageways in an elastomeric body 1035, as is known in the art of microfluidics (see FIGS. 41A-41E). For example, FIGS. 41A-41C are sectional views of the rocker member 1033 rotating relative to the axis 1018 of the applicator 1005 (FIG. 40) to adjust the flow the fluid 1027 in a fluid inflow channel 1028. In such a variation, the fluid inflow channel 1028 in the elastomeric body 1035 can be compressed by a projecting element 1036A of the rocker member 1033. FIG. 41A shows the rocker member 1033 in a first position that can be spring-loaded to maintain the inflow channel 1028 in a partially restricted condition. FIG. 41B shows the rocker member 1033 moved to a second position where the projecting element 1036A does not impinge the inflow channel 1028 to allow increased fluid inflows. FIG. 41C shows the rocker member 1033 manually moved to a third position wherein the projecting element 1036A completely blocks any fluid flow in the inflow channel 1028.

Figure 41D:
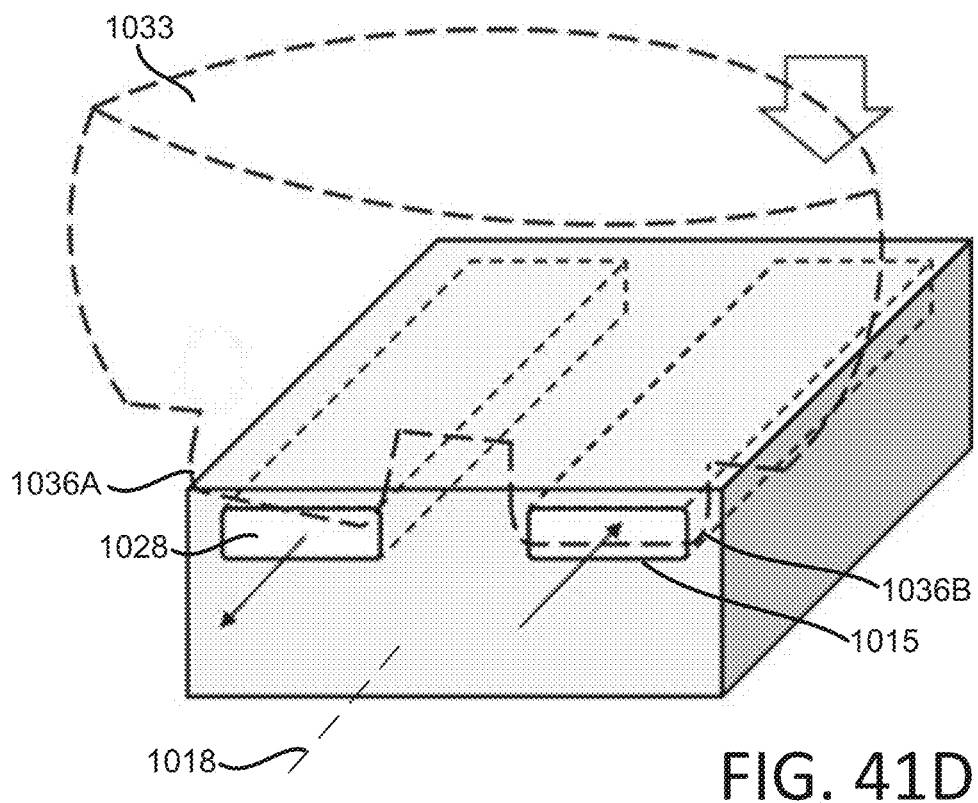
FIG. 41D is a transverse view of the rocker member and elastomer body of FIGS. 41A-41C showing a variation of the rocker that can open and close inflow and outflow channels in an elastomer body.
Figure 41E:
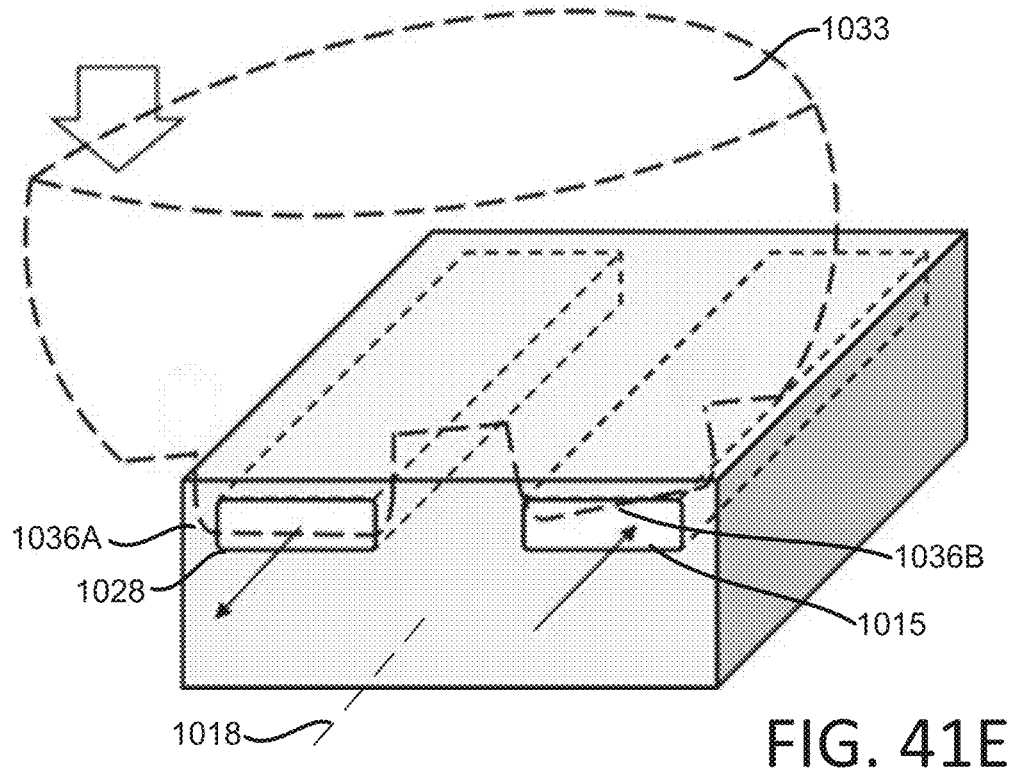
FIG. 41E is another view of the rocker member of FIG. 41D in another position.

FIGS. 41D and 41E are transverse sectional views of the rocker member 1033 of FIGS. 40 to 41C showing the rocker member 1033 in a dashed line with dual projecting elements 1036A and 1036B that are adapted to impinge or not impinge on both an inflow channel 1028 and the outflow channel 1015 extending through the elastomeric body 1035. FIG. 41A shows the projecting element 1036A not impinging on inflow channel 1028 while projecting element 1036B impinges on outflow channel 1015. FIG. 41E shows the rocker member 1033 rocked transverse to axis 1018 of the applicator 1005 to a second position wherein projecting element 1036A impinges the inflow channel 1028 while projecting element 1036B does not impinge the inflow channel 1015. Thus, the rocker member can be moved in an X-axis aligned with axis 1018 of the applicator 1005 or in a Y-axis that is transverse to the axis 1018 of the applicator to adjust both inflows and outflows contemporaneously. While the drawings show an elastomeric body 1035 with flow channels therein that can be opened and closed, the scope of the invention includes other forms of valves that can be actuated by a single actuator member to simultaneously adjust fluid flows within a plurality of flow channels.

Figure 41H:
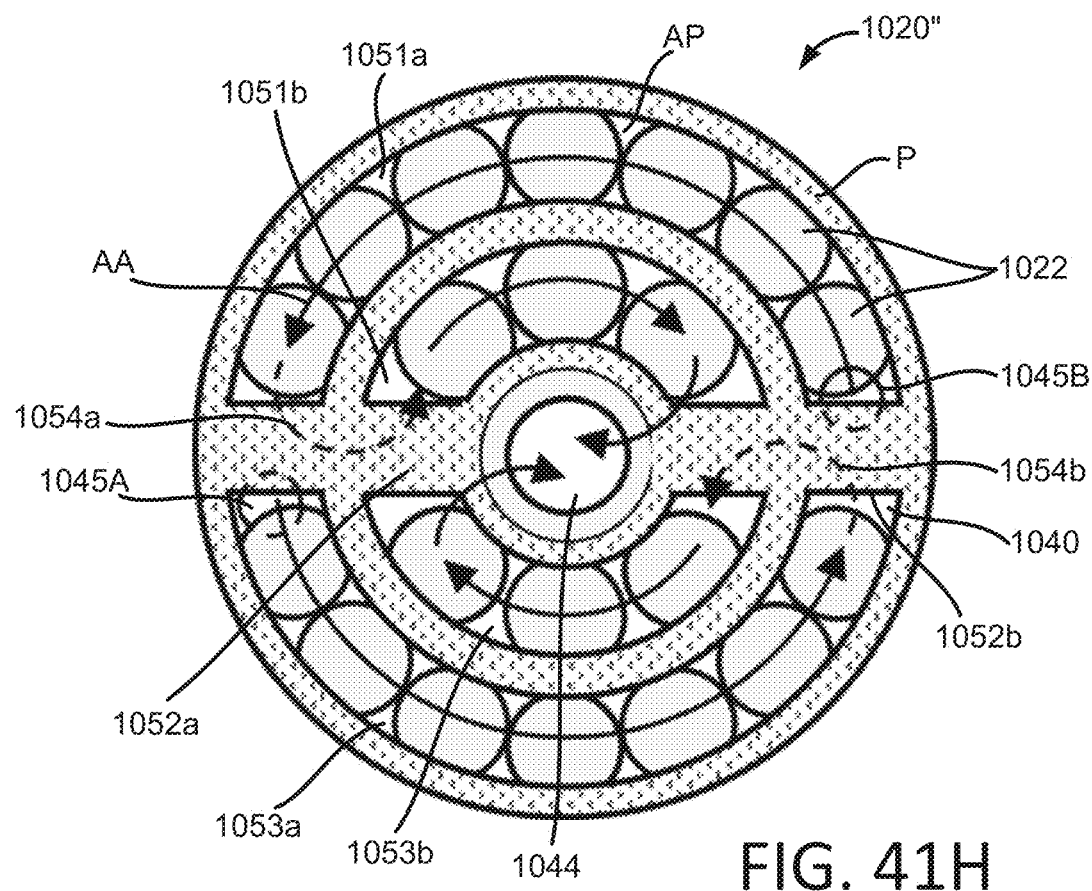
FIG. 41H is an end view of a treatment tip of the type shown in FIGS. 41F-41G that provides for circuitous fluid flows.

FIGS. 41F and 41G are schematic illustrations of an applicator tip 1020' (dashed outline) with flow pathways indicated by arrow AA and AA', where such flow pathways are within recessed spaces or channels in the tip 1020' or which optionally may comprise roller receiving channels 1040 that carry the spherical rolling members 1022 as will be described further below. In FIGS. 41F and 41G, it can be seen that a first flow channel, 1042A communicates with a fluid source, 1025 and a second flow channel, 1042B communicates with a negative pressure source 1010. The flow channels 1042A and 1042B are in an applicator body similar to that of FIG. 40. In a variation, the applicator tip 1020' of FIGS. 41F and 41G has rolling members 120, as shown in FIG. 41H. The applicator has a rocker member 1033', as described above, that is adapted to simultaneously open or close the first and second flow channels 1042A, 1042B while at the same time opening and closing cross-over channels 1043A and 1043B. It can be understood from FIGS. 41F and 41G that the cross-over channels 1043A and 1043B can be used to reverse the direction of fluid flows in the distal tip 1020' from a central port 1044 to at least one peripheral port with two peripheral ports 1045A and 1045B shown in FIGS. 41F and 41G. One of the objectives of using distal tips such as tip 1020' of FIGS. 41F and 41G is to provide elongated, circuitous flow pathways in the tissue-engaging surface of the tip 1020' to maintain fluid in contact with the subject's skin for a longer time interval to enhance fluid penetration into the subject's skin. In FIG. 41F, it can be understood that the projecting element 1046A of the rocker member 1033' is positioned to open valve features 1048A and 1048B of first and second flow channels 1040A and 1040B while projecting element 1046B of rocker member 1033' contemporaneously closes respective valve features 1049A and 1049B of the cross-over flow channels 1043A and 1043B. This arrangement provides for fluid flows through a distal tip 1020' of the type shown in FIGS. 41H and 41I, as indicated by arrows AA in FIGS. 41F, where the inflow is through peripheral ports 1045A and 1045B of the distal tip 1020', and the outflows are through the central port 1044 of the tip. FIG. 41G illustrates the projecting element 1046A of rocker member 1033' in an opposite position which closes valve features 1048A and 1048B of the first and second flow channels 1040A and 1040B while projecting element 1046B contemporaneously opens the valve features 1049A and 1049B of cross-over flow channels 1043A and 1043B. This arrangement thus reverses the circuitous fluid flows through the distal tip 1020' as indicated by arrows AA' wherein the inflows are through central port 1044 and outflows are through the peripheral ports 1045A and 1045B. Thus, in all of the variations of distal tips shown below, it should be appreciated that fluid flows can be reversed from the flow pathways shown in the drawings, that is, from peripheral inflows and central outflows to the opposite directions.

FIG. 41H is an end view of a distal tip 1020" having the configuration shown in FIGS. 41F and 41G with a perimeter portion P adapted to contact and seal against tissue wherein the perimeter portion P surrounds an aspiration portion AP. The aspiration portion AP is configured with the plurality of spherical rollers or rolling members 1022 carried in roller receiving spaces or channels 1040 where fluid flows are shown by arrows AA as inflows through ports 1045A and 1045B and an eventual outflow through central port 1044. Referring to FIG. 41H, it can be seen that the circuitous fluid flows as shown in FIGS. 41F-41G are provided by in or adjacent to the outer roller receiving channel 1051a and the inner roller receiving channel 1051b, where these roller channels extend approximately 180° around the tip 1020". Web elements 1052a and 1052b are provided to separate roller channels 1051a and 1051b from similar roller receiving channels 1053a and 1053b on the opposing side of the tip 1020". Interior passageways indicated at 1054a and 1054b allow for fluid flow between the outer and inner roller channels to provide the circuitous fluid flows indicated by the arrows AA. Thus, as the fluid flows in the roller channels 1051a, 1051b, 1053a, and 1053b and the tip 1020" is translated over tissue, the surfaces of the spherical rolling members 1022 deliver the fluid to the engaged skin while at the same time reducing friction or the forces needed to translate the tip over skin with suitable negative pressure applied to the subject's skin. In a variation, the fluid flow can be reversed as described above, with fluid inflows through central port 1044 and fluid outflows through peripheral ports 1045A and 1045B. The distal-facing surface of the tip 1020" of FIG. 41H, and its features can be concave or planar.

Figure 41I:
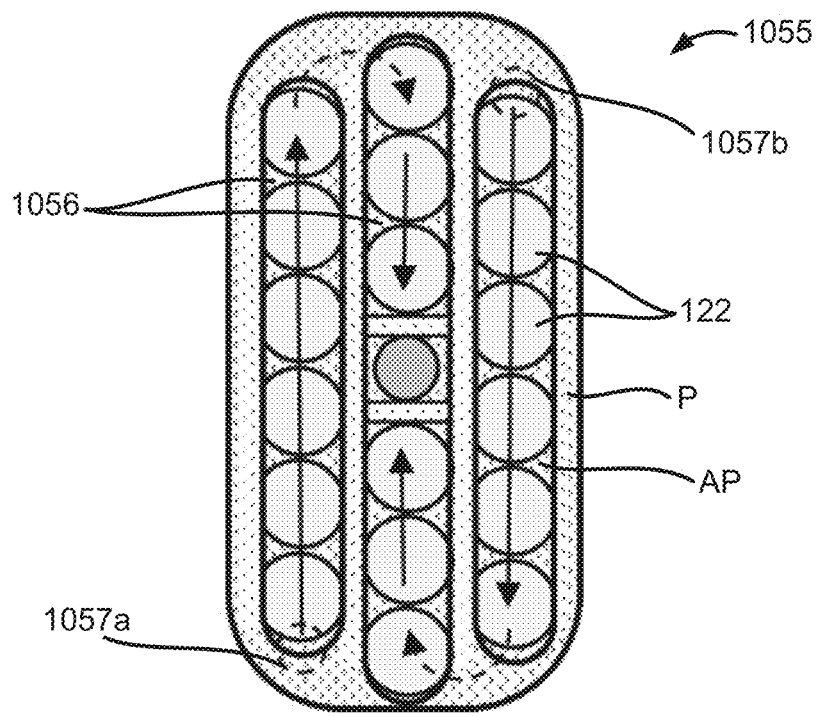
FIG. 41I is an end view of a variation of a distal tip that carries a plurality of rolling members in linear roller channels where circuitous fluid flows are shown with inflows through ports and an eventual outflow through a central port.

FIG. 41I is an end view of a variation of a distal tip 1055 that carries a plurality of rolling members 1022 in linear roller receiving channels 1056, where circuitous fluid flows are again shown by arrows AA with inflows through ports 1057A and 1057B and an eventual outflow through central port 1058. In all other respects, the tip 1055 of FIG. 41I functions as previously described with reference to FIG. 41H. FIGS. 41H and 41I illustrate skin treatment tips that have roller channels that extend in an arc or are linear to provide circuitous fluid flows, but it should be appreciated that the scope of the invention covers any roller receiving channels that are non-linear between a fluid inflow port and a fluid outflow port, which included zig-zag channels, wave-shaped channels, spiral channels, maze-like channels and the like. The spherical rolling members 1022 have a diameter ranging from 1 mm to 5 mm.

Figure 42B:
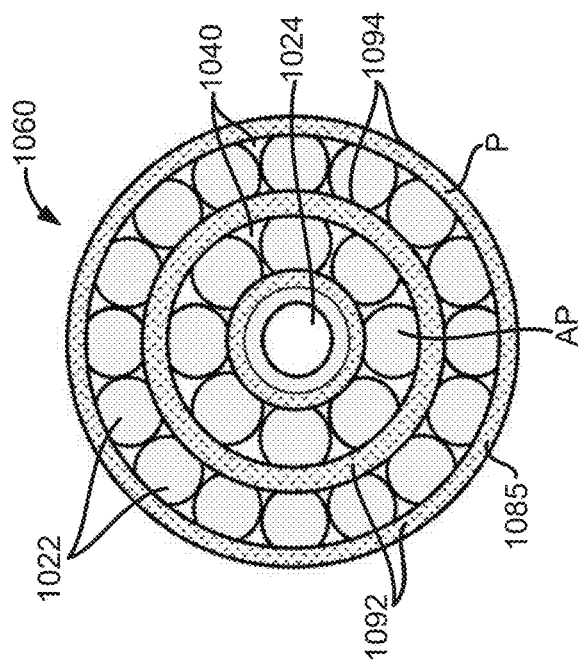
FIG. 42B is an end view of the treatment tip of FIG. 42A.
Figure 42A:
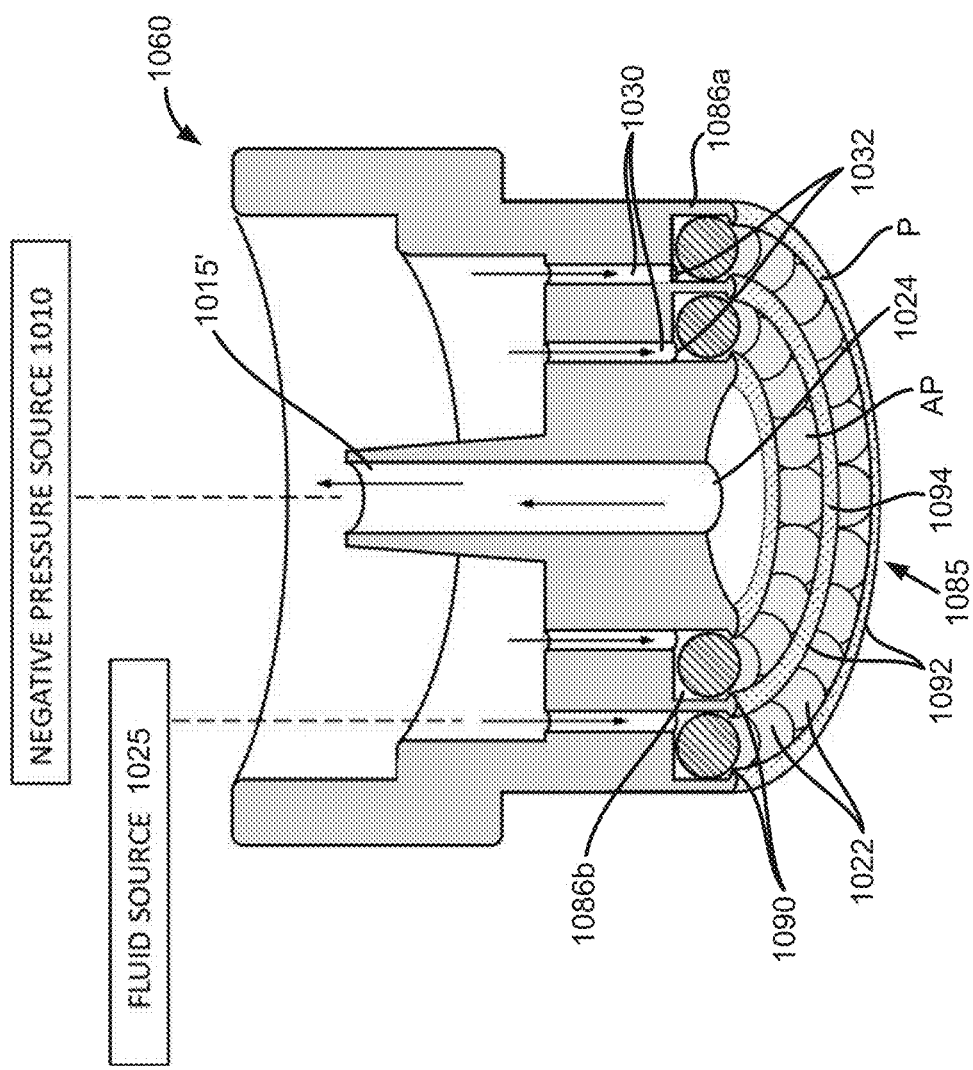
FIG. 42A is a sectional view of a treatment tip with multiple rolling members in concentric roller channels.

Now referring to FIGS. 42A-42B, a variation of a distal treatment tip 1060 is shown with a perimeter portion P surrounding an aspiration portion AP that carries a plurality of rolling members 1022 in at least one roller receiving space or channel in the surface 1085 of the distal tip 1060, with two concentric receiving channels 1086a and 1086b shown in tip 1060. The variation of distal tip in FIGS. 42A-42B, as well as other variations, illustrated FIGS. 43A to 51C, carry a plurality of rolling members 1022 in the skin interface or tissue-contacting surface 1085 to create a low friction surface or low traction interface with the targeted tissue. The low traction interface or surface 1085 allows for ease of movement by reduction of traction during translation of the distal tip across a subject's skin while at the same time allowing higher levels of negative pressure. This configuration allows for enhanced levels of negative pressure, which is advantageous for exfoliation of surface tissues as well as for causing penetration of fluid into the targeted tissue. In this variation as in previous variations, the surface 1085 of the distal tip 1060 has a perimeter portion P that surrounds an aspiration portion AP that is inward from the perimeter portion P. The perimeter portion P contacts targeted tissue and forms a seal during use wherein the aspiration portion AP is in communication with the negative pressure source 1010 so that the targeted tissue is suctioned into contact with all surfaces of the aspiration portion AP and thus draws fluid 1027 through the inflow channels 1030. The spherical rolling members are partly captured in the receiving channels 1086a and 1086b, with a portion of each roller projecting outwardly from the receiving channels, which manipulates the targeted tissue by stretching the tissue surface over the projecting roller portion during use when tissue is suctioned into contact with the aspiration portion AP. The manipulated tissue allows for enhanced hydration by the fluid introduced into and circulating through the aspiration portion AP.

The spherical rollers or rolling members 1022 can be of metal, polymer, ceramic, or glass, and the tip 1060 is a molded plastic wherein a variation has varying materials between a treatment tip and the rolling members 1022 to reduce friction between the components. In a variation where an LED is used as described above, the treatment tip and spherical rolling members are of a transparent material. The rolling members 1022 can optionally vary in diameter in a treatment tip.

FIG. 42B is an end view of the distal tip 1060 of FIG. 42A with rolling members 1022 in the concentric channels 1086a and 1086b. The number rolling members 1022 can vary from three rolling members (in a single channel) to 100 or more rolling members in total disposed in multiple channels, where the distal tissue-contacting surface 1085 and channels therein can have a round or oval shape. The number of roller receiving spaces or channels holding the rolling members can range from 1 to 6.

In general, a distal tip such as treatment tip 1060 in FIGS. 42A-42B corresponding to the invention has a tissue interface or tissue-contacting surface 1085 that includes a plurality of spherical rolling members 1022 wherein a surface area (in plan view) of the spherical rolling members 1022 is at least 25% of the total surface area of the tissue surface 1085. Often, such a surface area of the spherical rolling members is at least 50% of the total surface area of tissue surface 1085 and in a variation, is at least 70% of the surface area of the tissue surface 1085.

The variations of distal tips 1020' and 1060 of FIGS. 41H, 41I, 42A, and 42B are optimized for exfoliation as well as the application and absorption of more expensive serums or medicaments. The fluid 1027 can be sterile water, saline, water with a soap, serums with vitamins, exfoliants, or the like for entraining exfoliated tissue debris in the outflows. It can be understood, for example, from FIG. 42A that the distal edges of the roller channels 1086a and 1086b have projecting edges or lips 1090 that lock and maintain the rolling members 1022 in the roller channels. The surfaces of the distal channel edges 1092 contact targeted tissue for the purpose of exfoliation. In a variation, the surfaces of the channel edges 1092 are adapted for abrasion or exfoliation with abrasive particles 1094, sharp edges or serrated edges for exfoliating the targeted tissue. The outermost peripheral channel edge or perimeter portion P functions as a seal against the targeted tissue as described above to maintain the negative pressure in the central or aspiration portion AP of the distal tip 1060. The surface of the perimeter portion P can be smooth or can have abrasive features. The distal-facing surface 1085 of the tip 1060 may be planar or concave, as shown in FIG. 42A.

In FIGS. 42A and 42B, it can be seen that central outflow port 1024, that communicates with the negative pressure source 1010, is relatively large for aspirating fluids and exfoliated tissue debris. In the variation of FIG. 42A, the fluid inflow channels 1030 in the distal tip 1060 communicate with both roller receiving channels 1086a and 1086b to allow for rapid infusion of fluids into the distal tip 1060 to interface with the targeted tissue, but inflows to a single roller receiving channel is also possible as can be understood from the variation of FIG. 41H.

Figure 43B:
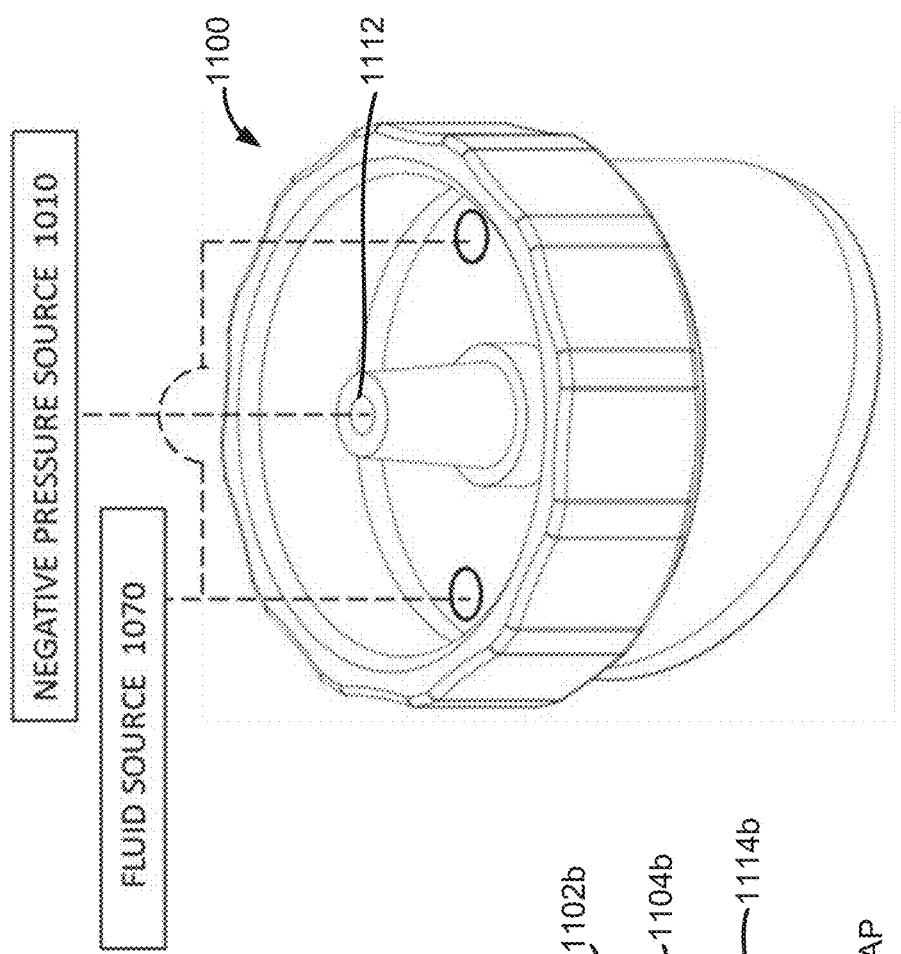
FIG. 43B is another view of the treatment tip of FIG. 43A from a different angle.
Figure 43A:
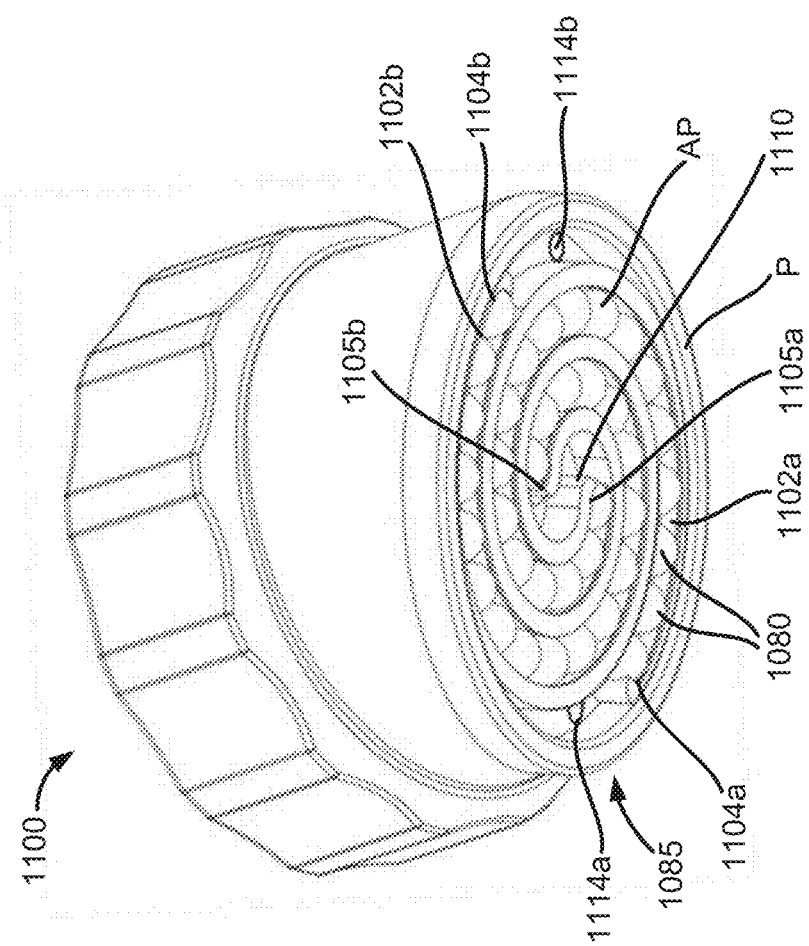
FIG. 43A is a perspective view of a treatment tip with multiple rolling members in intertwined spiral roller channels.

FIGS. 43A to 43D illustrate another variation of distal tip 1100 for coupling with the applicator 1005 of FIG. 40. The tip 1100 has a plurality of rolling members 1080 captured in spiral receiving channels 1102a and 1102b, wherein the plurality of rolling members 1080 again comprise greater than 25% or greater than 50% of the surface area of the tissue-contacting surface 1085 of the tip 1100. This variation of distal tip 1100 may be adapted for application of specific serums and the enhanced absorption of such serums in the targeted tissue. As can be understood from FIGS. 43A-43D, the distal tip 1100 again is designed to maintain fluid flows in contact with the targeted tissue for an extended time interval during use compared to some previous variations adapted for exfoliation, as the fluid or serum from fluid source 1070 flows through the channels 1102a, 1102b that have a varying radius and spiral inwardly. In FIG. 43A, it can be seen that the roller channels 1102a, 1102b spiral from radially outward ends 1104a, 1104b to radially inward ends 1105a, 1105b close to the central fluid outflow port 1110 and outflow channel 1112 (FIGS. 43C-43D). The fluid inflow ports 1114a, 1114b are at the radially outward ends 1104a, 1104b of the spiral channels, thus spaced far apart from the central fluid outflow port 1110. In the variation of FIGS. 43A-43D, the tip 1100 has two spiral channels, 1102a, 1102b but other similar variations of treatment tips can have from one spiral channel to six or more spiral channels.

In use, it can be understood that the perimeter portion P of the distal tip 1100, which can be round or oval, can function as a seal against the tissue. During use, activation of the negative pressure source 1010 will draw fluid inflows to the outer periphery of the spiral channels 1102a, 1102b, and the rolling members 1080 will roll the fluid onto the contacted tissue at the same time the fluid then flows in a spiraling path towards the central outflow port 1110. By this means, the fluid or serum is maintained in contact with the targeted tissue for an extended time interval.

In general, an applicator of the type shown in FIG. 40 above and in FIGS. 28-29 of commonly-owned and co-pending U.S. patent application Ser. No. 17/650,747 can be coupled with a distal tip for treating targeted tissue, as shown in FIGS. 41H-42D that includes a perimeter portion P configured for contacting the targeted tissue that surrounds an aspiration portion AP, a plurality of spherical rolling members carried in at least one arc-shaped receiving channel in the aspiration portion, at least one aspiration channel in the aspiration portion communicating with a negative pressure source, and an outlet in the distal tip in communication with a fluid source wherein contacting and moving the distal tip against the targeted tissue causes rotation of the plurality of spherical rolling members to reduce traction of the distal tip and causes the perimeter portion to seal against the tissue so that the negative pressure source draws fluid from a fluid source into the aspiration portion. The at least one arc-shaped receiving channel in the distal tip extends from 90° to 360° around the aspiration portion. FIG. 41H shows a variation of tip 1020" wherein the arc-shaped channels 1040 that extend approximately 180° around the aspiration portion AP. FIGS. 42A and 42B show a variation of tip 1060 wherein the arc-shaped channels 1040 are continuous channels extending 360° around the aspiration portion AP. The variations of FIGS. 41H, 42A and 42B illustrate arc-shaped receiving spaces or channels 1040 that are at least partly circular with a constant radius. The distal treatment tip 1100 shown in FIGS. 43A-43D has arc-shaped receiving channels 1102a and 1102b that have a varying radius and extend in a spiral configuration.

Figure 44:
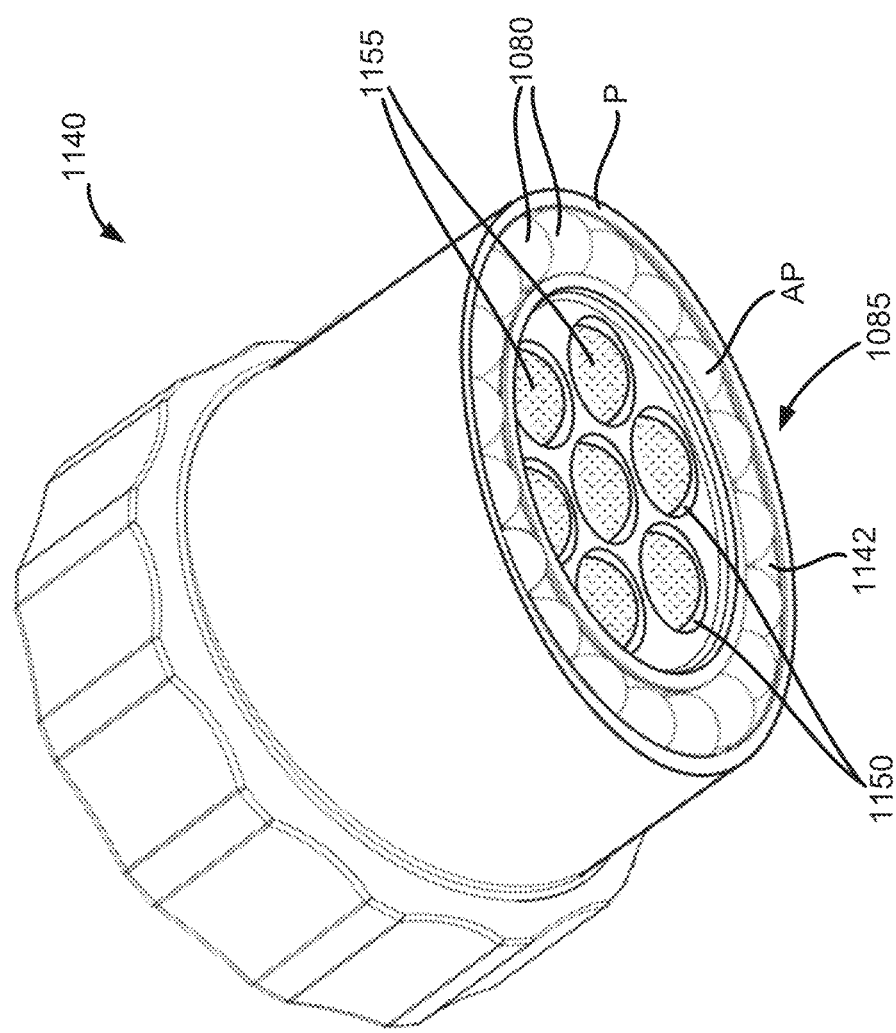
FIG. 44 is a perspective view of a variation of a treatment tip with an outer roller channel carrying rolling members and an inner region carrying rolling members in individual sockets.

FIG. 44 illustrates another form of distal tip 1140 that has rolling members 1080 in a peripheral roller receiving channel 1142, similar to the previous variation with a perimeter portion P that can form a seal around the interior aspiration portion AP as described previously. The fluid inflow channel or channels (not shown) communicate with roller receiving channel 1142 as in previous variations. In the tip 1140 of FIG. 44, the fluid outflow channels for aspiration communicate with the receiving sockets 1150 that house the rolling members 1155 in the central part of the aspiration portion AP. In this variation, the rolling members 1080 and 1155 comprise a surface area greater than 50% of the surface area of the tissue-contacting surface 1085 of the tip 1140.

FIGS. 45A-45C illustrate another form of distal tip 1160 that has sealing perimeter portion 1162 surrounding rolling members 1165 that are each captured in a roller receiving pocket 1166 (FIG. 45C) in the aspiration portion 1168. The fluid inflow channels 1170 communicate with radially outward roller receiving pockets 1166 and the fluid outflow channel 1175 for aspiration communicates with the central rolling member 1165' in receiving pocket 1166' that houses central rolling members 1165' in the central part of the aspiration portion 1168. In this variation, the rolling members 1165 and 1165' comprise a surface area greater than 50% of the surface area of the tissue-contacting surface 1085 of the tip 1160.

Figure 47:
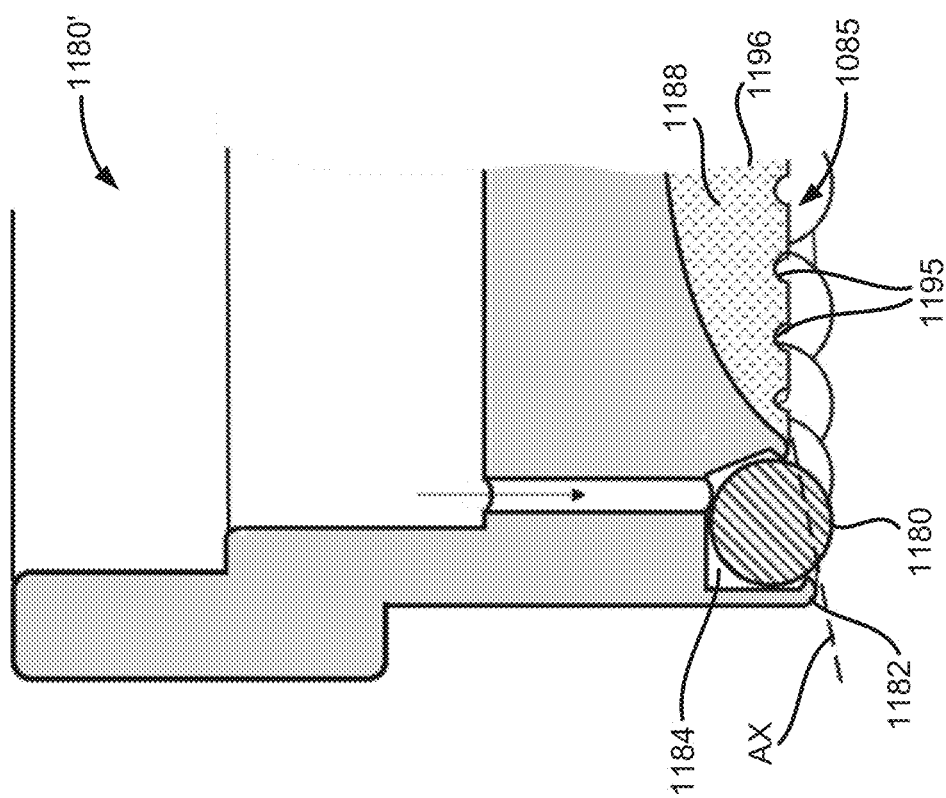
FIG. 47 is a sectional view of a variation of a treatment tip similar to that of FIGS. 46A-46B showing notch features.

FIGS. 46A-46B illustrate another form of distal tip 1180 that has sealing perimeter portion 1182 surrounding rolling members 1181 in a roller receiving channel 1184 as described previously in the aspiration portion 1185. The fluid inflow channels 1186 communicate with the roller channel 1184. The distal tip 1180 of FIGS. 46A-46B is adapted for more aggressive dermabrasion and has a concave central portion 1188 that has abrasive particles 1190, such as coarse diamond dust affixed thereto. The fluid outflow port 1192 and outflow channel 1194 is positioned in the center of the tip 1180. FIG. 47 is a sectional view of a portion of a tip 1180' that is similar to that of FIGS. 46A-46B but includes notches 1195 in an interior edge 1196 of the roller channel 1184. In order to aggressively abrade tissue, the notches 1195 allow for increased flow of fluid into the abrasive central portion 1188 as the tip is moved over tissue. FIG. 47 also shows angle AX wherein the surface of the roller channel 1184 is not transverse to the axis (FIG. 40) of the treatment tip 1180 but is angled inwardly to provide a concave tissue-contacting surface 1085.

Figure 49:
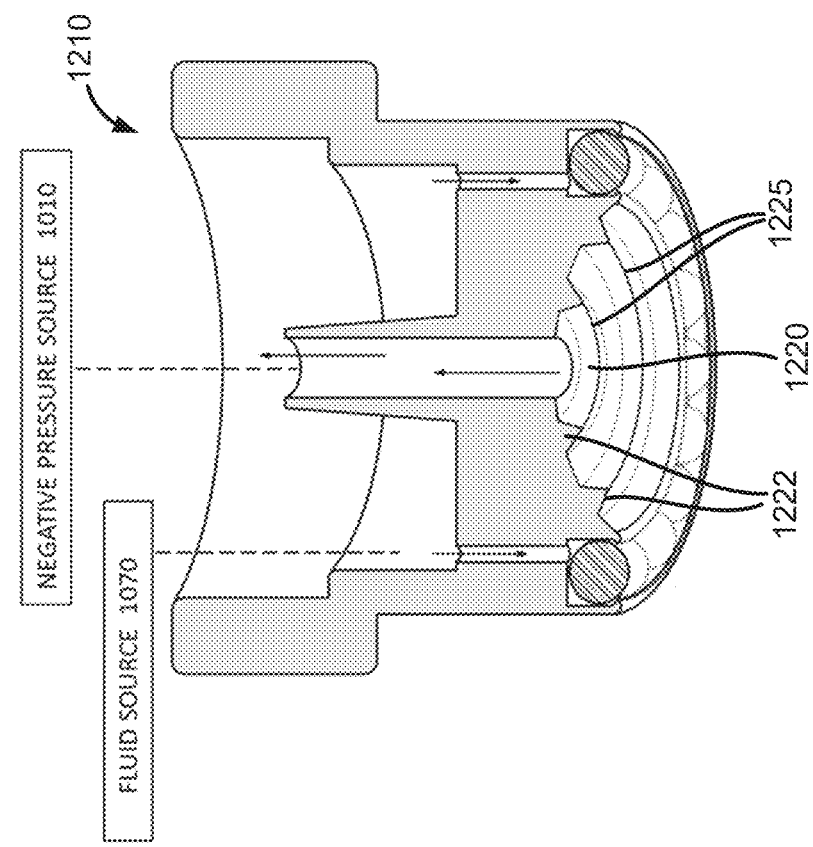
FIG. 49 is a sectional view of a treatment tip with an outer roller channel carrying rolling members and a central concave portion having concentric sharp edge features.
Figure 48:
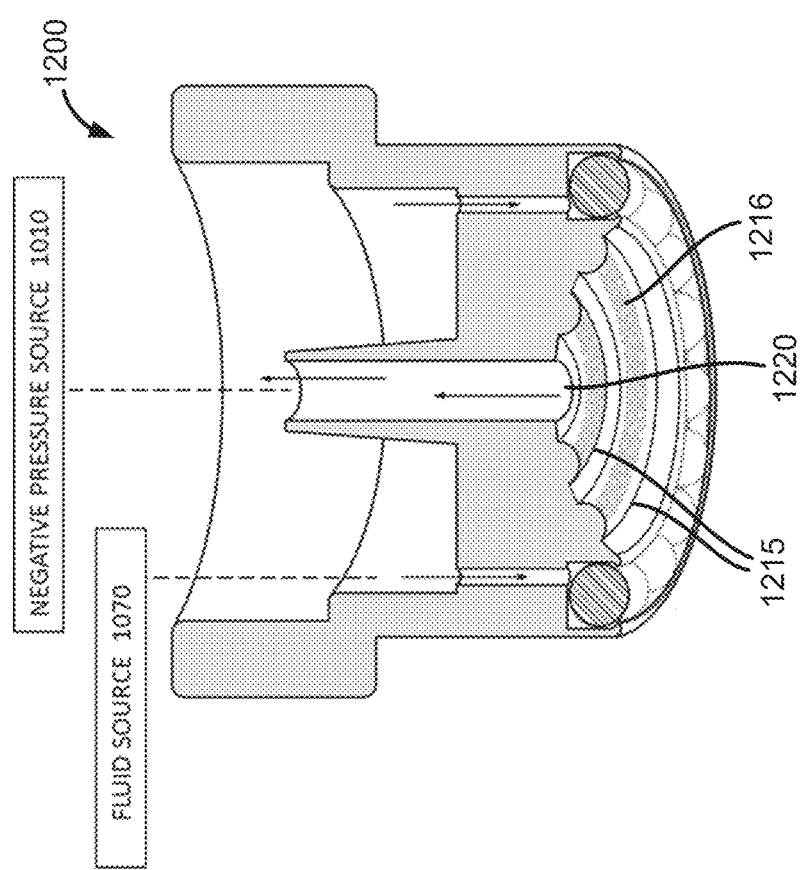
FIG. 48 is a sectional view of a variation of a treatment tip with an outer roller channel carrying rolling members and a central concave portion having an undulating surface with abrasives.
Figure 50:
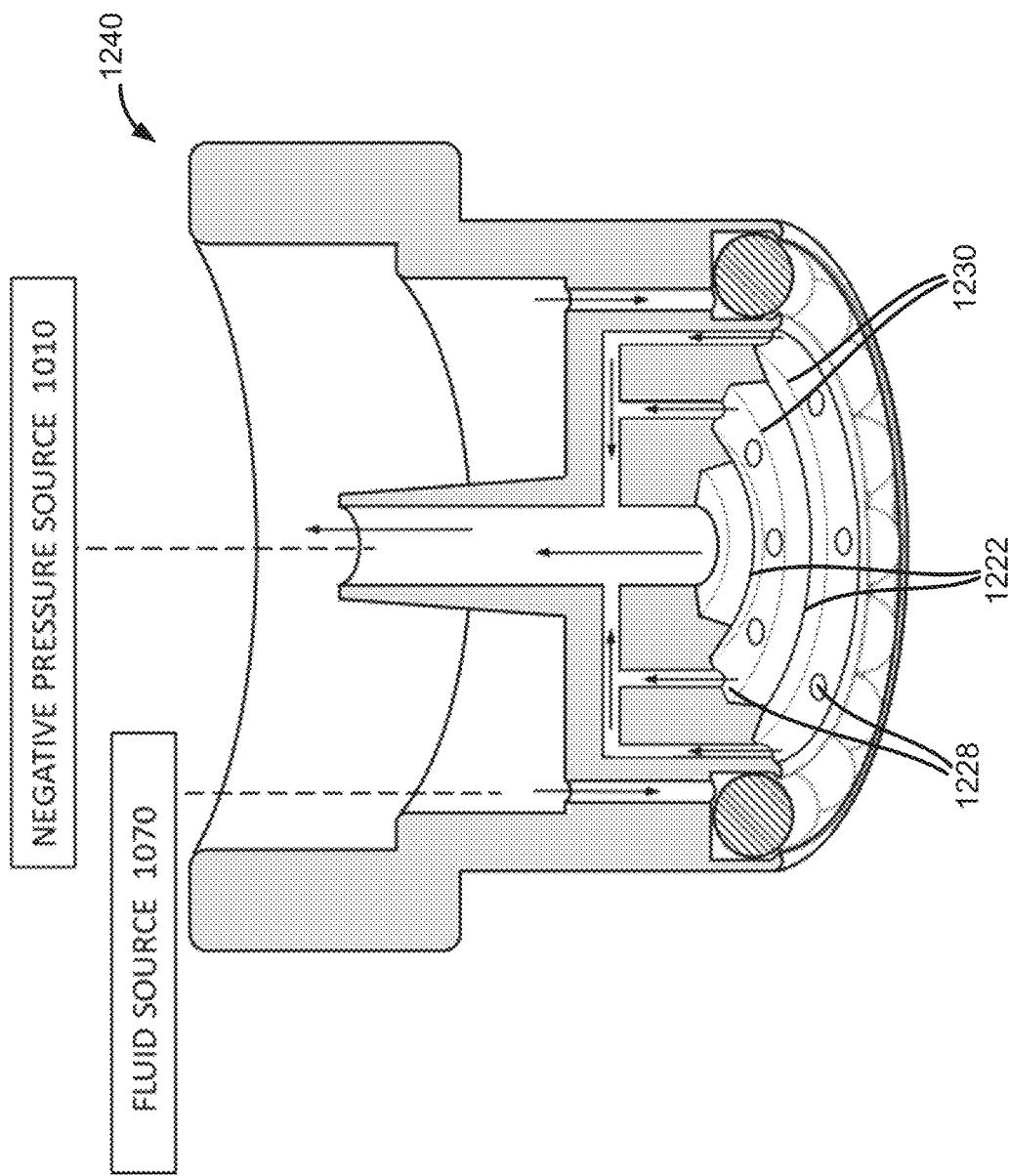
FIG. 50 is a sectional view of a treatment tip similar to that of FIG. 49 with the addition of a plurality of aspiration ports in the central concave portion.
Figure 51:
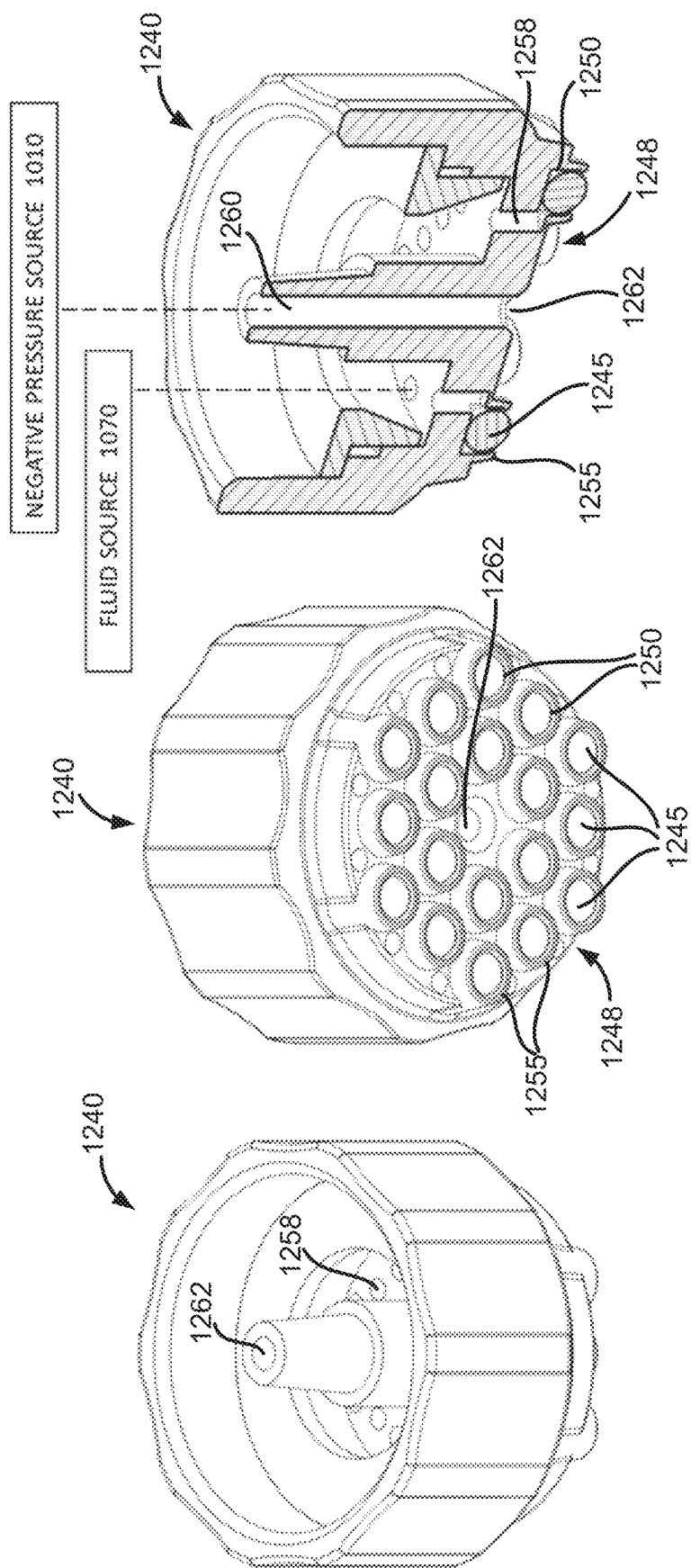
FIG. 51A is a perspective view of another variation of a treatment tip with rolling members carried in individual sockets.
FIG. 51B is another view of the treatment tip of FIG. 51A from a different angle.
FIG. 51C is another view of the treatment tip of FIGS. 51A-51B.

FIGS. 48 and 49 illustrate other variations of distal tips 1200 and 1210 that are similar to the tip 1180 of FIGS. 46A-46B. These variations differ in that the concave central portions have projecting features for engaging and manipulating targeted tissue, wherein stretching the tissue enhances fluid penetration into the tissue. The distal tip 1200 of FIG. 48 has undulations 1215 that may be concentric or spiraling with an abrasive surface 1216 on the crest of the undulations for abrading tissue and a central aspiration port 1220. The distal tip 1210 of FIG. 49 has projecting features 1222 that are concentric or spiral with sharp edges 1225 for abrading tissue. FIG. 50 illustrates another variation of a distal tip 1240 that is similar to the tip 1210 of FIG. 49 and includes a plurality of aspiration ports 1228 is the recesses 1230 between the projecting features 1222 to enhance suction of tissue into the recesses 1230 to enhance stretching of the targeted tissue.

FIGS. 51A-51C illustrate another variation of a distal tip 1240 that again carries a plurality of spherical rolling members or rollerballs 1245 is a tissue-contacting surface 1248. The distal tip 1240 of FIG. 51A-51C differs in that each rollerball 1245 is carried in a roller socket 1250, wherein the tissue-contacting surface 1248 has a distally projecting ridge 1255 around each rollerball 1245 that forms a seal against targeted tissue when in use. This variation differs from the previous variations in which the perimeter of the distal tip formed a seal around a plurality of rolling members, as shown in FIGS. 42A-50. In the distal treatment tip 1240 of FIGS. 51A-51C, the fluid inflow channels 1258 communicate with each roller receiving space or socket 1250 so that fluid flows outward around the rollerballs 1245. The aspiration channel 1260 and aspiration port 1262 is centrally positioned in the tip 1240, and when pressed into targeted tissue, the negative pressure applied is sufficient to draw fluid through the inflow channels 1258 and sockets 1250 to apply the fluid to the targeted tissue. In this variation, the projecting ridges 1255 around each socket 1250 can carry abrasives or have sharp edges for exfoliating tissue as the surface 1248 is translated over tissue tips while the rollerball to reduce friction.

Figure 52:
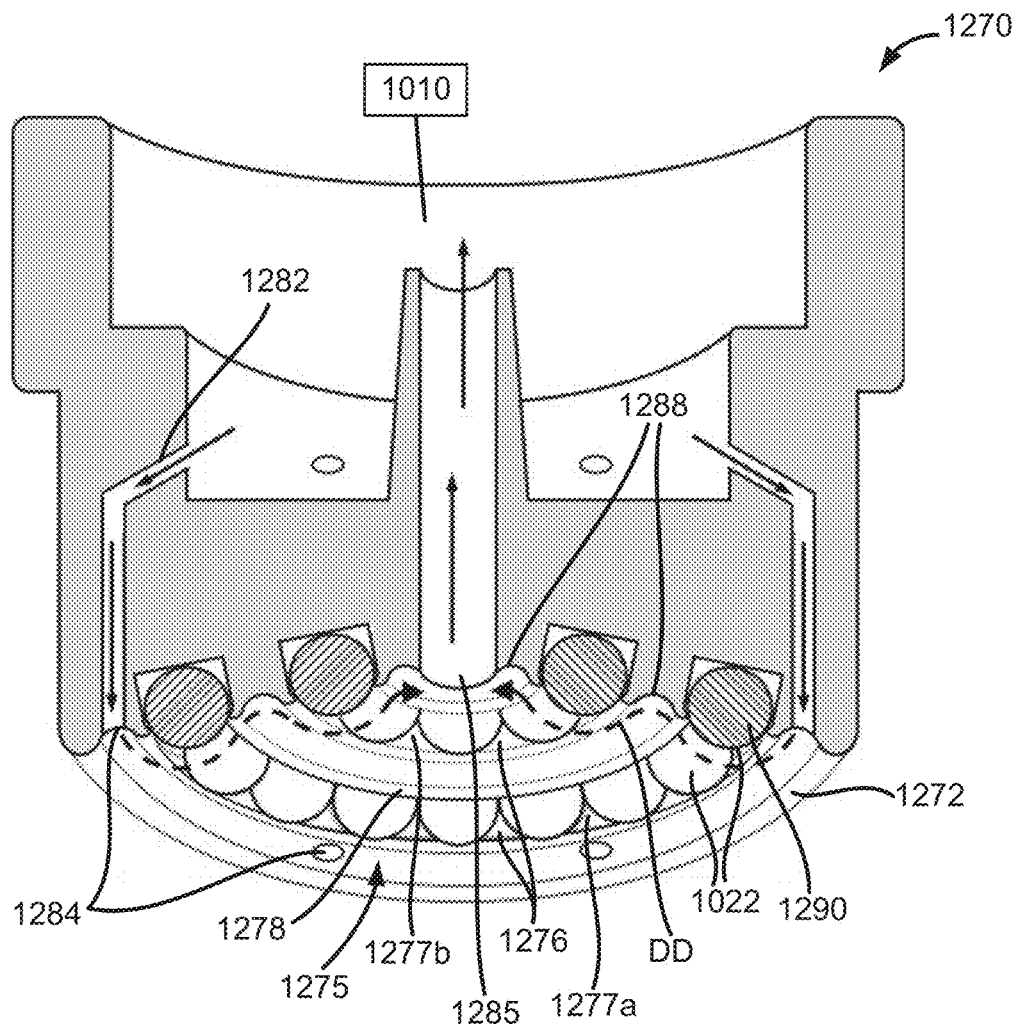
FIG. 52 is a sectional view of a treatment tip with multiple rolling members in a roller receiving channel in the aspiration portion of the tip with fluid inflow and outflow channels on opposing sides of the roller receiving channels.

Now referring to FIG. 52, another variation of a distal treatment tip 1270 is shown with a perimeter portion 1272 surrounding an aspiration portion 1275 that again carries a plurality of spherical rollers or rolling members 1022 in at least one roller receiving space or channel 1276, with two concentric receiving channels 1277a and 1277b in the tissue-contact surface 1278 of the aspiration portion 1275 of tip 1270. In this variation, the plurality of spherical rolling members 1022 in the aspiration portion 1275 provide a low traction interface with the targeted tissue as described above. This configuration allows for enhanced levels of negative pressure, which is advantageous for exfoliation of surface tissues as well as for causing penetration of fluid into the targeted tissue. In this variation, the perimeter portion 1272 again contacts targeted tissue and forms a seal during use when suctioned against tissue. FIG. 52 shows a plurality of channels 1282 communicating with first ports 1284, where the channels can be connected to a fluid source. A central or second port 1285 is in communication with the negative pressure source 1010 that is adapted to suction the targeted tissue into contact with all surfaces of the aspiration portion 1275 and contemporaneously draw fluid from the fluid source through the at least one flow channel 1282 to the at least one first port 1284.

As can be seen in FIG. 52, the distal tip 1270 is configured with the first ports or ports 1284 and the central or second port 1285 on opposing sides of the at least one roller receiving channel 1276 and rolling members 1022. Further, the tip 1270 is optionally configured with a groove or recess 1288 in the surface 1278 of the tip 1270 adjacent to one or both sides of the roller receiving channels 1276. The edges of each receiving channels 1276 and each recess 1288 further can include sharp edges or abrasives for abrading and removing tissue. This configuration thus allows for the distally-projecting portions 1290 of the rolling members 1022 and recesses 1288 in surface 1278 to manipulate and stretch the surface of the targeted tissue as the negative pressure suctions tissue into contact with the tissue-contact surface 1278. As shown by arrows DD in FIG. 52, the flow of fluid over the undulating configuration of the surface 1278 and rolling members 1022 of the tip 1270 is adapted to enhance penetration of the fluid into the manipulated and stretched tissue which may also be abraded to further enhance fluid penetration into the targeted tissue. The aspiration portion 1275 can have a concave configuration. In this variation, the receiving spaces or channels 1276 are flooded with fluid and roll such fluid onto the tissue, as there are no fluid flows directly into or out of the receiving channels 1276 from any port in the channels 1276. In the variation of distal tip 1270 of FIG. 52, it should be appreciated that the system can be adapted to reverse the flow of fluids between the first and second ports as described above.

While the applicators and distal tips above have been described for delivery of treatment media to a subject's skin and lips largely for skin rejuvenation and cosmetic purposes, the negative pressure applicator can also be used for enhancing delivery of any type of pharmaceuticals through an exposed tissue surface, such as analgesics, anti-inflammatory drugs, stimulants, hormones and the like.

Although particular embodiments of the present invention have been described above in detail, it will be understood that this description is merely for purposes of illustration, and the above description of the invention is not exhaustive. Specific features of the invention are shown in some drawings and not in others, and this is for convenience only, and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for treating a targeted tissue of a subject, comprising:
providing an applicator with a distal tip having a perimeter portion surrounding an aspiration portion, at least one spherical roller member in the aspiration portion and partly captured in a receiving space with a projecting roller portion projecting outwardly from the receiving space, a first port in the aspiration portion spaced apart from the receiving space communicating with a fluid source, and a second port in the aspiration portion communicating with a negative pressure source;
contacting the targeted tissue with the distal tip, where the perimeter portion seals the distal tip against the targeted tissue;
applying negative pressure through the second port thereby suctioning targeted tissue against the aspiration portion and moving the distal tip over the targeted tissue while suctioning such that rotation of the at least one spherical roller member against tissue increases ease of movement of the distal tip while contemporaneously cause the projecting roller portion to manipulate the targeted tissue; and
wherein the negative pressure draws a fluid from the fluid source through the first port in the distal tip to hydrate the targeted tissue.

2. The method of claim 1 wherein the at least one spherical roller member comprises a plurality of spherical roller members carried in an arc-shaped receiving space in the aspiration portion.

3. The method of claim 2 wherein the first port and the second port are disposed on opposing sides of the arc-shaped receiving space.

4. The method of claim 2 wherein the second port is within the arc-shaped receiving space.

5. The method of claim 2 wherein the arc-shaped receiving space extends from 90 to 360 degrees around the aspiration portion.

6. The method of claim 1 wherein the distal tip is configured with a plurality of arc-shaped receiving spaces each carrying a plurality of spherical roller members.

7. The method of claim 1 wherein the distal tip has an abrasive portion and wherein moving the distal tip over the targeted tissue abrades tissue.

8. The method of claim 1 wherein the fluid is drawn from the fluid source that is at least one of a remote fluid source and a fluid source carried by the applicator.

9. A device for treating a targeted tissue of a subject, comprising:
an applicator body;
a negative pressure source;
a distal tip of the applicator body having a perimeter portion configured for contacting the targeted tissue, wherein the perimeter portion surrounds an aspiration portion;
a plurality of spherical rolling members each carried in a plurality of arc-shaped receiving channel spaces in the aspiration portion;
at least one first port in the aspiration portion communicating with the negative pressure source;
a second port in the distal tip in communication with a fluid source; and
wherein contacting and moving the distal tip against the targeted tissue when applying a negative pressure from the negative pressure source causes rotation of the plurality of spherical rolling members reduce traction and ease movement of the distal tip across the targeted tissue while the perimeter portion forms a seal against the targeted tissue to cause the negative pressure source to draw fluid from the fluid source into the aspiration portion.

10. The device of claim 9 wherein the arc-shaped receiving channel space extends from 90 to 360 degrees around the aspiration portion.

11. The device of claim 9 wherein the arc-shaped receiving channel space has a constant radius.

12. The device of claim 9 wherein the arc-shaped receiving channel space has a varying radius.

13. The device of claim 9 wherein the plurality of arc-shaped receiving channel spaces have a concentric configuration.

14. The device of claim 9 wherein arc-shaped receiving channel space carries at least three spherical rolling members.

15. The device of claim 9 wherein a distal-facing surface of the aspiration portion is concave.

16. The device of claim 9 wherein a surface area of the plurality of spherical rolling members comprises at least 25% of a total surface area of a distal-facing surface of the distal tip.

17. The device of claim 9 further comprising a recessed groove on at least one side of the arc-shaped receiving channel space.

18. The device of claim 9 wherein at least one edge of the arc-shaped receiving channel space is configured to abrade or remove tissue.

19. The device of claim 9 wherein the plurality of spherical rolling members have a diameter ranging from 1 mm to 5 mm.

* * * * *